(12) United States Patent
Zhang et al.

(10) Patent No.: US 11,608,384 B2
(45) Date of Patent: Mar. 21, 2023

(54) HUMANIZED ANTI-TPBG ANTIBODY, PREPARATION METHOD THEREFOR, CONJUGATE THEREOF, AND APPLICATIONS

(71) Applicant: XDCEXPLORER (SHANGHAI) CO., LTD., Shanghai (CN)

(72) Inventors: Ying Zhang, Shanghai (CN); Shiyong Gong, Shanghai (CN); Xiaolan Sun, Shanghai (CN); Tengjiao Xu, Shanghai (CN); Fei Peng, Shanghai (CN); Yuzhu Chen, Shanghai (CN); Lile Liu, Shanghai (CN)

(73) Assignee: XDCEXPLORER (SHANGHAI) CO., LTD., Shanghai (CN)

( * ) Notice: Subject to any disclaimer, the term of this patent is extended or adjusted under 35 U.S.C. 154(b) by 385 days.

(21) Appl. No.: 16/499,995

(22) PCT Filed: Apr. 4, 2018

(86) PCT No.: PCT/CN2018/081853
§ 371 (c)(1),
(2) Date: Oct. 1, 2019

(87) PCT Pub. No.: WO2018/184558
PCT Pub. Date: Oct. 11, 2018

(65) Prior Publication Data
US 2020/0062856 A1    Feb. 27, 2020

(30) Foreign Application Priority Data
Apr. 5, 2017 (CN) .......................... 201710218524.1

(51) Int. Cl.
| C07K 16/30 | (2006.01) |
| A61K 47/68 | (2017.01) |
| A61P 35/00 | (2006.01) |
| C12N 15/63 | (2006.01) |
| G01N 33/569 | (2006.01) |

(52) U.S. Cl.
CPC .......... *C07K 16/30* (2013.01); *A61K 47/6851* (2017.08); *A61P 35/00* (2018.01); *C12N 15/63* (2013.01); *G01N 33/56966* (2013.01)

(58) Field of Classification Search
CPC ............................ A61P 35/00; A61K 47/6851
See application file for complete search history.

(56) References Cited

U.S. PATENT DOCUMENTS

| 2014/0213770 A1* | 7/2014 | Dong ..................... G16B 35/20 |
| | | 530/387.3 |
| 2016/0081314 A1* | 3/2016 | Thurston ............ C07K 14/7051 |
| | | 800/6 |
| 2021/0198377 A1* | 7/2021 | Sun .................... A61K 47/6877 |

FOREIGN PATENT DOCUMENTS

| CN | 101035564 A | 9/2007 |
| CN | 101437850 A | 5/2009 |
| CN | 106916227 A | 7/2017 |
| EP | 2368914 A1 | 9/2011 |
| EP | 3130356 A1 | 2/2017 |
| EP | 3395834 A1 | 10/2018 |
| WO | 2006031653 A2 | 3/2006 |
| WO | 2007106744 A2 | 9/2007 |

OTHER PUBLICATIONS

Ahmadzadeh et al, Antibody Humanization Methods for Development of Therapeutic Applications, 2014, vol. 33, No. 2, p. 67-73 (Year: 2014).*
Damelin M et al., "Evolving strategies for target selection for antibody-drug conjugates", Pharmaceutical Research, 2015, vol. 32, pp. 3494-3507.
Fernanda V. Castro et al., "Regulation of autologous immunity to the mouse 5T4 oncofoetal antigen: implications for immunotherapy". Cancer Immunol Immunother. 2012, vol. 61, No. 7, pp. 1005-1018.
G. Kohler & C. Milstein, "Continuous cultures of fused cells secreting antibody of predefined specificity", Nature, 1975, vol. 256, pp. 495-497.
International Search Report and Written Opinion of PCT/CN2018/081853 dated Jul. 4, 2018.
Dec. 3, 2020—(CN) Office Action—App No. 201810298246.X.
Jul. 28, 2021—(CN) Office Action—App No. 201810298246.X.
Mauricio Leal et al.,"Preclinical Development of an anti-5T4 Antibody-Drug Conjugate: Pharmacokinetics in Mice, Rats, and NHP and Tumor/Tissue Distribution in Mice", Bioconjugate Chemistry, 2015, vol. 26, No. 11, pp. 2223-2232.
P.Sapra et al., "Long-term Tumor Regression Induced by an Antibody-Drug Conjugate That Targes 5T4, an Oncofetal Antigen Expressed on Tumor-Initiating Cells", Molecular Cancer Therapeutics, 2012, vol. 12, No. 1, pp. 38-47.
McKay Brown et al., "Tolerance to single, but not multiple, amino acid replacements in antibody V-H CDR2: A means of minimizing B cell wastage from somatic hypermutation?", The Journal of Immunology, 1996, vol. 156, No. 9, pp. 3285-3291.
Wark K L et al., "Latest technologies for the enhancement of antibody affinity", Advanced Drug Delivery Reviews, Elsevier, 2006, vol. 58, No. 5-6, pp. 657-670.

(Continued)

*Primary Examiner* — Mark Halvorson
*Assistant Examiner* — Dennis J Sullivan
(74) *Attorney, Agent, or Firm* — Banner & Witcoff, Ltd.

(57) ABSTRACT

The present invention provides a humanized anti-TPBG antibody, a preparation method therefor, a conjugate thereof, and applications. The humanized anti-TPBG antibody comprises: (a), a framework region comprising a residue of a human antibody framework region; and (b) one or more CDRs of a light-chain variable region as shown in the SEQ ID NO:4 or 8 or one or more CDRs of a heavy-chain variable region as shown in the SEQ ID NO:2 or 6.

20 Claims, 24 Drawing Sheets
Specification includes a Sequence Listing.

(56) References Cited

OTHER PUBLICATIONS

Mathieu Dondelinger et al., "Understanding the Significance and Implications of Antibody Numbering and Antigen-Binding Surface/Residue Definition", Frontiers in Immunology, 2018, vol. 9, pp. 1-15.
Extended European search report issued the counterpart European application No. 18781311.8 dated Feb. 25, 2020.
May 31, 2022 (JP) First Office Action issued in Japanese Patent Application No. 2019-554774.

* cited by examiner

Figure 3

| | 1 | 2 | 3 | 4 | 5 | 6 | 7 | 8 | 9 | 0 |
|---|---|---|---|---|---|---|---|---|---|---|
| | 1234567890 | 1234567890 | 123456789a bcde8901--23 | 4567890 | 12345678 | 9012345678 | 9012345678 | 90123456789 01234567890 | 1234567890 | 1234567 |
| c12B12.VK | DIVLTQSPASLAVSLGQRATIS | CRASQSVRSSYT | LMHWYQQKPGQPPKLLIK | YASNLES | GVPARFSGS | GSGTDFTLNI | HPVEDEDTATYYC | QHSWEIPLT | FGAGTKLELK |
| h12B12.VK.2 | DIVMTQTPLSLSVTPGQPASIS | CRASQSVRSSYT | LMHWYLQKPGQPPRLLIY | YASNLES | GVPDRFSGS | GSGTDFTLKI | SRVEAEDVGVYYC | QHSWEIPLT | FGQGTKLEIK |
| h12B12.VK.2a | DIVMTQTPLSLSVTPGQPASIS | CRASQSVRSSYT | LMHWYLQKPGQPPRLLIY | YASNLES | GVPDRFSGS | GSGTDFTLKI | SRVEAEDVGVYYC | QHSWEIPLT | FGQGTKLEIK |
| hJ/GK2 | DIVMTQTPLSLSVTPGQPASIS | CRSSQSLLHSNGYNYLD | WYLQKPGQPPRLLIY | LGSNRAS | GVPDRFSGS | GSGTDFTLKI | SRVEAEDVGVYYC | MQALQTPFT | --------- FGQGTKLEIK |

SEQUENCE LISTING

<160> NUMBER OF SEQ ID NOS: 46

<210> SEQ ID NO 1
<211> LENGTH: 360
<212> TYPE: DNA
<213> ORGANISM: Mus musculus

<400> SEQUENCE: 1

```
gatgtgcagc tggtggagtc tgggggaggc ttagtgcagc ctggagggtc ccggaaactc      60
tcctgtgcag cctctggatt cactttcagt aactttggaa tgcactgggt tcgtcaggct     120
ccagagaagg ggctggagtg ggtcgcatac attagtagtg gtagtacttc cttctactat     180
gcagacaccg tgaagggccg attcaccatc tccagagaca atcccaagaa caccctgttc     240
ctgcaaatga ccagtctaag gtctgaggac acggccatgt attactgttc aagaacgaat     300
```

```
tcattactac gaggattctt cgatgcctgg ggcgcaggga ccacggtcac cgtctcctca    360
```

<210> SEQ ID NO 2
<211> LENGTH: 120
<212> TYPE: PRT
<213> ORGANISM: Mus musculus

<400> SEQUENCE: 2

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asn Phe
            20                  25                  30

Gly Met His Trp Val Arg Gln Ala Pro Glu Lys Gly Leu Glu Trp Val
        35                  40                  45

Ala Tyr Ile Ser Ser Gly Ser Thr Ser Phe Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ser Arg Thr Asn Ser Leu Leu Arg Gly Phe Phe Asp Ala Trp Gly Ala
            100                 105                 110

Gly Thr Thr Val Thr Val Ser Ser
        115                 120
```

<210> SEQ ID NO 3
<211> LENGTH: 333
<212> TYPE: DNA
<213> ORGANISM: Mus musculus

<400> SEQUENCE: 3

```
gacattgtcc tgacacagtc tcctgcttcc ttagctgtat ctctggggca gagggccacc    60
atctcatgca gggccagcca agtgtcagt tcatctagtt atacttattt gcactggtac    120
caacagaaac caggacagcc acccaaactc ctcatcaagt ctgcatccaa cctagaatct    180
ggggtccctg ccaggttcag tggcactggg tctgggacag acttcaccct caacatacat    240
cctgtggagg aggaggatac tgcaacatat tactgtcagc acagttggga gattccactc    300
acgttcggtg ctgggaccaa gttggagctg aaa                                333
```

<210> SEQ ID NO 4
<211> LENGTH: 111
<212> TYPE: PRT
<213> ORGANISM: Mus musculus

<400> SEQUENCE: 4

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Ser
            20                  25                  30

Ser Tyr Thr Tyr Leu His Trp Tyr Gln Gln Lys Pro Gly Gln Pro Pro
        35                  40                  45

Lys Leu Leu Ile Lys Ser Ala Ser Asn Leu Glu Ser Gly Val Pro Ala
    50                  55                  60

Arg Phe Ser Gly Thr Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
```

85                  90                  95
Glu Ile Pro Leu Thr Phe Gly Ala Gly Thr Lys Leu Glu Leu Lys
            100                 105                 110

<210> SEQ ID NO 5
<211> LENGTH: 360
<212> TYPE: DNA
<213> ORGANISM: Mus musculus

<400> SEQUENCE: 5
gatgtacaac tggtggaatc tgggggaggc ttagtgaggc ctggagggtc cctgaaactc      60
tcctgtgcag cctccggatt cactttcagt aactatgtca tgtcttgggc tcgccagtct     120
ccagagaaga ggctggagtg ggtcgcagaa attagtactg gtgggagtca cactactat      180 tcagacactg tgacgggccg atttaccatc tccagagaca tgccaagaa agccctatac      240 ctggaaatga gcagtctgag gtctgaggac acggccatat attattgtat tatgttttac     300
tacggtagta gctattctat ggactactgg ggtcaaggaa cctcagtcac cgtctcctca     360

<210> SEQ ID NO 6
<211> LENGTH: 120
<212> TYPE: PRT
<213> ORGANISM: Mus musculus

<400> SEQUENCE: 6

Asp Val Gln Leu Val Glu Ser Gly Gly Gly Leu Val Arg Pro Gly Gly
1               5                   10                  15

Ser Leu Lys Leu Ser Cys Ala Ala Ser Gly Phe Thr Phe Ser Asn Tyr
            20                  25                  30

Val Met Ser Trp Ala Arg Gln Ser Pro Glu Lys Arg Leu Glu Trp Val
        35                  40                  45

Ala Glu Ile Ser Thr Gly Gly Ser His Thr Tyr Tyr Ser Asp Thr Val
    50                  55                  60

Thr Gly Arg Phe Thr Ile Ser Arg Asp Asn Ala Lys Lys Ala Leu Tyr
65                  70                  75                  80

Leu Glu Met Ser Ser Leu Arg Ser Glu Asp Thr Ala Ile Tyr Tyr Cys
                85                  90                  95

Ile Met Phe Tyr Tyr Gly Ser Ser Tyr Ser Met Asp Tyr Trp Gly Gln
            100                 105                 110

Gly Thr Ser Val Thr Val Ser Ser
        115                 120

<210> SEQ ID NO 7
<211> LENGTH: 321
<212> TYPE: DNA
<213> ORGANISM: Mus musculus

<400> SEQUENCE: 7
gatatccaga tgacacagag tacatcctcc ctgtctgcct ctctgggaga cagaatcacc      60
atcagttgca gggcaagtca ggacattagg aattatttaa actggtatca gcagaaacca     120
gatgggactg ttaaactcct gatctaccac acatcaagat tacactcagg agtcccatca     180
aggttcagtg gcagtgggtc tggcacagat tattctctca ccattagtaa cctgaacaa      240 gaagatattg ccacttattt ttgccaacag ggtgatacgc ttccgctcac gttcggtgcc     300
gggaccaggc tggagctgaa a                                                321

<210> SEQ ID NO 8

```
<211> LENGTH: 107
<212> TYPE: PRT
<213> ORGANISM: Mus musculus

<400> SEQUENCE: 8

Asp Ile Gln Met Thr Gln Ser Thr Ser Ser Leu Ser Ala Ser Leu Gly
1               5                   10                  15

Asp Arg Ile Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Leu
                85                  90                  95

Thr Phe Gly Ala Gly Thr Arg Leu Glu Leu Lys
            100                 105

<210> SEQ ID NO 9
<211> LENGTH: 109
<212> TYPE: PRT
<213> ORGANISM: Homo sapiens

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Trp Gly Gln Gly Thr Thr Val Thr Val Ser Ser
            100                 105

<210> SEQ ID NO 10
<211> LENGTH: 109
<212> TYPE: PRT
<213> ORGANISM: Homo sapiens

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105

<210> SEQ ID NO 11
<211> LENGTH: 104
<212> TYPE: PRT
<213> ORGANISM: Homo sapiens

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Phe Gly
                85                  90                  95

Gln Gly Thr Lys Leu Glu Ile Lys
            100

<210> SEQ ID NO 12
<211> LENGTH: 103
<212> TYPE: PRT
<213> ORGANISM: Homo sapiens

<400> SEQUENCE: 12

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gly Gln
                85                  90                  95

Gly Thr Lys Leu Glu Ile Lys
            100

<210> SEQ ID NO 13
<211> LENGTH: 109
<212> TYPE: PRT
<213> ORGANISM: Homo sapiens

<400> SEQUENCE: 13

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val

```
                    35                  40                  45
Ser Tyr Ile Ser Ser Gly Ser Thr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gln Gly Thr Val Thr Val Ser Ser
            100                 105

<210> SEQ ID NO 14
<211> LENGTH: 98
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Phe Gly Gln Gly Thr Arg Leu Glu
                 85                  90                  95

Ile Lys

<210> SEQ ID NO 15
<211> LENGTH: 360
<212> TYPE: DNA
<213> ORGANISM: Artificial Sequence
<220> FEATURE:
<223> OTHER INFORMATION: VH of antibody, human-mouse chimeric mutant

<400> SEQUENCE: 15
gaggtgcagc tggtggaatc aggaggagga ctggtgcagc caggaggatc tctgagactg      60
tcttgcgccg ccagcggctt acattcagc aacttcggca tgcattgggt ccggcaggca     120
ccaggaaagg gcctggagtg ggtgtcctat atcagcagcg gcagcaccag cttctactac     180
gccgacaccg tgaagggcag attcaccatc agccgggaca cgccaagaa cagcctgtac     240 ctgcagatga acagcctgcg cgacgaggat accgccgtgt actattgcgc caggaccaac     300
agcctgctga ggggattctt cgacgcttgg ggacagggca acagtgac agtgtccagc     360

<210> SEQ ID NO 16
<211> LENGTH: 120
<212> TYPE: PRT
<213> ORGANISM: Artificial Sequence
<220> FEATURE:
<223> OTHER INFORMATION: VH of antibody, human-mouse chimeric mutant

<400> SEQUENCE: 16

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Phe
             20                  25                  30
```

```
Gly Met His Trp Val Arg Gln Ala Pro Gly Lys Gly Leu Glu Trp Val
            35                  40                  45

Ser Tyr Ile Ser Ser Gly Ser Thr Ser Phe Tyr Tyr Ala Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Thr Asn Ser Leu Leu Arg Gly Phe Phe Asp Ala Trp Gly Gln
                100                 105                 110

Gly Thr Thr Val Thr Val Ser Ser
            115                 120

<210> SEQ ID NO 17
<211> LENGTH: 360
<212> TYPE: DNA
<213> ORGANISM: Artificial Sequence
<220> FEATURE:
<223> OTHER INFORMATION: VH of antibody, human-mouse chimeric mutant

<400> SEQUENCE: 17
gaggtgcagc tggtggaatc aggaggagga ctggtgcagc caggaggatc tctgagactg      60
tcttgcgccg ccagcggctt tacattcagc aacttcggca tgcattgggt ccggcaggca     120
ccaggaaagg gcctggagtg ggtgtcctat atcagcagcg gcagcaccag cttctactac     180
gccgacaccg tgaagggcag attcaccatc agccgggaca cgccaagaa cagcctgtac      240 ctgcagatga acagcctgcg cgacgaggat accgccgtgt actattgcag ccggaccaac     300
agcctgctga ggggattctt cgacgcttgg ggacagggca acagtgac agtgtccagc      360

<210> SEQ ID NO 18
<211> LENGTH: 120
<212> TYPE: PRT
<213> ORGANISM: Artificial Sequence
<220> FEATURE:
<223> OTHER INFORMATION: VH of antibody, human-mouse chimeric mutant

<400> SEQUENCE: 18

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Phe
             20                  25                  30

Gly Met His Trp Val Arg Gln Ala Pro Gly Lys Gly Leu Glu Trp Val
            35                  40                  45

Ser Tyr Ile Ser Ser Gly Ser Thr Ser Phe Tyr Tyr Ala Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ser Arg Thr Asn Ser Leu Leu Arg Gly Phe Phe Asp Ala Trp Gly Gln
                100                 105                 110

Gly Thr Thr Val Thr Val Ser Ser
            115                 120

<210> SEQ ID NO 19
<211> LENGTH: 360
<212> TYPE: DNA
```

<213> ORGANISM: Artificial Sequence
<220> FEATURE:
<223> OTHER INFORMATION: VH of antibody, human-mouse chimeric mutant

<400> SEQUENCE: 19

```
gaggtgcagc tggtggaatc aggaggagga ctggtgcagc caggaggatc tctgagactg    60
tcttgcgccg ccagcggctt tacattcagc aacttcggca tgcattgggt ccggcaggct   120
ccaggaaagg gactcgagtg gtggcttac atcagcagcg gcagcaccag cttctactac    180
gccgacaccg tgaagggcag attcaccatc agccgggaca cgccaagaa cagcctgtac    240
ctgcagatga acagcctgcg cgacgaggat accgccgtgt actattgcag ccggaccaac    300
agcctgctga gggattctt cgacgcttgg ggacagggca acagtgac agtgtccagc    360
```

<210> SEQ ID NO 20
<211> LENGTH: 120
<212> TYPE: PRT
<213> ORGANISM: Artificial Sequence
<220> FEATURE:
<223> OTHER INFORMATION: VH of antibody, human-mouse chimeric mutant

<400> SEQUENCE: 20

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Phe
            20                  25                  30
Gly Met His Trp Val Arg Gln Ala Pro Gly Lys Gly Leu Glu Trp Val
        35                  40                  45
Ala Tyr Ile Ser Ser Gly Ser Thr Ser Phe Tyr Tyr Ala Asp Thr Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Asp Glu Asp Thr Ala Val Tyr Tyr Cys
                85                  90                  95
Ser Arg Thr Asn Ser Leu Leu Arg Gly Phe Phe Asp Ala Trp Gly Gln
            100                 105                 110
Gly Thr Thr Val Thr Val Ser Ser
        115                 120
```

<210> SEQ ID NO 21
<211> LENGTH: 360
<212> TYPE: DNA
<213> ORGANISM: Artificial Sequence
<220> FEATURE:
<223> OTHER INFORMATION: VH of antibody, human-mouse chimeric mutant

<400> SEQUENCE: 21

```
gaggtgcagc tggtggaatc aggaggagga gtggtgcagc aggcagatc tctgagactg    60
tcttgcgccg ccagcggctt tacattcagc aacttcggca tgcattgggt ccggcaggct   120
ccaggaaagg gactcgagtg gtggcttac atcagcagcg gcagcaccag cttctactac    180
gccgacaccg tgaagggcag attcaccatc agccgggaca cagcaagaa caccctgtac    240
ctgcagatga acagcctgag gccgaggat accgcagtgt actattgcgc ccggaccaac    300
agcctgctga gaggcttctt cgacgcttgg ggacagggca acagtgac agtgtccagc    360
```

<210> SEQ ID NO 22
<211> LENGTH: 120
<212> TYPE: PRT
<213> ORGANISM: Artificial Sequence

```
<220> FEATURE:
<223> OTHER INFORMATION: VH of antibody, human-mouse chimeric mutant

<400> SEQUENCE: 22

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Tyr Ile Ser Ser Gly Ser Thr Ser Phe Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asn Ser Leu Leu Gly Phe Phe Asp Ala Trp Gly Gln
            100                 105                 110

Gly Thr Thr Val Thr Val Ser Ser
        115                 120

<210> SEQ ID NO 23
<211> LENGTH: 360
<212> TYPE: DNA
<213> ORGANISM: Artificial Sequence
<220> FEATURE:
<223> OTHER INFORMATION: VH of antibody, human-mouse chimeric mutant

<400> SEQUENCE: 23
gaggtgcagc tggtggaatc aggaggagga gtggtgcagc caggcagatc tctgagactg        60
tcttgcgccg ccagcggctt tacattcagc aacttcggca tgcattgggt ccggcaggct       120
ccaggaaagg gactcgagtg ggtggcttac atcagcagcg gcagcaccag cttctactac       180
gccgacaccg tgaagggcag attcaccatc agccgggaca acagcaagaa caccctgtac       240
ctgcagatga acagcctgag ggccgaggat accgccgtgt actattgcag ccggaccaac       300
agcctgctga ggggattctt cgacgcttgg ggacagggca acagtgac agtgtccagc       360

<210> SEQ ID NO 24
<211> LENGTH: 120
<212> TYPE: PRT
<213> ORGANISM: Artificial Sequence
<220> FEATURE:
<223> OTHER INFORMATION: VH of antibody, human-mouse chimeric mutant

<400> SEQUENCE: 24

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Tyr Ile Ser Ser Gly Ser Thr Ser Phe Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ser Arg Thr Asn Ser Leu Leu Arg Gly Phe Phe Asp Ala Trp Gly Gln
            100                 105                 110

Gly Thr Thr Val Thr Val Ser Ser
        115                 120

<210> SEQ ID NO 25
<211> LENGTH: 333
<212> TYPE: DNA
<213> ORGANISM: Artificial Sequence
<220> FEATURE:
<223> OTHER INFORMATION: VL of antibody, human-mouse chimeric mutant

<400> SEQUENCE: 25
gacatcgtga tgacccagag cccagacagc ctggcagtgt ctctgggaga gagagccaca     60
atcaattgcc gggcctctca gagcgtgtcc agcagcagct acacctacct gcattggtat    120
cagcagaaac aggccagcc tcctaagctg ctgatctaca gcgccagcaa cctggagagc    180
ggagtgccag acagattcag cggcagcgga agcggaaccg acttcaccct gaccatcagc    240
tctctgcagg cagaagacgt ggccgtgtac tactgccagc actcttggga gatccctctg    300
accttcggcc agggcacaaa gctggagatc aag                                 333

<210> SEQ ID NO 26
<211> LENGTH: 111
<212> TYPE: PRT
<213> ORGANISM: Artificial Sequence
<220> FEATURE:
<223> OTHER INFORMATION: VL of antibody, human-mouse chimeric mutant

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Ser
            20                  25                  30

Ser Tyr Thr Tyr Leu His Trp Tyr Gln Gln Lys Pro Gly Gln Pro Pro
        35                  40                  45

Lys Leu Leu Ile Tyr Ser Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 27
<211> LENGTH: 333
<212> TYPE: DNA
<213> ORGANISM: Artificial Sequence
<220> FEATURE:
<223> OTHER INFORMATION: VL of antibody, human-mouse chimeric mutant

<400> SEQUENCE: 27
gacatcgtgc tgacccagag cccagactct ctggcagtgt ctctgggaga gagagccaca     60
atcaattgcc gggcctctca gagcgtgtcc agcagcagct acacctacct gcattggtat    120
cagcagaaac aggccagcc tcctaagctg ctgatcaaga gcgccagcaa cctggagagc    180
ggagtgccag acagattcag cggcagcgga agcggaaccg acttcaccct gaccatcagc    240
tctctgcagg cagaagacgt ggccgtgtac tactgccagc actcttggga gatccctctg    300
```
accttcggcc agggcacaaa gctggagatc aag         333

<210> SEQ ID NO 28
<211> LENGTH: 111
<212> TYPE: PRT
<213> ORGANISM: Artificial Sequence
<220> FEATURE:
<223> OTHER INFORMATION: VL of antibody, human-mouse chimeric mutant

<400> SEQUENCE: 28

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Ser Ser Ser
            20                  25                  30

Ser Tyr Thr Tyr Leu His Trp Tyr Gln Gln Lys Pro Gly Gln Pro Pro
        35                  40                  45

Lys Leu Leu Ile Lys Ser Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 29
<211> LENGTH: 333
<212> TYPE: DNA
<213> ORGANISM: Artificial Sequence
<220> FEATURE:
<223> OTHER INFORMATION: VL of antibody, human-mouse chimeric mutant

<400> SEQUENCE: 29
gacatcgtga tgacccagac ccctctgtcc ctgtctgtga caccaggaca gccagctagc    60
atctcttgca gagccagcca gagcgtgtcc agcagcagct acacctacct gcattggtat   120
ctgcagaagc caggacagcc tcctcagctg ctgatctaca gcgccagcaa cctggagagc   180
ggcgtgccag atagattcag cggaagcgga agcggcaccg acttcaccct gaagatcagc   240
agagtggagg cagaagacgt gggcgtgtac tactgccagc actcttggga gatccctctg   300
accttcggcc agggcacaaa gctggagatc aag                               333

<210> SEQ ID NO 30
<211> LENGTH: 111
<212> TYPE: PRT
<213> ORGANISM: Artificial Sequence
<220> FEATURE:
<223> OTHER INFORMATION: VL of antibody, human-mouse chimeric mutant

<400> SEQUENCE: 30

Asp Ile Val Met Thr Gln Thr Pro Leu Ser Leu Ser Val Thr Pro Gly
1               5                   10                  15

Gln Pro Ala Ser Ile Ser Cys Arg Ala Ser Gln Ser Val Ser Ser Ser
            20                  25                  30

Ser Tyr Thr Tyr Leu His Trp Tyr Leu Gln Lys Pro Gly Gln Pro Pro
        35                  40                  45

Gln Leu Leu Ile Tyr Ser Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

```
Arg Val Glu Ala Glu Asp Val Gly Val Tyr Tyr Cys Gln His Ser Trp
            85                   90                  95

Glu Ile Pro Leu Thr Phe Gly Gln Gly Thr Lys Leu Glu Ile Lys
           100                 105                 110

<210> SEQ ID NO 31
<211> LENGTH: 333
<212> TYPE: DNA
<213> ORGANISM: Artificial Sequence
<220> FEATURE:
<223> OTHER INFORMATION: VL of antibody, human-mouse chimeric mutant

<400> SEQUENCE: 31
gacatcgtgc tgacccagac ccctctgtct ctgagcgtga caccaggaca gccagcttct    60
atctcttgca gagccagcca gagcgtgtcc agcagcagct acacctacct gcattggtat   120
ctgcagaagc caggacagcc tcctcagctg ctgatcaaga gcgccagcaa cctggagagc   180
ggcgtgccag atagattcag cggaagcgga agcggcaccg acttcaccct gaagatcagc   240
agagtggagg cagaagacgt gggcgtgtac tactgccagc actcttggga gatccctctg   300
accttcggcc agggcacaaa gctggagatc aag                                333

<210> SEQ ID NO 32
<211> LENGTH: 111
<212> TYPE: PRT
<213> ORGANISM: Artificial Sequence
<220> FEATURE:
<223> OTHER INFORMATION: VL of antibody, human-mouse chimeric mutant

<400> SEQUENCE: 32

Asp Ile Val Leu Thr Gln Thr Pro Leu Ser Leu Ser Val Thr Pro Gly
1               5                   10                  15

Gln Pro Ala Ser Ile Ser Cys Arg Ala Ser Gln Ser Val Ser Ser Ser
            20                  25                  30

Ser Tyr Thr Tyr Leu His Trp Tyr Leu Gln Lys Pro Gly Gln Pro Pro
        35                  40                  45

Gln Leu Leu Ile Lys Ser Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
            85                  90                  95

Glu Ile Pro Leu Thr Phe Gly Gln Gly Thr Lys Leu Glu Ile Lys
           100                 105                 110

<210> SEQ ID NO 33
<211> LENGTH: 360
<212> TYPE: DNA
<213> ORGANISM: Artificial Sequence
<220> FEATURE:
<223> OTHER INFORMATION: VH of antibody, human-mouse chimeric mutant

<400> SEQUENCE: 33
gaggtgcagc tggtggaatc aggaggagga ctggtgaagc caggcggatc tctgagactg    60
tcttgcgccg ccagcggctt acattcagc aactacgtga tgtcttggat ccggcaggca   120
ccaggaaagg gactggagtg ggtgtccgaa atcagcaccg gcggaagcca cacctactac   180
agcgacaccg tgaccggaag gttcaccatc agccgggaca cgccaagaa cagcctgtac   240 ctgcagatga acagcctgcg cgccgaagat accgccgtgt actattgcgc ccggttctac   300
```
tacggcagca gctacagcat ggactattgg ggccagggaa ccaccgtgac agtgtcttct    360

```
<210> SEQ ID NO 34
<211> LENGTH: 120
<212> TYPE: PRT
<213> ORGANISM: Artificial Sequence
<220> FEATURE:
<223> OTHER INFORMATION: VH of antibody, human-mouse chimeric mutant
```

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Val Met Ser Trp Ile Arg Gln Ala Pro Gly Lys Gly Leu Glu Trp Val
        35                  40                  45

Ser Glu Ile Ser Thr Gly Gly Ser His Thr Tyr Tyr Ser Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Tyr Gly Ser Ser Tyr Ser Met Asp Tyr Trp Gly Gln
            100                 105                 110

Gly Thr Thr Val Thr Val Ser Ser
        115                 120

```
<210> SEQ ID NO 35
<211> LENGTH: 360
<212> TYPE: DNA
<213> ORGANISM: Artificial Sequence
<220> FEATURE:
<223> OTHER INFORMATION: VH of antibody, human-mouse chimeric mutant
```

<400> SEQUENCE: 35
gaggtgcagc tggtggaatc aggaggagga ctggtgaagc caggcggatc tctgagactg     60
tcttgcgccg ccagcggctt tacattcagc aactacgtga tgtcttggat ccggcaggca    120
ccaggaaagg gactggagtg ggtgtccgaa atcagcaccg gcggaagcca cactactac    180 agcgacaccg tgaccggaag gttcaccatc agccgggaca cgccaagaa cagcctgtac    240 ctgcagatga acagcctgag agccgaggac accgccgtgt actattgcat catgttctac    300
tacggcagca gctacagcat ggactattgg ggccagggaa ccaccgtgac agtgtcttct    360

```
<210> SEQ ID NO 36
<211> LENGTH: 120
<212> TYPE: PRT
<213> ORGANISM: Artificial Sequence
<220> FEATURE:
<223> OTHER INFORMATION: VH of antibody, human-mouse chimeric mutant
```

<400> SEQUENCE: 36

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Val Met Ser Trp Ile Arg Gln Ala Pro Gly Lys Gly Leu Glu Trp Val
        35                  40                  45

Ser Glu Ile Ser Thr Gly Gly Ser His Thr Tyr Tyr Ser Asp Thr Val

```
                50                  55                  60
Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ile Met Phe Tyr Tyr Gly Ser Ser Tyr Ser Met Asp Tyr Trp Gly Gln
                100                 105                 110

Gly Thr Thr Val Thr Val Ser Ser
            115                 120

<210> SEQ ID NO 37
<211> LENGTH: 360
<212> TYPE: DNA
<213> ORGANISM: Artificial Sequence
<220> FEATURE:
<223> OTHER INFORMATION: VH of antibody, human-mouse chimeric mutant

<400> SEQUENCE: 37
gaggtgcagc tggtggaatc aggaggagga ctggtgaagc caggcggatc tctgagactg      60
tcttgcgccg ccagcggctt tacattcagc aactacgtga tgtcttggat ccggcaggca     120
ccaggaaagg gactcgagtg ggtggcagaa atcagcaccg gaggcagcca cacctactac     180
agcgacaccg tgaccggaag gttcaccatc agccgggaca cgccaagaa gagcctgtac      240 ctgcagatga acagcctgag agccgaggac accgccgtgt actattgcat catgttctac     300
tacggcagca gctacagcat ggactattgg ggccagggaa ccaccgtgac agtgtcttct     360

<210> SEQ ID NO 38
<211> LENGTH: 120
<212> TYPE: PRT
<213> ORGANISM: Artificial Sequence
<220> FEATURE:
<223> OTHER INFORMATION: VH of antibody, human-mouse chimeric mutant

<400> SEQUENCE: 38

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Tyr
                 20                  25                  30

Val Met Ser Trp Ile Arg Gln Ala Pro Gly Lys Gly Leu Glu Trp Val
             35                  40                  45

Ala Glu Ile Ser Thr Gly Gly Ser His Thr Tyr Tyr Ser Asp Thr Val
         50                  55                  60

Thr Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                 85                  90                  95

Ile Met Phe Tyr Tyr Gly Ser Ser Tyr Ser Met Asp Tyr Trp Gly Gln
                100                 105                 110

Gly Thr Thr Val Thr Val Ser Ser
            115                 120

<210> SEQ ID NO 39
<211> LENGTH: 360
<212> TYPE: DNA
<213> ORGANISM: Artificial Sequence
<220> FEATURE:
<223> OTHER INFORMATION: VH of antibody, human-mouse chimeric mutant

<400> SEQUENCE: 39
```

```
gaggtgcagc tggtggaatc aggaggagga ctggtgaagc caggcggatc tctgagactg     60
tcttgcgccg ccagcggctt tacattcagc aactacgtga tgtcttgggc ccggcaggca    120
ccaggaaaga gactcgagtg ggtggccgaa atcagcaccg gaggcagcca cacctactac    180
agcgacaccg tgaccggaag gttcaccatc agccgggaca cgccaagaa  gagcctgtac    240 ctgcagatga acagcctgag agccgaggac accgccgtgt actattgcat catgttctac    300
tacggcagca gctacagcat ggactattgg ggccagggaa ccaccgtgac agtgtcttct    360
```

<210> SEQ ID NO 40
<211> LENGTH: 120
<212> TYPE: PRT
<213> ORGANISM: Artificial Sequence
<220> FEATURE:
<223> OTHER INFORMATION: VH of antibody, human-mouse chimeric mutant

<400> SEQUENCE: 40

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
            20                  25                  30

Val Met Ser Trp Ala Arg Gln Ala Pro Gly Lys Arg Leu Glu Trp Val
        35                  40                  45

Ala Glu Ile Ser Thr Gly Gly Ser His Thr Tyr Tyr Ser Asp Thr Val
    50                  55                  60

Thr Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ile Met Phe Tyr Tyr Gly Ser Ser Tyr Ser Met Asp Tyr Trp Gly Gln
            100                 105                 110

Gly Thr Thr Val Thr Val Ser Ser
        115                 120
```

<210> SEQ ID NO 41
<211> LENGTH: 321
<212> TYPE: DNA
<213> ORGANISM: Artificial Sequence
<220> FEATURE:
<223> OTHER INFORMATION: VL of antibody, human-mouse chimeric mutant

<400> SEQUENCE: 41

```
gacatccaga tgacccagag ccctagcagc ctgagcgcca gcgtgggaga tagagtgacc     60
atcacctgta gagccagcca ggacatccgg aactacctga attggtatca gcagaagccc    120
ggcaaggccc ctaagctgct gatctaccac accagcagac tgcacagcgg agtgccttct    180
agattcagcg gcagcggaag cggcacagat ttcaccttca ccatcagcag cctgcagccc    240
gaggacatcg ccacctacta ttgccagcag ggcgacacac tgcctctgac ctttggacag    300
ggaaccaggc tggagatcaa g                                              321
```

<210> SEQ ID NO 42
<211> LENGTH: 107
<212> TYPE: PRT
<213> ORGANISM: Artificial Sequence
<220> FEATURE:
<223> OTHER INFORMATION: VL of antibody, human-mouse chimeric mutant

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
                35                  40                  45

Tyr His Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Thr Leu Pro Leu
                85                  90                  95

Thr Phe Gly Gln Gly Thr Arg Leu Glu Ile Lys
            100                 105

<210> SEQ ID NO 43
<211> LENGTH: 321
<212> TYPE: DNA
<213> ORGANISM: Artificial Sequence
<220> FEATURE:
<223> OTHER INFORMATION: VL of antibody, human-mouse chimeric mutant

<400> SEQUENCE: 43
gacatccaga tgacccagag ccctagcagc ctgagcgcca gcgtgggaga tagagtgacc      60
atcacctgta gagccagcca ggacatccgg aactacctga attggtatca gcagaagccc    120
ggcaaggccc ctaagctgct gatctaccac accagcagac tgcacagcgg agtgccttct    180
agattcagcg gcagcggaag cggcacagat tacaccttca ccatcagcag cctgcagccc    240
gaggacatcg ccacctacta ttgccagcag ggcgacacac tgcctctgac ctttggacag    300
ggaaccaggc tggagatcaa g                                              321

<210> SEQ ID NO 44
<211> LENGTH: 107
<212> TYPE: PRT
<213> ORGANISM: Artificial Sequence
<220> FEATURE:
<223> OTHER INFORMATION: VL of antibody, human-mouse chimeric mutant

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
                35                  40                  45

Tyr His Thr Ser Arg Leu His Ser Gly Val Pro Ser Arg Phe Ser Gly
        50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asp Thr Leu Pro Leu
                85                  90                  95

Thr Phe Gly Gln Gly Thr Arg Leu Glu Ile Lys
            100                 105

<210> SEQ ID NO 45
<211> LENGTH: 321
<212> TYPE: DNA
<213> ORGANISM: Artificial Sequence

```
<220> FEATURE:
<223> OTHER INFORMATION: VL of antibody, human-mouse chimeric mutant

<400> SEQUENCE: 45
gacatccaga tgacccagag ccctagcagc ctgagcgcca gcgtgggaga tagagtgacc    60
atcacctgta gagccagcca ggacatccgg aactacctga attggtatca gcagaagccc   120
ggcaagaccg tgaagctgct gatctaccac accagcagac tgcacagcgg agtgccttct   180
agattcagcg gcagcggaag cggcacagat tacaccttca ccatcagcag cctgcagccc   240
gaggacatcg ccacctactt ttgccagcag ggcgataccc tgcctctgac ctttggacag   300
ggaaccaggc tggagatcaa g                                             321

<210> SEQ ID NO 46
<211> LENGTH: 107
<212> TYPE: PRT
<213> ORGANISM: Artificial Sequence
<220> FEATURE:
<223> OTHER INFORMATION: VL of antibody, human-mouse chimeric mutant

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Gln Gln Gly Asp Thr Leu Pro Leu
                85                  90                  95

Thr Phe Gly Gln Gly Thr Arg Leu Glu Ile Lys
            100                 105
```

HUMANIZED ANTI-TPBG ANTIBODY, PREPARATION METHOD THEREFOR, CONJUGATE THEREOF, AND APPLICATIONS

RELATED APPLICATION DATA

This application is a National Stage Application under 35 U.S.C. 371 of co-pending PCT application number PCT application no. PCT/CN2018/081853, filed Apr. 4, 2018; which claims the benefit of Chinese Patent Application number CN201710218524.1, filed Apr. 5, 2017, each of which are hereby incorporated by reference in their entireties.

FIELD OF THE INVENTION

The present invention relates to the field of antibody, specifically relates to a humanized anti-TPBG antibody and preparation method thereof, conjugates thereof and use thereof.

BACKGROUND

When comparing embryonic stem cell trophoblast and cancer cells, a cell surface molecule, trophoblast-specific glycoprotein (TPBG, also known as 5T4), is found to be a specific protein expressed by the embryonic trophoblast. Human TPBG protein has a molecular weight of about 72 kDa and contains 420 amino acids residues. The diversity of its N-terminal oligosaccharide structure can prevent protein hydrolysis and interact with other molecules in the process of signal transduction on plasma membrane. The TPBG protein includes a total of seven leucine-rich repeats (LRR), which can participate in protein-protein interactions.

Trophoblast is a special layer of embryonic stem cells between the placenta and the fetus, and TPBG is widely expressed in various types of trophoblast cells during embryonic development. Whereas TPBG has a limited expression by several kinds of epithelial cells in normal adult tissues, it can be detected in various types of cancer cells, e.g. uterine cancer, colon cancer, gastric cancer, ovarian cancer, oral cancer, prostate cancer, lung cancer or renal cancer. For colon cancer, gastric cancer or ovarian cancer, there is evidence that the high expression level of TPBG is related to the poor cure rate of cancer. In tissues of non-small cell lung carcinoma, renal cancer or pancreatic cancer, the expression rate of TPBG can be over 95%.

Many researches have shown that overexpression of TPBG can promote cell migration as well as avoid immune surveillance. Overexpression of TPBG in mouse fibroblasts induces the exhibition of spindle-like cell morphology and reduces cell adhesion. In normal mouse epithelial cells, TPBG is also found to inhibit the expression of epithelial cell cadherin (E-cadherin) and promote cell migration. However, the intracellular moiety of TPBG has the function of inhibiting the formation of cytoskeleton. Meanwhile, TPBG is associated with epithelial mesenchymal transition (EMT). As an early marker of embryonic stem cell development, TPBG increases the activity of intercellular protease, and interferes with the arrangement of actin cytoskeleton, thereby lowering the expression level of E-cadherin. Other studies discovered that the colocalization of TPBG and CXCR4 on plasma membrane can induce the binding of its ligand chemokine CXCL12 and promote the spread of inflammation and tumor. In TPBG-negative cells, the binding of CXCL12 to another receptor CXCR7 inhibits chemotaxis, facilitating cell growth and survival. Wnt/b-catenin signaling pathway plays a crucial role in development and cell regeneration, while TPBG inhibits Wnt signaling pathway through inhibition of the endocytosis of LRP6 and Wnt receptors, thus inhibiting cell adhesion and formation of cytoskeleton and facilitating migration and proliferation of tumor. There is also evidence that TPBG is involved in non-canonical Wnt pathways in cells of breast cancer and gastric cancer, as well as facilitating the metastasis and infiltration of cancer cells.

Monoclonal antibody is developing into new diagnostic and therapeutic drugs due to its advantages of targeting, specificity, selectivity and high affinity. However, early clinical trials revealed that the use of non-human derived monoclonal antibodies in human often results in severe immune responses due to human anti-mouse antibody (HAMA) and human anti-rat antibody (HARA) responses, leading to rapid clearance of antibodies. Therefore, antibodies with less immunogenicity were developed, including chimeric antibodies, humanized antibodies, and fully human antibodies. According to the degree of humanization, therapeutic monoclonal antibody drugs can be divided into four types: mouse derived antibody (non-human amino acid sequence), chimeric antibody (60% to 70% humanized amino acid sequence), CDR grafted antibody (90% to 95% humanized amino acid sequence) and fully human antibody (100% human amino acid sequence). As the degree of humanization increases, non-mouse monoclonal antibodies can alleviate human anti-mouse antibody responses (HAMA and HARA responses) during therapy, gradually eliminating the immunogenicity of heterologous antibodies, and maintaining high affinity for antigens. Meanwhile, the pharmacokinetics of the antibodies have been improved, and these antibody drugs have been largely used in the clinic for targeted therapy.

Antibody-drug conjugates are conjugates formed by coupling an antibody with a high potent small-molecule drug through a linker, which enables the highly toxic small-molecule drug to specifically recognize target protein on cancer cells, thereby specifically killing cancer cells. In the past 100 years, antibody-based immunotherapy and chemical drug-based chemotherapy have been the two major therapeutic strategies for cancer treatment in clinical practice. Antibodies target antigens overexpressed by tumor cells, and a variety of therapeutic monoclonal antibodies have achieved great clinical success. In clinical practice, although therapeutic antibodies have great targeting, the cytotoxicity of therapeutic antibodies are limited. Small molecule chemical drugs have an efficient cytotoxicity effects on cancer cells, but they also cause the same damage to non-cancer cells. Therefore, the clinical limitations of both antibody drugs and small molecule drugs have put forward new requirements for drug development. The new generation of antibody drug conjugates have achieved highly cytotoxic effects on cancer cells by delivering highly cytotoxic chemical drugs utilizing the binding specificity of antibody to its target cells. With the development of new chemical linker technology, antibody-drug conjugates emerged in clinical research in the late 1980s, and two commercial ADC drugs have approved by FDA till now.

The development of ADC drugs involves several aspects: the screening of drug targets, the preparation of recombinant antibodies, the development of linker techniques and screening and optimization of high cytotoxic chemical compounds.

As a protein specifically expressed by cancer cells, TPBG is an ideal candidate target for ADC drugs.

DETAILED DESCRIPTION OF THE INVENTION

The technical problem to be solved by present invention is to overcome the deficiency of lacking TPBG antibody and provide a humanized TPBG antibody with high affinity and specificity, a preparation method thereof and a use thereof. The present humanized TPBG antibody shows high affinity with TPBG protein. As the degree of humanization increases, the human anti-mouse antibody response (HAMA reaction) can be alleviated during the treatment of human body, and the immunogenicity of the heterologous antibody is gradually eliminated, improving the pharmacokinetics of antibodies while maintaining high affinity for antigens. The present invention also provides a conjugate of a pharmaceutically active ingredient comprising the humanized anti-TPBG antibody as described above and a small molecule compound with antitumor function coupled thereto. The conjugate is capable of internalizing cell and has a cytotoxicity effect on TPBG positive cells, thus can be used in the preparation of drugs such as anti-tumor drugs.

The present inventors obtained a lead antibody of the TPBG antibody by using a human derived TBPG protein or recombinant cell line overexpressing human derived TBPG protein as an immunogen, adapting conventional hybridoma preparation technique (Kohler and Milstein, Nature, 1975, 25:495) through a series of adjustments and improvements. Then, the TPBG antibody having high affinity with human TPBG protein was obtained by preliminarily production, purification and identification of the lead antibody. The amino acid sequence of the heavy chain variable region and the light chain variable region of the obtained mouse derived TPBG antibody has been identified by sequencing using molecular biological methods. The antigen binding CDR region of the mouse antibody (which has been well-analyzed) is grafted with the human antibody framework, forming a CDR-grafted antibody by remodeling its affinity. The CDR-grafted antibody maintains its specificity and most affinity, as well as completely eliminates the side effects of immunogenicity and cytotoxicity. The humanized TPBG antibody is coupled with a small-molecule compound such as MMAF to form a conjugate, which can be internalized to the cell and has an excellent cytotoxicity effect on TPBG positive cells.

The present invention provides a humanized anti-TPBG antibody, comprising:

(a) a framework region containing residues of a human antibody framework region; and (b) one or more CDRs of the light chain variable region set forth in SEQ ID NO: 4 or 8, or one or more CDRs of the heavy chain variable region set forth in SEQ ID NO: 2 or 6.

The present human antibody framework region comprises a heavy chain framework region and a light chain framework region, and the framework region residues of human antibody light chain comprise germ line O2, O12, DPK1 (O18), DPK2, DPK3, DPK4, DPK5, DPK6, DPK7, DPK8, DPK9, DPK10, DPK12 (A2), DPK13, DPK15, DPK16, DPK18, DPK19, DPK20, DPK21, DPK22, DPK23, DPK24 (B3), DPK25, DPK26 and DPK 28, especially FR1, FR2, FR3 region of these germ lines; and Jk1, Jk2, Jk3, Jk4 and JK5 of Jk fragments, especially FR4 region of these germ lines. The framework region residues of human antibody heavy chain may comprises germ lines DP4, DP7, DP8, DP9, DP10, DP31, DP33, DP35 (VH3-11), DP45, DP46, DP47, DP48, DP49 (VH3-30), DP50, DP51 (VH3-48), DP53, DP54, DP65, DP66, DP67, DP68 and DP69, especially FR1, FR2, FR3 region of these germ lines; and JH fragments JH1, JH2, JH3, JH4, JH4b, JH5 and JH6, especially the FR4 region encoded sequences of these lines, or the consensus sequences of the heavy chain framework regions. Such framework region sequences can be obtained from public DNA databases including germ lines sequences of antibody gene or published references. For example, germ line DNA sequences of the human heavy and light chain variable regions genes can be obtained from the "VBase" human germ line sequence database (www.mrcco8.com.ac.uk/vbase), and found in Kabat, E A et al., 1991. 'Sequences of Proteins of Immunological Interest', the 5th edition.

In a preferred embodiment of the invention, for the humanized anti-TPBG antibody, the CDR is a CDR of mouse antibody, selecting from one or more of the light chain variable region set forth in SEQ ID NO: 4 or 8, or one or more CDRs of the heavy chain variable region set forth in SEQ ID NO: 2 or 6. Preferably, the amino acid residue sequence of CDR1 of mouse-derived antibody heavy chain variable region consist of residues 31 to 35 of SEQ ID NO: 2; more preferably, the nucleotide sequence encoding the amino acid sequence of CDR1 in the heavy chain variable region of the mouse-derived antibody consist of nucleotides 91 to 105 of SEQ ID NO: 1;

The amino acid sequence of the CDR2 of the mouse-derived antibody heavy chain variable region consists of residues 50 to 66 of SEQ ID NO: 2; more preferably, the nucleotide sequence encoding the amino acid sequence of CDR2 in the heavy chain variable region of the mouse-derived antibody consists of nucleotides 148 to 198 of SEQ ID NO: 1;

The amino acid sequence of the CDR3 of the mouse-derived antibody heavy chain variable region consists of residues 99 to 109 of SEQ ID NO: 2; more preferably, the nucleotide sequence encoding the amino acid sequence of CDR3 in the heavy chain variable region of the mouse-derived antibody consists of nucleotides 295 to 327 of SEQ ID NO: 1;

The amino acid sequence of the CDR1 of the mouse-derived antibody light chain variable region consists of residues 24 to 38 of SEQ ID NO: 4; more preferably, the nucleotide sequence encoding the amino acid sequence of CDR1 in the light chain variable region of the mouse-derived antibody consists of nucleotides 70 to 114 of SEQ ID NO: 3;

The amino acid sequence of the CDR2 of the mouse-derived antibody light chain variable region consists of residues 54 to 60 of SEQ ID NO: 4; more preferably, the nucleotide sequence encoding the amino acid sequence of CDR2 in the light chain variable region of the mouse-derived antibody consists of nucleotides 160 to 180 of SEQ ID NO: 3;

The amino acid sequence of the CDR3 of the mouse-derived antibody light chain variable region consists of residues 93 to 101 of SEQ ID NO: 4; more preferably, the nucleotide sequence encoding the amino acid sequence of CDR3 in the light chain variable region of the mouse-derived antibody consists of nucleotides 277 to 303 of SEQ ID NO: 3;

Or, the amino acid sequence of the CDR1 of the mouse-derived antibody heavy chain variable region consists of residues 31 to 35 of SEQ ID NO: 6; more preferably, the nucleotide sequence encoding the amino acid sequence of CDR1 in the heavy chain variable region of the mouse-derived antibody consists of nucleotides 91 to 105 of SEQ ID NO: 5;

The amino acid sequence of the CDR2 of the mouse-derived antibody heavy chain variable region consists of residues 50 to 66 of SEQ ID NO: 6; more preferably, the nucleotide sequence encoding the amino acid sequence of CDR2 in the heavy chain variable region of the mouse-derived antibody consists of nucleotides 148 to 198 of SEQ ID NO: 5;

The amino acid sequence of the CDR3 of the mouse-derived antibody heavy chain variable region consists of residues 99 to 109 of SEQ ID NO: 6; more preferably, the nucleotide sequence encoding the amino acid sequence of CDR3 in the heavy chain variable region of the mouse-derived antibody consists of nucleotides 295 to 327 of SEQ ID NO: 5;

And/or, the amino acid sequence of the CDR1 of the mouse-derived antibody light chain variable region consists of residues 24 to 34 of SEQ ID NO: 8; more preferably, the nucleotide sequence encoding the amino acid sequence of CDR1 in the light chain variable region of the mouse-derived antibody consists of nucleotides 70 to 102 of SEQ ID NO: 7;

The amino acid sequence of the CDR2 of the mouse-derived antibody heavy chain variable region consists of residues 50 to 56 of SEQ ID NO: 8; more preferably, the nucleotide sequence encoding the amino acid sequence of CDR2 in the heavy chain variable region of the mouse-derived antibody consists of nucleotides 148 to 168 of SEQ ID NO: 7;

The amino acid sequence of the CDR3 of the mouse-derived antibody heavy chain variable region consists of residues 89 to 97 of SEQ ID NO: 8; more preferably, the nucleotide sequence encoding the amino acid sequence of CDR3 in the heavy chain variable region of the mouse-derived antibody consists of nucleotides 265 to 291 of SEQ ID NO: 7;

The human antibody variable region framework was selected, wherein the light chain FR sequence on the antibody light chain variable region is derived from human germ line light chain, comprising a combination of human antibody light chain framework of 1) FR1, FR2, FR3 regions of A2, B3 or O18, and 2) region of FR4 region of JK2 or JK5; the heavy chain FR sequence on the heavy chain variable region of the antibody, derived from human germ line heavy chain sequence, comprising a combination of human antibody heavy chain framework of 1) VH3-48, VH3-30 or FR1, FR2, FR3 regions of VH3-11, and 2) FR4 region of JH6. In general, the selection of human acceptor framework region should be similar to the framework region of the donor antibody, or most similar to the consensus sequence of the variable region subfamily. Following grafting, sequence mutations can be made in the donor and/or acceptor sequences to optimize antigen binding, functionality, codon usage, expression levels, and the like, including introduction of non-human residues into the framework regions.

Preferably, the humanized anti-TPBG antibody comprises at least one heavy chain variable region and/or one light chain variable region. Wherein the amino acid sequence of the heavy chain variable region is set forth in SEQ ID NO: 2, SEQ ID NO: 6, SEQ ID NO: 16, SEQ ID NO: 18, SEQ ID NO:20, SEQ ID NO:22, SEQ ID NO:24, SEQ ID NO:34, SEQ ID NO: 36, SEQ ID NO:38 or SEQ ID NO:40; the amino acid sequence of the light chain variable region is set forth in SEQ ID NO:4, SEQ ID NO:8, SEQ ID NO:26, SEQ ID NO:28, SEQ ID NO:30, SEQ ID NO:32, SEQ ID NO:42, SEQ ID NO:44 or SEQ ID NO:46. More preferably, the nucleotide sequence encoding the heavy chain variable region is set forth in SEQ ID NO:1, SEQ ID NO:5, SEQ ID NO:15, SEQ ID NO:17, SEQ ID NO:19, SEQ ID NO:21, SEQ ID NO:23, SEQ ID NO:33, SEQ ID NO:35, SEQ ID NO:37 or SEQ ID NO:39, respectively; the nucleotide sequence encoding the light chain variable region is set forth in SEQ ID NO:3, SEQ ID NO:7, SEQ ID NO:25, SEQ ID NO:27, SEQ ID NO:29, SEQ ID NO:31, SEQ ID NO:41, SEQ ID NO:43 or SEQ ID NO:45, respectively;

Or, the amino acid sequence of the heavy chain variable region has at least 80% sequence identity to the sequence set forth in SEQ ID NO: 2, SEQ ID NO: 6, SEQ ID NO: 16, SEQ ID NO: 18, SEQ ID NO:20, SEQ ID NO:22, SEQ ID NO:24, SEQ ID NO:34, SEQ ID NO:36, SEQ ID NO:38 or SEQ ID NO:40; the amino acid sequence of the light chain variable region has at least 80% sequence identity to the sequence set forth in SEQ ID NO:4, SEQ ID NO:8, SEQ ID NO:26, SEQ ID NO:28, SEQ ID NO:30, SEQ ID NO:32, SEQ ID NO:42, SEQ ID NO:44 or SEQ ID NO:46. Preferably, the amino acid sequence of the heavy chain variable region has at least 80% sequence identity to the amino acid sequence encoded by the nucleotide sequence set forth in SEQ ID NO:1, SEQ ID NO:5, SEQ ID NO:15, SEQ ID NO:17, SEQ ID NO:19, SEQ ID NO:21, SEQ ID NO:23, SEQ ID NO:33, SEQ ID NO:35, SEQ ID NO:37 or SEQ ID NO:39; the amino acid sequence of the light chain variable region has at least 80% sequence identity to the amino acid sequence encoded by the nucleotide sequence set forth in SEQ ID NO:3, SEQ ID NO:7, SEQ ID NO:25, SEQ ID NO:27, SEQ ID NO:29, SEQ ID NO:31, SEQ ID NO:41, SEQ ID NO:43 or SEQ ID NO:45;

Preferably, the amino acid sequence of the heavy chain variable region is set forth in SEQ ID NO: 18 and the amino acid sequence of the light chain variable region is set forth in SEQ ID NO: 26; more preferably, the nucleotide sequence encoding the amino acid sequence of the heavy chain variable region is set forth in SEQ ID NO: 17 and the nucleotide sequence encoding the amino acid sequence of the light chain variable region is set forth in SEQ ID NO: 25.

Or, the amino acid sequence of the heavy chain variable region is set forth in SEQ ID NO: 20 and the amino acid sequence of the light chain variable region is set forth in SEQ ID NO: 26; more preferably, the nucleotide sequence encoding the amino acid sequence of the heavy chain variable region is set forth in SEQ ID NO: 19 and the nucleotide sequence encoding the amino acid sequence of the light chain variable region is set forth in SEQ ID NO: 25.

Or, the amino acid sequence of the heavy chain variable region is set forth in SEQ ID NO: 24 and the amino acid sequence of the light chain variable region is set forth in SEQ ID NO: 26; more preferably, the nucleotide sequence encoding the amino acid sequence of the heavy chain variable region is set forth in SEQ ID NO: 23 and the nucleotide sequence encoding the amino acid sequence of the light chain variable region is set forth in SEQ ID NO: 25.

Or, the amino acid sequence of the heavy chain variable region is set forth in SEQ ID NO: 16 and the amino acid sequence of the light chain variable region is set forth in SEQ ID NO: 28; more preferably, the nucleotide sequence encoding the amino acid sequence of the heavy chain variable region is set forth in SEQ ID NO: 15 and the nucleotide sequence encoding the amino acid sequence of the light chain variable region is set forth in SEQ ID NO: 27.

Or, the amino acid sequence of the heavy chain variable region is set forth in SEQ ID NO: 18 and the amino acid sequence of the light chain variable region is set forth in SEQ ID NO: 28; more preferably, the nucleotide sequence encoding the amino acid sequence of the heavy chain variable region is set forth in SEQ ID NO: 17 and the nucleotide sequence encoding the amino acid sequence of the light chain variable region is set forth in SEQ ID NO: 27.

Or, the amino acid sequence of the heavy chain variable region is set forth in SEQ ID NO: 20 and the amino acid sequence of the light chain variable region is set forth in SEQ ID NO: 28; more preferably, the nucleotide sequence encoding the amino acid sequence of the heavy chain variable region is set forth in SEQ ID NO: 19 and the nucleotide sequence encoding the amino acid sequence of the light chain variable region is set forth in SEQ ID NO: 27.

Or, the amino acid sequence of the heavy chain variable region is set forth in SEQ ID NO: 22 and the amino acid sequence of the light chain variable region is set forth in SEQ ID NO: 28; more preferably, the nucleotide sequence encoding the amino acid sequence of the heavy chain variable region is set forth in SEQ ID NO: 21 and the nucleotide sequence encoding the amino acid sequence of the light chain variable region is set forth in SEQ ID NO: 27.

Or, the amino acid sequence of the heavy chain variable region is set forth in SEQ ID NO: 24 and the amino acid sequence of the light chain variable region is set forth in SEQ ID NO: 28; more preferably, the nucleotide sequence encoding the amino acid sequence of the heavy chain variable region is set forth in SEQ ID NO: 23 and the nucleotide sequence encoding the amino acid sequence of the light chain variable region is set forth in SEQ ID NO: 27.

Or, the amino acid sequence of the heavy chain variable region is set forth in SEQ ID NO: 18 and the amino acid sequence of the light chain variable region is set forth in SEQ ID NO: 30; more preferably, the nucleotide sequence encoding the amino acid sequence of the heavy chain variable region is set forth in SEQ ID NO: 17 and the nucleotide sequence encoding the amino acid sequence of the light chain variable region is set forth in SEQ ID NO: 29.

Or, the amino acid sequence of the heavy chain variable region is set forth in SEQ ID NO: 20 and the amino acid sequence of the light chain variable region is set forth in SEQ ID NO: 30; more preferably, the nucleotide sequence encoding the amino acid sequence of the heavy chain variable region is set forth in SEQ ID NO: 19 and the nucleotide sequence encoding the amino acid sequence of the light chain variable region is set forth in SEQ ID NO: 29.

Or, the amino acid sequence of the heavy chain variable region is set forth in SEQ ID NO: 24 and the amino acid sequence of the light chain variable region is set forth in SEQ ID NO: 30; more preferably, the nucleotide sequence encoding the amino acid sequence of the heavy chain variable region is set forth in SEQ ID NO: 23 and the nucleotide sequence encoding the amino acid sequence of the light chain variable region is set forth in SEQ ID NO: 29.

Or, the amino acid sequence of the heavy chain variable region is set forth in SEQ ID NO: 16 and the amino acid sequence of the light chain variable region is set forth in SEQ ID NO: 32; more preferably, the nucleotide sequence encoding the amino acid sequence of the heavy chain variable region is set forth in SEQ ID NO: 15 and the nucleotide sequence encoding the amino acid sequence of the light chain variable region is set forth in SEQ ID NO: 31.

Or, the amino acid sequence of the heavy chain variable region is set forth in SEQ ID NO: 18 and the amino acid sequence of the light chain variable region is set forth in SEQ ID NO: 32; more preferably, the nucleotide sequence encoding the amino acid sequence of the heavy chain variable region is set forth in SEQ ID NO: 17 and the nucleotide sequence encoding the amino acid sequence of the light chain variable region is set forth in SEQ ID NO: 31.

Or, the amino acid sequence of the heavy chain variable region is set forth in SEQ ID NO: 20 and the amino acid sequence of the light chain variable region is set forth in SEQ ID NO: 32; more preferably, the nucleotide sequence encoding the amino acid sequence of the heavy chain variable region is set forth in SEQ ID NO: 19 and the nucleotide sequence encoding the amino acid sequence of the light chain variable region is set forth in SEQ ID NO: 31.

Or, the amino acid sequence of the heavy chain variable region is set forth in SEQ ID NO: 22 and the amino acid sequence of the light chain variable region is set forth in SEQ ID NO: 32; more preferably, the nucleotide sequence encoding the amino acid sequence of the heavy chain variable region is set forth in SEQ ID NO: 21 and the nucleotide sequence encoding the amino acid sequence of the light chain variable region is set forth in SEQ ID NO: 31.

Or, the amino acid sequence of the heavy chain variable region is set forth in SEQ ID NO: 24 and the amino acid sequence of the light chain variable region is set forth in SEQ ID NO: 32; more preferably, the nucleotide sequence encoding the amino acid sequence of the heavy chain variable region is set forth in SEQ ID NO: 23 and the nucleotide sequence encoding the amino acid sequence of the light chain variable region is set forth in SEQ ID NO: 31.

Or, the amino acid sequence of the heavy chain variable region is set forth in SEQ ID NO: 34 and the amino acid sequence of the light chain variable region is set forth in SEQ ID NO: 42; more preferably, the nucleotide sequence encoding the amino acid sequence of the heavy chain variable region is set forth in SEQ ID NO: 33 and the nucleotide sequence encoding the amino acid sequence of the light chain variable region is set forth in SEQ ID NO: 41.

Or, the amino acid sequence of the heavy chain variable region is set forth in SEQ ID NO: 36 and the amino acid sequence of the light chain variable region is set forth in SEQ ID NO: 42; more preferably, the nucleotide sequence encoding the amino acid sequence of the heavy chain variable region is set forth in SEQ ID NO: 35 and the nucleotide sequence encoding the amino acid sequence of the light chain variable region is set forth in SEQ ID NO: 41.

Or, the amino acid sequence of the heavy chain variable region is set forth in SEQ ID NO: 38 and the amino acid sequence of the light chain variable region is set forth in SEQ ID NO: 42; more preferably, the nucleotide sequence encoding the amino acid sequence of the heavy chain variable region is set forth in SEQ ID NO: 37 and the nucleotide sequence encoding the amino acid sequence of the light chain variable region is set forth in SEQ ID NO: 41.

Or, the amino acid sequence of the heavy chain variable region is set forth in SEQ ID NO: 40 and the amino acid sequence of the light chain variable region is set forth in SEQ ID NO: 42; more preferably, the nucleotide sequence encoding the amino acid sequence of the heavy chain variable region is set forth in SEQ ID NO: 39 and the nucleotide sequence encoding the amino acid sequence of the light chain variable region is set forth in SEQ ID NO: 41.

Or, the amino acid sequence of the heavy chain variable region is set forth in SEQ ID NO: 34 and the amino acid sequence of the light chain variable region is set forth in SEQ ID NO: 44; more preferably, the nucleotide sequence encoding the amino acid sequence of the heavy chain variable region is set forth in SEQ ID NO: 33 and the nucleotide sequence encoding the amino acid sequence of the light chain variable region is set forth in SEQ ID NO: 43.

Or, the amino acid sequence of the heavy chain variable region is set forth in SEQ ID NO: 36 and the amino acid sequence of the light chain variable region is set forth in SEQ ID NO: 44; more preferably, the nucleotide sequence encoding the amino acid sequence of the heavy chain variable region is set forth in SEQ ID NO: 35 and the nucleotide sequence encoding the amino acid sequence of the light chain variable region is set forth in SEQ ID NO: 43.

Or, the amino acid sequence of the heavy chain variable region is set forth in SEQ ID NO: 38 and the amino acid sequence of the light chain variable region is set forth in SEQ ID NO: 44; more preferably, the nucleotide sequence encoding the amino acid sequence of the heavy chain variable region is set forth in SEQ ID NO: 37 and the nucleotide sequence encoding the amino acid sequence of the light chain variable region is set forth in SEQ ID NO: 43.

Or, the amino acid sequence of the heavy chain variable region is set forth in SEQ ID NO: 40 and the amino acid sequence of the light chain variable region is set forth in SEQ ID NO: 44; more preferably, the nucleotide sequence encoding the amino acid sequence of the heavy chain variable region is set forth in SEQ ID NO: 39 and the nucleotide sequence encoding the amino acid sequence of the light chain variable region is set forth in SEQ ID NO: 43.

Or, the amino acid sequence of the heavy chain variable region is set forth in SEQ ID NO: 34 and the amino acid sequence of the light chain variable region is set forth in SEQ ID NO: 46; more preferably, the nucleotide sequence encoding the amino acid sequence of the heavy chain variable region is set forth in SEQ ID NO: 33 and the nucleotide sequence encoding the amino acid sequence of the light chain variable region is set forth in SEQ ID NO: 45.

Or, the amino acid sequence of the heavy chain variable region is set forth in SEQ ID NO: 36 and the amino acid sequence of the light chain variable region is set forth in SEQ ID NO: 46; more preferably, the nucleotide sequence encoding the amino acid sequence of the heavy chain variable region is set forth in SEQ ID NO: 35 and the nucleotide sequence encoding the amino acid sequence of the light chain variable region is set forth in SEQ ID NO: 45.

Or, the amino acid sequence of the heavy chain variable region is set forth in SEQ ID NO: 38 and the amino acid sequence of the light chain variable region is set forth in SEQ ID NO: 46; more preferably, the nucleotide sequence encoding the amino acid sequence of the heavy chain variable region is set forth in SEQ ID NO: 37 and the nucleotide sequence encoding the amino acid sequence of the light chain variable region is set forth in SEQ ID NO: 45.

Or, the amino acid sequence of the heavy chain variable region is set forth in SEQ ID NO: 40 and the amino acid sequence of the light chain variable region is set forth in SEQ ID NO: 46; more preferably, the nucleotide sequence encoding the amino acid sequence of the heavy chain variable region is set forth in SEQ ID NO: 39 and the nucleotide sequence encoding the amino acid sequence of the light chain variable region is set forth in SEQ ID NO: 45.

In summary, the SEQ ID numbers of amino acid sequence described above are listed in Table 1-1.

TABLE 1-1

SEQ ID NOs of Humanized Anti-TPBG Antibody Protein

| Numbers of Antibodies | Heavy Chain Variable Region SEQ ID NO: | Light Chain Variable Region SEQ ID NO: |
| --- | --- | --- |
| c12B12 | 2 | 4 |
| h12B12-1 | 18 | 26 |
| h12B12-2 | 20 | 26 |
| h12B12-3 | 24 | 26 |
| h12B12-4 | 16 | 28 |
| h12B12-5 | 18 | 28 |
| h12B12-6 | 20 | 28 |
| h12B12-7 | 22 | 28 |
| h12B12-8 | 24 | 28 |
| h12B12-9 | 18 | 30 |
| h12B12-10 | 20 | 30 |
| h12B12-11 | 24 | 30 |
| h12B12-12 | 16 | 32 |
| h12B12-13 | 18 | 32 |
| h12B12-14 | 20 | 32 |
| h12B12-15 | 22 | 32 |
| h12B12-16 | 24 | 32 |
| c28D4 | 6 | 8 |
| h28D4-1 | 34 | 42 |
| h28D4-2 | 36 | 42 |
| h28D4-3 | 38 | 42 |
| h28D4-4 | 40 | 42 |
| h28D4-5 | 34 | 44 |
| h28D4-6 | 36 | 44 |
| h28D4-7 | 38 | 44 |
| h28D4-8 | 40 | 44 |
| h28D4-9 | 34 | 46 |
| h28D4-10 | 36 | 46 |
| h28D4-11 | 38 | 46 |
| h28D4-12 | 40 | 46 |

Wherein the numbers in Table 1-1 are the SEQ ID NOs in the sequence listing, e.g. the amino acid sequence of heavy chain variable region of h12B12-1 is set forth in SEQ ID NO:18, while the amino acid sequence of light chain variable region of h12B12-1 is set forth in SEQ ID NO:26.

The present humanized anti-TPBG antibody is preferably one or more of antibody full-length protein, antigen-antibody binding domain protein fragment, bispecific antibody, multispecific antibody, single chain antibody fragment (scFv), single domain antibody (sdAb) and single-domain antibody, and monoclonal antibody or polyclonal antibody produced from the above antibodies. The monoclonal antibodies can be produced by a variety of methods and techniques, including hybridoma technique, phage display technique, and single lymphocyte gene cloning technique, etc. The conventional method is the preparation of monoclonal antibodies from wild-type or transgenic mice by hybridoma technology. The invention also includes super-humanized antibodies, diabody, etc.

The full-length antibody protein is a conventional full-length antibody in the art, comprising heavy chain variable region, light chain variable region, heavy chain constant region, and light chain constant region.

Preferably, the humanized anti-TPBG antibody further comprises human antibody heavy chain constant region and/or human antibody light chain constant region. The heavy chain variable region and the light chain variable region constitute humanized antibody full-length protein with human heavy chain constant region and human light chain constant region. Wherein the humanized antibody heavy chain constant region is a conventional human antibody heavy chain constant region in the art and may comprise constant region derived from human constant region, further comprising heavy chain constant region of human IgG1, IgG2, IgG3, IgG4 or variants thereof. The humanized antibody light chain constant region is a conventional human antibody heavy chain constant region in the art and may comprise constant region derived from a human constant region, further comprising light chain constant region of human κ, λ chain or variant thereof.

The single chain antibody fragment is a conventional single-chain antibody in the art, comprising the heavy chain variable region, the light chain variable region and a short peptide of 15-20 amino acids.

The antigen-antibody binding domain protein fragment is a conventional antigen-antibody binding domain protein fragment in the art, comprising light chain variable region, light chain constant region, and Fd segment of heavy chain constant region. Preferably, the antigen-antibody binding domain protein fragments are Fab and F(ab').

The single domain antibody is a conventional single domain antibody in the art, comprising heavy chain variable regions and heavy chain constant regions.

The single region antibody is a conventional single region antibody in the art, comprising heavy chain variable region only.

Wherein the preparation method of the humanized anti-TPBG antibody is a conventional preparation method in the art. The preparation method is preferably obtained by isolating the antibody from expression transformant recombinantly expressing the humanized anti-TPBG antibody or by artificially synthesizing the protein sequence. The method for isolating the antibody from expression transformant recombinantly expressing the humanized anti-TPBG antibody is preferable to be the following method: cloning the nucleic acid molecule encoding the humanized anti-TPBG antibody into a recombinant vector, and transforming the resulting recombinant vector into a transformant. Then the humanized anti-TPBG antibody can be obtained by isolated and purified by culturing the resulting recombinant expression transformant. The preparation of representative humanized anti-TPBG antibodies of the invention is described in Embodiment 1.

Humanized antibody is also broadly a class of chimeric antibody in which the variable region residues responsible for antigen binding includes complementarity determining regions derived from non-human species, shortened complementarity determining regions, or any other residues involved in antigen binding, whereas the remaining variable region residues, e.g. residues and constant regions of the framework regions, are at least partially derived from human antibody sequences. The subset of framework region residues and constant region residues of the humanized antibody can be derived from a non-human source. The variable region of a humanized antibody is also described as a humanized light chain variable region and/or heavy chain variable region. Non-human species are generally species used for immunization with antigens, such as mice, rats, rabbits, non-human primates, or other non-human mammal species. Humanized antibody is generally less immunogenic than traditional chimeric antibodies and exhibit improved stability upon administration to humans.

Complementarity determining regions (CDRs) are residues of antibody variable regions involved in antigen binding. Several numbering systems for identifying CDRs are conventional, such as, for example, Kabat definition, Chothia definition, and AbM definition. In summary, the Kabat definition is based on sequence variability, and the Chothia definition is based on the position of the structural loop region, while the AbM definition is a compromise between the Kabat and Chothia methods. According to the Kabat, Chothia or AbM algorithm, the light chain variable region has three CDR regions, the CDR1 consist of amino acid residues 24-34 (CDR1-L), the CDR2 consist of amino acid residues 50-56 (CDR2-L), and the CDR3 consist of amino acid residues 89-97 (CDR3-L). Due to the change in the length of the variable region, in different central or different subgroups, the 27th position of amino acid sequence may have 1-6 amino acid residues, and the 95th position of amino acid sequence may have 1-6 amino acid residues, which are numbered by adding English letters to the original number, such as: 27A, 27B, 95A, 95B, etc. According to the Kabat definition, the CDRs of the heavy chain variable region are defined by residues in positions 31 and 35B (CDR1-H), positions 50 and 65 (CDR2-H), and positions 95 and 102 (CDR3-H) (according to Kabat numbering). According to the Chothia definition, the CDRs of the heavy chain variable region are defined by residues in positions 26 and 32 (CDR1-H), positions 52 and 56 (CDR2-H), and positions 95 and 102 (CDR3-H) (according to the Chothia number). According to the AbM definition, the CDRs of the heavy chain variable region are defined by residues in positions 26 and 35B (CDR1-H), positions 50 and 58 (CDR2-H), and positions 95 and 102 (CDR3-H) (according to Kabat number). Similar to the light chain variable region, a plurality of amino acids may be present in positions 35, 52, 82, and 100, and are numbered A, B, C, and the like. See Martin et al. (1989) Proc. Nat 1. Acad. Sci. USA 86: 9268-9272; Martin et al. (1991) Methods Enzymol. 203: 121-153; Pedersen et al. (1992) Immunomethods 1: 126; Structure Prediction, Oxford University Press, Oxford, pp. 141-172.

Specificity determining regions (SDRs) are residues within CDRs that interact directly with antigen. SDRs correspond to hypervariable residues. See Padlan et al. (1995) FASEB J. 9: 133-139).

Framework residues are a portion of light chain variable region or heavy chain variable region, and antibody variable region residues other than hypervariable residues (hypervariable residues are mostly complementarity determining region or CDR) or CDR residues, serving as a skeleton for the antigen binding loop (CDR) of this variable domain. The framework residues can be derived from naturally existing human antibodies, such as the framework regions of human antibodies that are substantially similar to the framework regions of mouse anti-TPBG antibodies 12B12 or 28D4. Artificial framework region sequences representing consensus sequences between individual sequences can also be used. When framework regions for humanization are selected, sequences that are widely present in humans may be superior to less common sequences. Additional mutations in the human framework receptor sequence can be made to restore mouse residues believed to be involved in antigen contact and/or residues involved in the structural integrity of the antigen binding site, or to improve antibody expression. Peptide structure prediction can be used to analyze humanized heavy chain variable region and light chain variable region sequences to identify and avoid post-translational protein modification sites introduced by humanized design.

The humanized antibodies can be prepared using any of a variety of methods, including veneering and grafting of complementarity determining regions (CDRs), grafting of shortened CDRs, grafting of specificity determining regions (SDRs), and Frankenstein assembly.

The humanized antibody also involves in super-humanization of antibody, which is a method for preparing a humanized antibody, without relying on the human framework sequence as an analysis point, but relying on comparison of structural type between CDRs of the non-human antibody and human antibody, particularly the human antibody encoding by the human germline sequence, from which a candidate human antibody sequence of suitable human framework sequence that can be obtained is identified. For example, human residues can replace non-human residues in CDRs, and one or more of replacement have been introduced into the CDRs. One premise of veneering is that the immunogenicity of the mouse antibody variable region is derived from its surface residues, and the mobility of the residues and the accessibility of the solvent are essential conditions for it becoming an epitope. According to the analysis results of the existing crystal structure data of antibody, the fidelity of the relative solvent accessibility distribution of the human and mouse antibody variable region residues reach 98% at the sequence pairing position, indicating that among the heterogeneous species, the residues that induce immune response are caused by the remaining species-specific solvent accessible surface residues. Therefore, by changing the mouse-specific surface residues to human-derived residues, the surface profile of the human antibody can be simulated and the recognition of the human immune system can be avoided to achieve the purpose of humanization. Briefly, the veneering is based on the concept of reducing the amino acid sequence of potential immunogenicity in rodents or other non-human antibody by reconstituting the solvent-accessible surface of the antibody with human amino acid sequence. See Padlan (1991) Mol. Immunol. 28: 489-980. Identification of the outer framework region residues of solvent accessible residues exposed to the surface on non-human antibody (the residues are different from those residues in the same position in the framework regions of human antibody) and replacing the identified residues with amino acids occupying the same position in the human antibody for veneering, i.e., the veneered antibody, the surface residues of which are mainly human sequences, and the internal residues are primarily the original mouse sequences. Grafting of CDRs is performed by replacing one or more CDRs of a receptor antibody (e.g., a human antibody or other antibody comprising a desired framework residue) with CDRs of a donor antibody (e.g., a non-human antibody). The receptor antibody can be selected based on the similarity of the framework residues between the candidate receptor antibody and the donor antibody. For example, according to the Frankenstein method, human framework regions that are substantially homologous to each framework region of related non-human antibodies were identified, and CDRs of non-human antibody onto the complexes of these different human framework regions were grafted. The above methods can be used to produce anti-TPBG antibodies of any desired sequence.

The invention also provides a nucleic acid encoding the above-described humanized anti-TPBG antibody, comprising nucleic acid encoding the heavy chain variable region, and/or nucleic acid encoding the light chain variable region.

Preferably, the amino acid sequence encoded by the nucleic acid of the heavy chain variable region consists of SEQ ID NO: 2, SEQ ID NO: 6, SEQ ID NO: 16, SEQ ID NO: 18, SEQ ID NO: SEQ ID NO: 22, SEQ ID NO: 24, SEQ ID NO: 34, SEQ ID NO: 36, SEQ ID NO: 38 or SEQ ID NO: 40; more preferably, the nucleotide sequence of the nucleic acid encoding the heavy chain variable region consists of SEQ ID NO: 1, SEQ ID NO: 5, SEQ ID NO: 15, SEQ ID NO: 17, SEQ ID NO: 19, SEQ ID NO: 21, SEQ ID NO: 23. SEQ ID NO: 33, SEQ ID NO: 35, SEQ ID NO: 37 or SEQ ID NO: 39; the nucleotide sequence of the nucleic acid encoding the light chain variable region consists of SEQ ID NO: 3, SEQ ID NO: 7, SEQ ID NO: 25, SEQ ID NO: 27, SEQ ID NO: 29, SEQ ID NO: 31, SEQ ID NO: 41, SEQ ID NO: 43 or SEQ ID NO: 45.

Further preferably, the amino acid sequence encoded by the nucleic acid of the heavy chain variable region is set forth in SEQ ID NO: 18, and the amino acid sequence of the variable region of the light chain is set forth in SEQ ID NO: 26. Preferably, the nucleotide sequence of the nucleic acid encoding the heavy chain variable region is set forth in SEQ ID NO: 17, and the nucleotide sequence of the nucleic acid encoding the light chain variable region is set forth in SEQ ID NO: 25;

Or, the amino acid sequence encoded by the nucleic acid of the heavy chain variable region is set forth in SEQ ID NO: 20, and the amino acid sequence of the variable region of the light chain is set forth in SEQ ID NO: 26. Preferably, the nucleotide sequence of the nucleic acid encoding the heavy chain variable region is set forth in SEQ ID NO: 19, and the nucleotide sequence of the nucleic acid encoding the light chain variable region is set forth in SEQ ID NO: 25;

Or, the amino acid sequence encoded by the nucleic acid of the heavy chain variable region is set forth in SEQ ID NO: 24, and the amino acid sequence of the variable region of the light chain is set forth in SEQ ID NO: 26. Preferably, the nucleotide sequence of the nucleic acid encoding the heavy chain variable region is set forth in SEQ ID NO: 23, and the nucleotide sequence of the nucleic acid encoding the light chain variable region is set forth in SEQ ID NO: 25;

Or, the amino acid sequence encoded by the nucleic acid of the heavy chain variable region is set forth in SEQ ID NO: 16, and the amino acid sequence of the variable region of the light chain is set forth in SEQ ID NO: 28. Preferably, the nucleotide sequence of the nucleic acid encoding the heavy chain variable region is set forth in SEQ ID NO: 15, and the nucleotide sequence of the nucleic acid encoding the light chain variable region is set forth in SEQ ID NO: 27;

Or, the amino acid sequence encoded by the nucleic acid of the heavy chain variable region is set forth in SEQ ID NO: 18, and the amino acid sequence of the variable region of the light chain is set forth in SEQ ID NO: 28. Preferably, the nucleotide sequence of the nucleic acid encoding the heavy chain variable region is set forth in SEQ ID NO: 17, and the nucleotide sequence of the nucleic acid encoding the light chain variable region is set forth in SEQ ID NO: 27;

Or, the amino acid sequence encoded by the nucleic acid of the heavy chain variable region is set forth in SEQ ID NO: 20, and the amino acid sequence of the variable region of the light chain is set forth in SEQ ID NO: 28. Preferably, the nucleotide sequence of the nucleic acid encoding the heavy chain variable region is set forth in SEQ ID NO: 19, and the nucleotide sequence of the nucleic acid encoding the light chain variable region is set forth in SEQ ID NO: 27;

Or, the amino acid sequence encoded by the nucleic acid of the heavy chain variable region is set forth in SEQ ID NO: 22, and the amino acid sequence of the variable region of the light chain is set forth in SEQ ID NO: 28. Preferably, the nucleotide sequence of the nucleic acid encoding the heavy chain variable region is set forth in SEQ ID NO: 21, and the nucleotide sequence of the nucleic acid encoding the light chain variable region is set forth in SEQ ID NO: 27;

Or, the amino acid sequence encoded by the nucleic acid of the heavy chain variable region is set forth in SEQ ID NO: 24, and the amino acid sequence of the variable region of the light chain is set forth in SEQ ID NO: 28. Preferably, the nucleotide sequence of the nucleic acid encoding the heavy chain variable region is set forth in SEQ ID NO: 23, and the nucleotide sequence of the nucleic acid encoding the light chain variable region is set forth in SEQ ID NO: 27;

Or, the amino acid sequence encoded by the nucleic acid of the heavy chain variable region is set forth in SEQ ID NO: 18, and the amino acid sequence of the variable region of the light chain is set forth in SEQ ID NO: 30. Preferably, the nucleotide sequence of the nucleic acid encoding the heavy chain variable region is set forth in SEQ ID NO: 17, and the nucleotide sequence of the nucleic acid encoding the light chain variable region is set forth in SEQ ID NO: 29;

Or, the amino acid sequence encoded by the nucleic acid of the heavy chain variable region is set forth in SEQ ID NO: 20, and the amino acid sequence of the variable region of the light chain is set forth in SEQ ID NO: 30. Preferably, the nucleotide sequence of the nucleic acid encoding the heavy chain variable region is set forth in SEQ ID NO: 19, and the nucleotide sequence of the nucleic acid encoding the light chain variable region is set forth in SEQ ID NO: 29;

Or, the amino acid sequence encoded by the nucleic acid of the heavy chain variable region is set forth in SEQ ID NO: 24, and the amino acid sequence of the variable region of the light chain is set forth in SEQ ID NO: 30. Preferably, the nucleotide sequence of the nucleic acid encoding the heavy chain variable region is set forth in SEQ ID NO: 23, and the nucleotide sequence of the nucleic acid encoding the light chain variable region is set forth in SEQ ID NO: 29;

Or, the amino acid sequence encoded by the nucleic acid of the heavy chain variable region is set forth in SEQ ID NO: 16, and the amino acid sequence of the variable region of the light chain is set forth in SEQ ID NO: 32. Preferably, the nucleotide sequence of the nucleic acid encoding the heavy chain variable region is set forth in SEQ ID NO: 15, and the nucleotide sequence of the nucleic acid encoding the light chain variable region is set forth in SEQ ID NO: 31;

Or, the amino acid sequence encoded by the nucleic acid of the heavy chain variable region is set forth in SEQ ID NO: 18, and the amino acid sequence of the variable region of the light chain is set forth in SEQ ID NO: 32. Preferably, the nucleotide sequence of the nucleic acid encoding the heavy chain variable region is set forth in SEQ ID NO: 17, and the nucleotide sequence of the nucleic acid encoding the light chain variable region is set forth in SEQ ID NO: 31;

Or, the amino acid sequence encoded by the nucleic acid of the heavy chain variable region is set forth in SEQ ID NO: 20, and the amino acid sequence of the variable region of the light chain is set forth in SEQ ID NO: 32. Preferably, the nucleotide sequence of the nucleic acid encoding the heavy chain variable region is set forth in SEQ ID NO: 19, and the nucleotide sequence of the nucleic acid encoding the light chain variable region is set forth in SEQ ID NO: 31;

Or, the amino acid sequence encoded by the nucleic acid of the heavy chain variable region is set forth in SEQ ID NO: 22, and the amino acid sequence of the variable region of the light chain is set forth in SEQ ID NO: 32. Preferably, the nucleotide sequence of the nucleic acid encoding the heavy chain variable region is set forth in SEQ ID NO: 21, and the nucleotide sequence of the nucleic acid encoding the light chain variable region is set forth in SEQ ID NO: 31;

Or, the amino acid sequence encoded by the nucleic acid of the heavy chain variable region is set forth in SEQ ID NO: 24, and the amino acid sequence of the variable region of the light chain is set forth in SEQ ID NO: 32. Preferably, the nucleotide sequence of the nucleic acid encoding the heavy chain variable region is set forth in SEQ ID NO: 23, and the nucleotide sequence of the nucleic acid encoding the light chain variable region is set forth in SEQ ID NO: 31;

Or, the amino acid sequence encoded by the nucleic acid of the heavy chain variable region is set forth in SEQ ID NO: 34, and the amino acid sequence of the variable region of the light chain is set forth in SEQ ID NO: 42. Preferably, the nucleotide sequence of the nucleic acid encoding the heavy chain variable region is set forth in SEQ ID NO: 33, and the nucleotide sequence of the nucleic acid encoding the light chain variable region is set forth in SEQ ID NO: 41;

Or, the amino acid sequence encoded by the nucleic acid of the heavy chain variable region is set forth in SEQ ID NO: 36, and the amino acid sequence of the variable region of the light chain is set forth in SEQ ID NO: 42. Preferably, the nucleotide sequence of the nucleic acid encoding the heavy chain variable region is set forth in SEQ ID NO: 35, and the nucleotide sequence of the nucleic acid encoding the light chain variable region is set forth in SEQ ID NO: 41;

Or, the amino acid sequence encoded by the nucleic acid of the heavy chain variable region is set forth in SEQ ID NO: 38, and the amino acid sequence of the variable region of the light chain is set forth in SEQ ID NO: 42. Preferably, the nucleotide sequence of the nucleic acid encoding the heavy chain variable region is set forth in SEQ ID NO: 37, and the nucleotide sequence of the nucleic acid encoding the light chain variable region is set forth in SEQ ID NO: 41;

Or, the amino acid sequence encoded by the nucleic acid of the heavy chain variable region is set forth in SEQ ID NO: 40, and the amino acid sequence of the variable region of the light chain is set forth in SEQ ID NO: 42. Preferably, the nucleotide sequence of the nucleic acid encoding the heavy chain variable region is set forth in SEQ ID NO: 39, and the nucleotide sequence of the nucleic acid encoding the light chain variable region is set forth in SEQ ID NO: 41;

Or, the amino acid sequence encoded by the nucleic acid of the heavy chain variable region is set forth in SEQ ID NO: 34, and the amino acid sequence of the variable region of the light chain is set forth in SEQ ID NO: 44. Preferably, the nucleotide sequence of the nucleic acid encoding the heavy chain variable region is set forth in SEQ ID NO: 33, and the nucleotide sequence of the nucleic acid encoding the light chain variable region is set forth in SEQ ID NO: 43;

Or, the amino acid sequence encoded by the nucleic acid of the heavy chain variable region is set forth in SEQ ID NO: 36, and the amino acid sequence of the variable region of the light chain is set forth in SEQ ID NO: 44. Preferably, the nucleotide sequence of the nucleic acid encoding the heavy chain variable region is set forth in SEQ ID NO: 35, and the nucleotide sequence of the nucleic acid encoding the light chain variable region is set forth in SEQ ID NO: 43;

Or, the amino acid sequence encoded by the nucleic acid of the heavy chain variable region is set forth in SEQ ID NO: 38, and the amino acid sequence of the variable region of the light chain is set forth in SEQ ID NO: 44. Preferably, the nucleotide sequence of the nucleic acid encoding the heavy chain variable region is set forth in SEQ ID NO: 37, and the nucleotide sequence of the nucleic acid encoding the light chain variable region is set forth in SEQ ID NO: 43;

Or, the amino acid sequence encoded by the nucleic acid of the heavy chain variable region is set forth in SEQ ID NO: 40, and the amino acid sequence of the variable region of the light chain is set forth in SEQ ID NO: 44. Preferably, the nucleotide sequence of the nucleic acid encoding the heavy chain variable region is set forth in SEQ ID NO: 39, and the nucleotide sequence of the nucleic acid encoding the light chain variable region is set forth in SEQ ID NO: 43;

Or, the amino acid sequence encoded by the nucleic acid of the heavy chain variable region is set forth in SEQ ID NO: 34, and the amino acid sequence of the variable region of the light chain is set forth in SEQ ID NO: 46. Preferably, the nucleotide sequence of the nucleic acid encoding the heavy chain variable region is set forth in SEQ ID NO: 33, and the nucleotide sequence of the nucleic acid encoding the light chain variable region is set forth in SEQ ID NO: 45;

Or, the amino acid sequence encoded by the nucleic acid of the heavy chain variable region is set forth in SEQ ID NO: 36, and the amino acid sequence of the variable region of the light chain is set forth in SEQ ID NO: 46. Preferably, the nucleotide sequence of the nucleic acid encoding the heavy chain variable region is set forth in SEQ ID NO: 35, and the nucleotide sequence of the nucleic acid encoding the light chain variable region is set forth in SEQ ID NO: 45;

Or, the amino acid sequence encoded by the nucleic acid of the heavy chain variable region is set forth in SEQ ID NO: 38, and the amino acid sequence of the variable region of the light chain is set forth in SEQ ID NO: 46. Preferably, the nucleotide sequence of the nucleic acid encoding the heavy chain variable region is set forth in SEQ ID NO: 37, and the nucleotide sequence of the nucleic acid encoding the light chain variable region is set forth in SEQ ID NO: 45;

Or, the amino acid sequence encoded by the nucleic acid of the heavy chain variable region is set forth in SEQ ID NO: 40, and the amino acid sequence of the variable region of the light chain is set forth in SEQ ID NO: 46. Preferably, the nucleotide sequence of the nucleic acid encoding the heavy chain variable region is set forth in SEQ ID NO: 39, and the nucleotide sequence of the nucleic acid encoding the light chain variable region is set forth in SEQ ID NO: 45.

In summary, the SEQ ID NOs of nucleotide sequences described above are listed in Table 1-2.

TABLE 1-2

SEQ ID NOs of TPBG antibodies gene

| Numbers of Antibodies | Heavy Chain Variable Region SEQ ID NO: | Light Chain Variable Region SEQ ID NO: |
|---|---|---|
| c12B12 | 1 | 3 |
| h12B12-1 | 17 | 25 |
| h12B12-2 | 19 | 25 |
| h12B12-3 | 23 | 25 |
| h12B12-4 | 15 | 27 |
| h12B12-5 | 17 | 27 |
| h12B12-6 | 19 | 27 |
| h12B12-7 | 21 | 27 |
| h12B12-8 | 23 | 27 |
| h12B12-9 | 17 | 29 |
| h12B12-10 | 19 | 29 |
| h12B12-11 | 23 | 29 |
| h12B12-12 | 15 | 31 |
| h12B12-13 | 17 | 31 |
| h12B12-14 | 19 | 31 |
| h12B12-15 | 21 | 31 |
| h12B12-16 | 23 | 31 |
| c28D4 | 5 | 7 |
| h28D4-1 | 33 | 41 |
| h28D4-2 | 35 | 41 |
| h28D4-3 | 37 | 41 |
| h28D4-4 | 39 | 41 |
| h28D4-5 | 33 | 43 |
| h28D4-6 | 35 | 43 |
| h28D4-7 | 37 | 43 |
| h28D4-8 | 39 | 43 |
| h28D4-9 | 33 | 45 |
| h28D4-10 | 35 | 45 |
| h28D4-11 | 37 | 45 |
| h28D4-12 | 39 | 45 | wherein, the numbers in Table 1-2 are the SEQ ID NOs in the sequence listing, such as the nucleotide sequence of the heavy chain protein variable region of h12B12-1 is set forth in SEQ ID NO: 17, and the nucleotide sequence of the light chain protein variable region of h12B12-1 is set forth in SEQ ID NO: 25.

The preparation method of the nucleic acid is a conventional preparation method in the art, and preferably includes the steps of obtaining nucleic acid molecule encoding the above humanized anti-TPBG antibody by gene cloning technology, or obtaining nucleic acid molecule encoding the above humanized anti-TPBG antibody by artificial full sequence synthesis.

One skilled in the art should know that homologs of the polynucleotide sequence encoding the above described humanized anti-TPBG antibodies can be provided by proper introduction of substitution, deletion, alteration, insertion or addition. Homologs of polynucleotide of the present invention can be prepared by substituting, deleting or adding one or more nucleotides of nucleic acid encoding the humanized anti-TPBG antibody while maintaining antibody activity.

The present invention further provides a recombinant expression vector comprising the nucleic acid described above.

Wherein the recombinant expression vector can be obtained by a conventional method in the art, i.e., ligating the nucleic acid molecules of the present invention to various expression vectors. The expression vector is a variety of conventional vectors in the art as long as it can carry the aforementioned nucleic acid molecule. The vector preferably includes: a variety of plasmids, cosmids, phage or viral vectors, and the like.

The present invention further provides a recombinant expression transformant comprising the recombinant expression vector described above.

Wherein, the preparation method of the recombinant expression transformant is a preparation method conventionally known in the art, preferably transforming the above-mentioned recombinant expression vectors into host cells. The host cells are a variety of host cells conventionally known in the art, as long as they are able to stably self-replicate the above-mentioned recombinant expression vectors and efficiently express their carried nucleic acid. Preferably, the host cell is *E. coli* TG1 or BL21 cells (expressing scFv or Fab antibody), or CHO-K1 cells (expressing full-length IgG antibody). The preferred recombinant expression transformant can be obtained by transforming the above-mentioned recombinant expression plasmid into host cells, wherein the method of transformation is a conventional method of transformation known in the art, preferably chemical transformation, heat shock or electrotransformation.

The present invention further provides cells or cell line comprising the recombinant expression vector described above. Preferably, the cells are mammalian or human cells, more preferably CHO cells, HEK-293 cells, HeLa cells, CV-1 cells or COS cells. Methods for producing stable cell lines after transforming a heterologous construct into cells described above are known in the art. The non-mammal host cell is preferably insect cell (Potter et al. (1993) Int. Rev. Immunol. 10(2-3): 103-112). The antibody can also be produced in transgenic animals (Houdebine (2002) Curr. Opin. Biotechno J. 13(6): 625-629) or transgenic plants (Schillberg et al. (2003) Cell Mol. Life Sci. 60 (3): 433-45).

The present invention further provides a method for preparation of humanized anti-TPBG antibody, which comprises following steps: culturing the above recombinant expression transformant, or cell, or cell line, and obtaining a humanized anti-TPBG antibody from the culture.

The invention also provides an immunoconjugate comprising the above-mentioned humanized anti-TPBG antibody covalently linked to a cytotoxic agent.

Preferably, for the immunoconjugate, 1 equivalent of the above-mentioned protein is linked to y equivalents of cytotoxic agent through x equivalents of linker, which has a structure shown in formula 1:

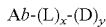  Formula 1 wherein Ab is the above-mentioned humanized antibody, L is a linker and D is a cytotoxic agent. The x is the conventional crosslinking degree known in the art, x is a natural number, preferably an integer selected from 1-20; y is 0 or natural number, preferably an integer selected from 0-20; x and y are preferably integers selected from 1-2, or 2-4, or 4-8, or 8-20, independently; preferably the ratio of x to y is 1:1.

The L is a conventional linker known in the art (also known as crosslinking agent or coupling agent). The L is comprised of two functional groups, i.e. one group reacting with antibody and the other group reacting with drug (e.g. aldehyde or ketone).

The drug is coupled to the above-mentioned humanized TPBG protein through linker. The L is released upon entry into cell, which comprises but not limited to the following functional groups: active esters, carbonates, carbamates, imine phosphate esters, oximes, hydrazones, acetals, orthoesters, amino groups, small peptides or nucleotide fragments.

Preferably, the L mainly comprises the structure shown in formula 2, which corresponds to the remaining part when the leaving group in the L is removed:

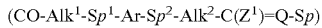  Formula 2 wherein $Alk^1$ and $Alk^2$ are independent bonds or branched or unbranched ($C_1$-$C_{10}$) alkylene chain; $Sp^1$ is —S—, —O—, —CONH—, —NHCO—, —NR'—, —N(CH$_2$CH$_2$)$_2$N— or —X—Ar'—Y— (CH$_2$)$_n$—Z, wherein X, Y and Z are independent bonds, —NR'—, —S— or —O—, provide that when n=0, at least one of Y and Z has to be a bond, and Ar' is 1,2-, 1,3- or 1,4-phenylene that is optionally substituted by 1, 2 or 3 groups selected from ($C_1$-$C_5$) alkyl, ($C_1$-$C_4$) alkoxy, ($C_1$-$C_4$) thioalkoxy, halogen, nitro, —COOR', —CONHR', —(CH$_2$)$_n$COOR', S (CH$_2$)$_n$COOR', —O(CH$_2$)$_n$CONHR' or —S(CH$_2$)$_n$CONHR', n is an integer selected from 0-5, on condition that when $Alk^1$ is a bond, $Sp^1$ is a bond; R' is a branched or unbranched ($C_1$-$C_5$) chain that is optionally substituted by 1 or 2 groups selected from —OH, ($C_1$-$C_4$) alkoxy, ($C_1$-$C_4$) thioalkoxy, halogen, nitro, ($C_1$-$C_3$) dialkylamino, or ($C_1$-$C_3$) trialkylammonium-A, wherein A is pharmaceutically acceptable anion of salt; Ar is 1, 2-; 1;3- or 1,4-phenylene that is optionally substituted by 1, 2 or 3 groups selected from ($C_1$-$C_6$)alkyl, ($C_1$-$C_5$) alkoxy, ($C_1$-$C_4$) thioalkoxy, halogen, nitro, —COOR', —CONHR', —O(CH$_2$)$_n$COOR', —S(CH$_2$)$_n$COOR', —O(CH$_2$)$_n$CONHR" or —S(CH$_2$)$_n$CONHR', wherein n and R' is as defined above, or Ar is 1,2-; 1,3-; 1,4-; 1,5-; 1,6-; 1,7-; 1,8-; 2,3-; 2,6- or 2,7-naphthylene, wherein naphthylene or phenothiazine is optionally substituted by 1, 2, 3 or 4 groups selected from ($C_1$-$C_6$) alkyl, ($C_1$-$C_5$) alkoxy, ($C_1$-$C_4$) thioalkoxy, halogen, nitro, —COOR', —CONHR', —O(CH$_2$)$_n$COOR', —S(CH$_2$)$_n$COOR' or —S(CH$_2$)$_n$CONHR', wherein n and R' is as defined above, on condition that when Ar is phenothiazine, $Sp^1$ is a bond that is connected only with nitrogen.

$Sp^2$ is a bond, —S— or —O—, provided that when $Alk^2$ is a bond, $Sp^2$ is a bond;

Z1 is H, ($C_1$-$C_5$) alkyl, or phenyl that is optionally substituted by 1, 2, or 3 groups selected from ($C_1$-$C_5$) alkyl, ($C_1$-$C_5$) alkoxy, ($C_1$-$C_4$) thioalkoxy, halogen, nitro, —COOR', —CONHR', —O(CH$_2$)$_n$COOR', —S(CH$_2$)$_n$COOR', —O(CH$_2$)$_n$CONHR' or —S(CH$_2$)$_n$CONHR', in which n and R' is as defined above;

Sp is linear or branched divalent or trivalent ($C_1$-$C_{18}$) group, divalent or trivalent aryl or heteroaryl group, divalent or trivalent ($C_3$-$C_{18}$) naphthenic or heterocyclic alkyl group, divalent or trivalent aryl or heteroaryl-aryl ($C_1$-$C_{18}$) group, divalent or trivalent naphthenic or heterocyclic alkyl-alkyl ($C_1$-$C_1$) group, or divalent or trivalent ($C_2$-$C_{18}$) unsaturated alkyl groups, wherein heteroaryl group is preferably furan, thiophene, N-methyl pyrroliy, pyridyl, N-methidazolyl, oxazolyl, pyrimidine, quinoline, isoquinoline, N-methyl carbazole group, amino-coumarin group, or phenazine group, and if Sp is a trivalent group, then Sp also can be optionally substituted by lower ($C_1$-$C_5$) dialkylamino, lower ($C_1$-$C_5$) alkoxy, hydroxyl, or lower ($C_1$-$C_5$) alkylthiol; and, Q is =NHNCO—, =NHNCS—, =NHNCONH—, =NHNCSNH— or =NHO—.

Preferably, $Alk^1$ is branched or unbranched ($C_1$-$C_5$) alkylene chain, $Sp^1$ is a bond, —S—, —O—, —CONH—, —NHCO— or —NR', wherein R' is as defined above, provided that when $Alk^1$ is bond, $Sp^1$ is bond;

Ar is 1,2-, 1,3- or 1,4-phenylene that is optionally substituted by 1,2 or 3 groups selected from ($C_1$-$C_6$) alkyl, ($C_1$-$C_5$) alkoxy, ($C_1$-$C_4$) thioalkoxy, halogen, nitro, —COOR', —CONHR', wherein n and R' is as defined above, or Ar is 1,2-; 1,3-; 1,4-; 1,5-; 1,6-; 1,7-; 1,8-; 2,3-; 2,6- or 2,7-naphthylene that is optionally substituted by 1, 2, 3 or 4 groups selected from ($C_1$-$C_6$) alkyl, ($C_1$-$C_5$) alkoxy, ($C_1$-$C_4$) thioalkoxy, halogen, nitro, —COOR', —CONHR', —O(CH$_2$)$_n$COOR', —S (CH$_2$)$_n$COOR', —O(CH$_2$)$_n$CONHR' or —S(CH$_2$)$_n$CONHR'.

Z1 is ($C_1$-$C_5$) alkyl, or phenyl that is optionally substituted by 1, 2, or 3 groups selected from ($C_1$-$C_5$) alkyl, ($C_1$-$C_4$) alkoxy, ($C_1$-$C_4$) thioalkoxy, halogen, nitro, —COOR', —CONHR', —O(CH$_2$) COOR', —S(CH$_2$) COOR', —O(CH$_2$)$_n$CONHR' or —S(CH$_2$)$_n$CONHR'; both $Alk^2$ and $Sp^2$ are bonds, and Sp and Q are only as defined above. The meaning of the bond mentioned above is covalent bond.

The L is preferably maleimidocaproyl (MC), maleimidocaproyl-L-valine-L-citrulline p-aminobenzyl alcohol (MC-VC-PAB) or 4-(N-maleimide methyl) cyclohexane-1-carboxylic succinimide (SMCC).

The D is a conventional cytotoxic agent known in the art, preferably selected from cytotoxin, chemotherapeutic agent, radioisotope, therapeutic nucleic acid, immunomodulator, anti-angiogenic agent, anti-proliferative apoptosis promoter, or cytolytic enzyme.

Wherein, the cytotoxin is a conventional cytotoxin known in the art, which generally refers to an active agent that inhibits or prevents cell function and/or causes cell destruction, preferably selected from antibiotics, microtubulin polymerization inhibitors, alkylating agents, protein synthesis inhibitors, protein kinase inhibitors, phosphatase inhibitors, topoisomerase inhibitors, protein kinase, phosphatase, topoisomerase or cyclin, more preferably selected from doxorubicin, daunorubicin, idarubicin, aclarubicin, zorubicin, mitoxantrone, epirubicin, carirubicin, nogalamycin, menogaril, pirarubicin, valrubicin, cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, adriamycin, cisplatin, carboplatin, cyclophosphamide, dacarbazine, vinblastine sulfate, vincristine, bleomycin, mustard nitrogen, prednisone, procarbazine, methotrexate, fluorouracil, etoposide, paclitaxel and paclitaxel analogue, platin (such as cisplatin or carboplatin), mitomycin, thiotepa, taxane, daunorubicin, actinomycin, anthramycin, azaserine, tamoxifen, dolastatin, auristatin and derivatives, hemiasterlin, esperamicin or maytansine analogue, most preferably selected from monomethyl auristatin E (MMAE), monomethyl auristatin F (MMAF) or N2'-deacetyl-N2'-(3-mercapto-1-oxypropyl) methesteine (DM1).

Wherein the chemotherapeutic agent is a conventional chemotherapeutic agent known in the art, preferably selected from alkylating agents, alkyl sulfonic acid esters chemotherapeutic agents, aziridine chemotherapeutic agents, vinyl amides and methylmelamine chemotherapeutic agents, mustard nitrogen, nitrourea chemotherapeutic agents, antibiotics, anti-metabolites, and folic acid chemotherapeutic agents, purine analogues, pyrimidine analogues, androgens, anti-adrenalines, folic acid supplements, maytansinol, polysaccharide complexes, taxane, platin analogues or retinoids, or pharmaceutically acceptable salts, acids, and derivatives thereof.

The alkylating agent is a conventional alkylating agent known in the art, preferably selected from thiotepa or cyclophosphamide. The alkyl sulfonic acid ester chemotherapeutic agent is a conventional alkyl sulfonic acid ester chemotherapeutic agent known in the art, preferably selected from busulfan, improsulfan or piposulfan. The aziridine chemotherapeutic agent is a conventional aziridine chemotherapeutic agent known in the art, preferably selected from the aziridine, such as carboquinone, meturedepa, or uredepa. The ethernamides and methylmelamine chemotherapeutic agent is a conventional ethernamides and methylmelamine chemotherapeutic agent known in the art, preferably selected from hexamethyl melamine, triethyl melamine, triethylenephosphoramide, triethylenethiophosphoramide or trimethylolmelamine. The mustard nitrogen is a conventional mustard nitrogen known in the art, preferably selected from phenylbutyrate mustard, naphthalene mustard, estramustine, isophosphamide, mustard nitrogen, mechlorethaminoxide hydrochloride, melphalan, novembichin, phenesterine, prednimustine, trofosfamide or uracilmustard. The nitrourea chemotherapeutic agent is a conventional nitrourea chemotherapeutic agent known in the art, preferably selected from carmustine, chlorozotocin, fotemustine, lomustin, nimustine or ranimustine. The antibiotic is a conventional antibiotic known in the art, preferably selected from aclacinomycin, actinomycin, anthramycin, azaserine, bleomycin, actinomycin C, calicheamicin, carabicin, caminomycin, carzinophilin, chromomycin, dactinomycin, daunorubicin, detorubicin, and 6-Diazo-5-Oxo-L-Norleucine, doxorubicin, epirubicin, esorubicin, darubicin, marcellomycin, mitomycin, mycophenolic acid, nogalamycin, olivomycin, peplomycin, potfiromycin, puromycin, triferricdoxorubicin, rodorubicin, streptonigrin, streptozocin, tuberculocidin, ubenimex, zinostatin or zorubicin. The anti-metaboilte is a conventional anti-metaboilte known in the art, preferably selected from methotrexate and 5-fluorouracil (5-FU). The folic acid chemotherapeutic agent is a conventional folic acid chemotherapeutic agent known in the art, preferably selected from denopterin, pteropterin, or trimetrexate. The purine analogue is a conventional analogue known in the art, preferably selected from fludarabine, 6-mercaptopurine, tiamiprine or thioguanine. The pyrimidine analogue is a conventional pyrimidine analogue known in the art, preferably selected from ancitabine, azacitidine, 6-azauridine, carmofur, cytarabine, dideoxyuridine, doxifluridine, enocitabine, floxuridine, or 5-EU. The androgen is a conventional androgen known in the art, preferably selected from calusterone, Dromostanolone propionate, epitiostanol, methasterone or testolactone. The anti-adrenaline is a conventional anti-adrenaline known in the art, preferably selected from aminoglutethimide, mitotane or trilostane. The folic acid supplement agent is folic acid supplement agent known in the art, preferably selected from frolinic acid, aceglatone, aldophosphamide glycoside, aminolevulinic acid, amsacrine, atrimustine, bisantrene, edatraxate, defofamine, demecolcine, diaziquone, eflornithine, elliptinium acetate, epothilone, etoglucid, gallium nitrate, hydroxyurea, lentinan or lonidainine. The maytansinol is a conventional maytansinol known in the art, preferably selected from maytansine, ansamitocin, mitoguazone, mitoxantrone, mopidanmol, nitrcerine, pentostatin, phenamet, pirarubicin, losoxantrone, podophyllinic acid, 2-ethyl hydrazide or procarbazine. The polysaccharide complex is a conventional polysaccharide complex known in the art, preferably selected from razoxane, rhizomycin, sizofiran, spirogermanium, tenuazonic acid, triaziquone, 2,2',2"-trichloro-triethylamine, trichothecene, urethane, vindesine, dacarbazine, mannomustine, dibromannitol, mitolactol, pipobroman, gacytosine, cytarabine, cyclophosphamide, or thiotepa, more preferably selected from T-2 toxin, verracurin A, roridin A, or anguidine. The taxane is a conventional taxane known in the art, preferably selected from paclitaxel, unhydrogenated castor oil, Abraxane Nanoparticle (American Pharmaceutical Partners, Schaumberg, Ill.), docetaxel, chlorambuci, gemcitabin, 6-thioguanine, mercaptopurine or methotrexate. The platinum analogue is a conventional platinum analogue known in the art, preferably selected from cisplatin, carboplatin, vinblastine, etoposid, ifosfamide, mitoxantrone, vinorelbine, novantrone, teniposide, edatrexate, daunomycin, aminopterin, capecitabine ibandronate, CPT-11, topoisomerase inhibitors RFS 2000 or difluorometylornithine. The retinoid is a conventional retinoid known in the art, preferably selected from retinoic acid.

Wherein the radioisotope is a conventional radioisotope known in the art, which preferably binding directly to the above-mentioned humanized anti-TPBG antibody or bind to the above-mentioned humanized anti-TPBG antibody via chelating agents. More preferably, binding directly to the cysteine residues of the humanized anti-TPBG antibody. Preferably, the radioisotope is selected from alpha emitters, beta emitters and auger electrons suitable for radiation therapy, and positron emitters or gamma emitters suitable for diagnosis. More preferably, the radioisotope is selected from $^{18}$fluorine, $^{64}$copper and $^{65}$copper. $^{67}$gallium, $^{68}$gallium, $^{77}$bromine, $^{80m}$bromine, $^{95}$ruthenium, $^{97}$ruthenium, $^{103}$ruthenium, $^{105}$ruthenium, $^{99m}$technetium, $^{107}$mercury, $^{203}$mercury, $^{123}$iodine, $^{124}$iodine, $^{125}$iodine, $^{126}$iodine, $^{131}$iodine, $^{133}$iodine, $^{126}$iodine, $^{111}$indium, $^{113}$indium, $^{99m}$rhenium, $^{105}$rhenium, $^{101}$rhenium, $^{186}$rhenium, $^{188}$rhenium, $^{121m}$tellurium, $^{121m}$tellurium, $^{125m}$tellurium, $^{165}$thulium, $^{167}$thulium, $^{168}$thulium, $^{90}$thulium, $^{213}$bismuth, $^{213}$lead or $^{225}$actinide or derivatives of nitrides or oxides thereof.

Wherein the therapeutic nucleic acid is a conventional therapeutic nucleic acid known in the art, preferably genes encoding immunomodulato, anti-angiogenic agents, anti-proliferative agents or pro-apoptotic agents. The therapeutic agents comprise the therapeutic agents, derivatives thereof and pharmaceutically acceptable salts, acids and derivatives of the therapeutic agents.

Wherein the immunomodulator is a conventional immunomodulator known in the art, which triggers immune responses, including humoral immune responses (e.g. production of an antigen specific antibody), and cell mediated immune responses (e.g. lymphocyte proliferation), preferably selected from cytokines, growth factors, hormones, anti-hormone drugs, immunosuppressants or corticosteroids. The cytokine is a conventional known cytokine in the art, preferably selected from xanthine, interleukin or interferon. The growth factor is a conventional known growth factor in the art, preferably selected from TNF, CSF, GM-CSF or G-CSF. The hormone is a conventional hormone known in the art, preferably selected from estrogen, androgen or progestogen. More preferably, the estrogen is diethylstilbestrol or estradiol. More preferably, the androgen is testosterone or fluoxymesterone. More preferably, the progesterone is megestrol acetate or medroxyprogesterone acetate. The corticosteroid is a conventional corticosteroid known in the art, preferably selected from prednisone, dexamethasone or cortisone. The anti-steroid drug is a conventional anti-steroid drug known in the art, which can block the effect of hormones on tumor, inhibit the production of cytokines, down-regulate the expression of autoantigens, or mask the immunosuppressant of MHC antigen, preferably selected from anti-estrogen drugs, anti-androgen drugs or anti-adrenergic drugs. More preferably, the anti-estrogen drugs are selected from tamoxifen, raloxifene, aromatase inhibitory 4 (5)-imidazole, 4-hydroxy tamoxifen, trioxifene or toremifene. The anti-androgenic drugs are selected from flutamide, nilutamide, bicalutamide, leuprorelin, or goserelin. The immunosuppressant is a conventional immunosuppressant known in the art, preferably selected from 2-amino-6-aryl-5-pyrimidine, azathioprine, cyclophosphamide, bromocriptine, danazol, dapsone, glutaraldehyde, anti-idiotype antibody against MHC antigens and MHC fragments, cyclosporin A, steroids such as glucocorticoids, streptokinases, TGFb, rapamycin, T cell receptors, T cell receptor fragments, cytokine receptor antagonists or T cell receptor antibodies. More preferably, the cytokine receptor antagonists are selected from anti-interferon antibodies, anti-IL10 antibodies, anti-TNFa antibodies or anti-IL2 antibodies.

Wherein the anti-angiogenic agent is a conventional anti-angiogenic agent known in the art, preferably selected from farnesyl transferase inhibitors, COX-2 inhibitors, VEGF inhibitors, bFGF inhibitors, steroid sulfate esterase inhibitors, interleukin-24, thrombus protein, metallospondin protein, type-I interferon, interleukin-12, and protamine, angiostatin, laminin, endostatin or prolactin fragment. More preferably 2-methoxy estradiol diamino sulfonate (2-MeOE2bisMATE).

Wherein the anti-proliferation and pro-apoptosis agent is a conventional anti-proliferation and pro-apoptosis agent known in the art, preferably selected from PPAR-γ activators, retinoids, triterpenes, EGF receptor inhibitors, telomere terminal transferase inhibitors, iron chelating agents, apoptotic proteins, Bcl-2 and Bcl-X (L) inhibitors, and TNF-α/FAS ligand/TNF-associated apoptosis-inducing ligand and its signal transduction activator or PI3K-Akt survival pathway signal inhibitors. The PPAR-γ activator is a conventional PPAR-γ activator known in the art, preferably cyclopentenone prostaglandin (cyPGs). The triterpenes are conventional triterpenes known in the art, preferably selected from cycloartane, lupanes, ursane, oleanane, friedelane, damanane, cucurbitacin, limonoid analogues, or triterpenes compound. The EGF receptor inhibitor is a conventional EGF receptor inhibitor known in the art, preferably selected from HER4, rapamycin or 1,25-dihydroxy-cholecalciferol (vitamin D). The iron chelates are conventional iron chelate known in the art, preferably 3-aminopyridine-2-carboxaldehyde-thiosemicarbazone. The apoptosis protein is a conventional apoptosis protein known in the art, preferably the viral protein 3-VP3 of chicken anemia virus. The PI3K-Akt survival pathway signal inhibitor is a conventional PI3K-Akt survival pathway signal inhibitor known in the art, preferably UCN-01 or geldanamycin.

Wherein the cytolytic enzyme is a conventional cytolytic enzyme known in the art, preferably RNA enzyme.

In the present invention, preferably, x=y=n in Formula 1; according to this, in one preferred embodiment, $-(L)_x-(D)_y$ is:

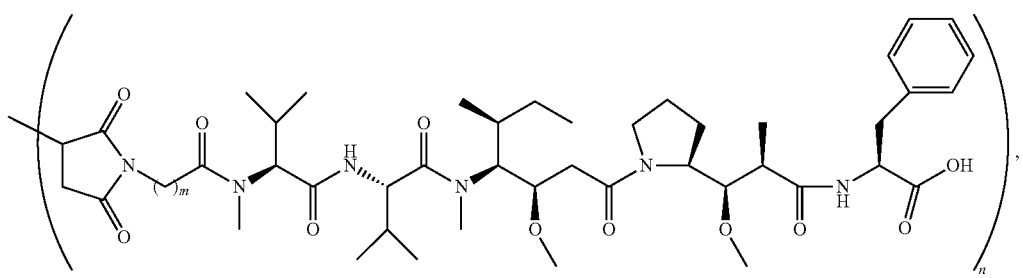

wherein m is 1-10, preferably is 5, i.e. maleimidocaproyl.

In one preferred embodiment, -(L)$_x$-(D)$_y$ is:

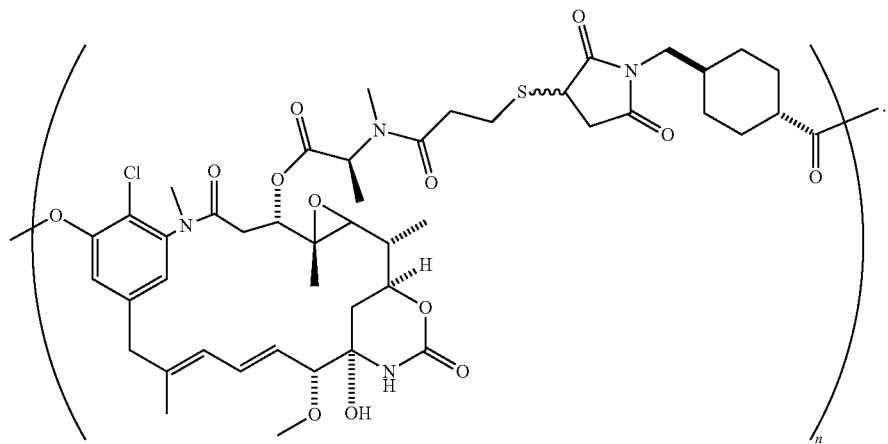

In one preferred embodiment, -(L)$_x$-(D)$_y$ is:

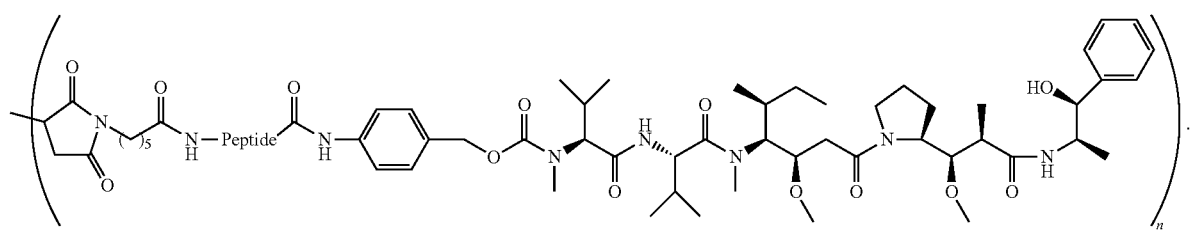

Most preferably, the D is a microtubulin synthetase inhibitor, monomethylauristatin F (MMAF), and the linker L is maleimidocaproyl (maleimidocaproyl, MC), and the structure of the immunoconjugate is shown in Formula 3, Formula 3

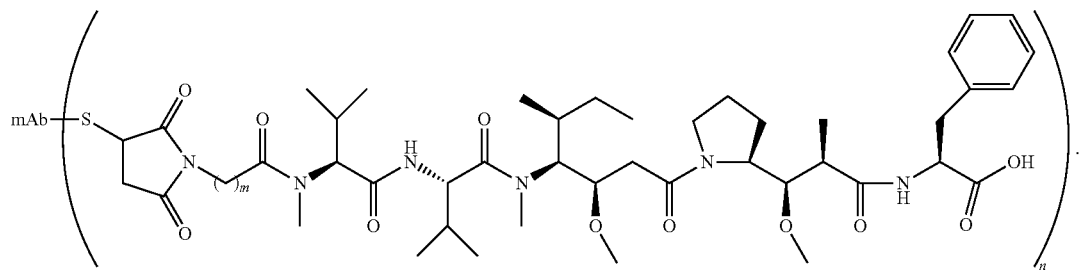

wherein, mAb is the above-mentioned humanized anti-TPBG antibody.

or, the L is N-succinimidyl 4-(maleimidomethyl) cyclohexanecarboxylate; D is N2'-Deacetyl-N2'-(3-mercapto-1-oxopropyl) maytansine (DM1), and the structure of the immunoconjugate is shown in Formula 4, jugate and pharmaceutically acceptable vehicle. Preferably, the pharmaceutical composition further comprises other anti-tumor antibody as active ingredient such as other antibody against targets in the course of cancer immune cycle, Formula 4

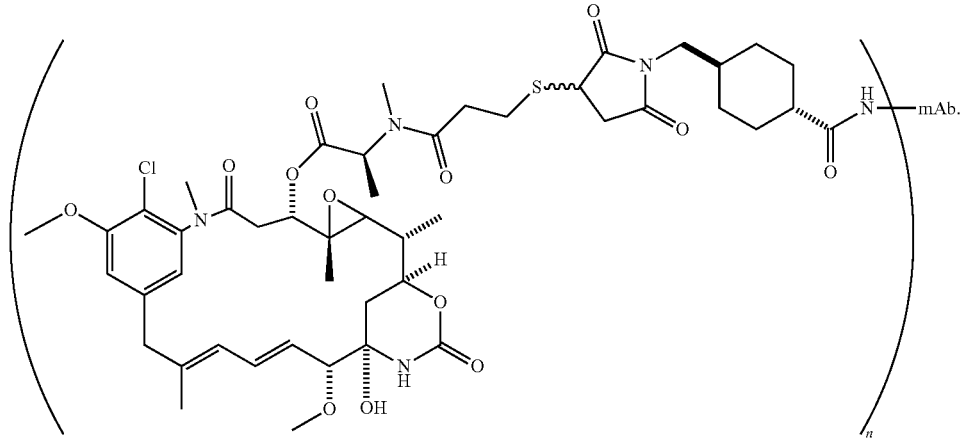

or, L is Maleimidocaproyl-L-valine-L-citrulline-p-aminobenzyl alcohol, and D is Monomethyl auristatin E (MMAE), and the structure of the immunoconjugate is shown in Formula 5 and the other antibody is preferably anti-PD-1 antibody. wherein, the cancer immune cycle specifically includes (death) cancer cells releasing antigen, presentation, initiation and activation of tumor antigen, transportation of T cell Formula 5

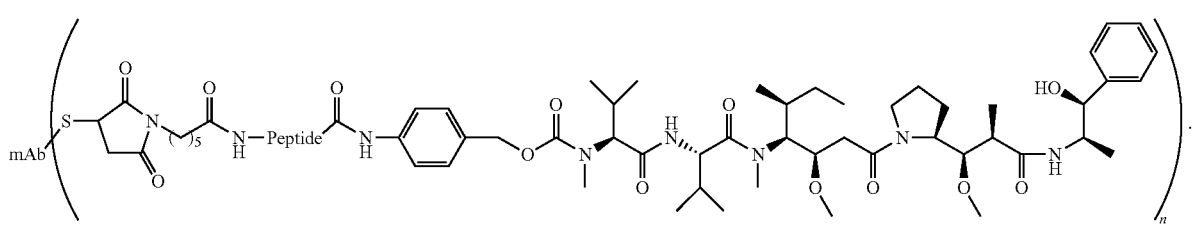

wherein n is a natural number, preferably an integer selected from 1-20, more preferably an integer selected from 1-2, or 2-4, or 4-8, or 8-20.

The preparation method of the immunoconjugate is a conventional preparation method known in the art, preferably adopting the method described in Doronina, 2006, Bioconjugate Chem. 17114-124. Preferably, the preparation method of which produces the immunoconjugate with the minimum low coupling fraction (LCF) of less than 10%.

In a preferred embodiment of the invention, the preparation method comprises the following steps: dialyzing the humanized anti-TPBG antibody with sodium borate buffer, pH 6.5-8.5, and adding with tris(2-carboxyethyl) phosphine (TCEP), wherein the molar ratio of TCEP to the above humanized anti-TPBG antibody is 2-10. Reduction reacting for 1-4 hours at room temperature to obtain reaction solution A. Eluting the reaction solution A to remove excess above humanized anti-TPBG antibody and obtain reaction solution B. Adding MC-MMAF to reaction solution B, wherein the molar ratio of MC-MMAF to the purified humanized TPBG antibody is 5-20, and reacting for 4 hours at 10-37° C.

The immunoconjugate exists in any physical form known in the art, preferably in a clear solution.

The present invention further provides a pharmaceutical composition comprising the above-mentioned immunoconto the tumor site, infiltration of T-Cell into tumor, recognition of cancer cells by T cell and killing of cancer cells (see Chen D S, Mellman I. Oncology Meets Immunology: The Cancer-Immunity Cycle [J]. Immunity, 2013, 39(1): 1-10.). The immunoconjugated ADC of the present invention functions in the first stage of cancer immune cycle [(death) cancer cells releasing antigen], and the anti-PD-1 antibody functions in the seventh stage of the cancer immune cycle (killing of cancer cells).

The pharmaceutically acceptable vehicle can be a conventional vehicle known in the art. The vehicle can be any physiologically or pharmaceutically acceptable drug excipient. The drug excipient is a conventional drug excipient known in the art, preferably comprising pharmaceutically acceptable excipients, fillers or diluents. More preferably, the pharmaceutical composition comprises 0.01-99.99% of the above-mentioned humanized anti-TPBG antibody and 0.01-99.99% of pharmaceutical vehicle, wherein the percentage is the mass percentage of the pharmaceutical composition.

The pharmaceutical composition in the present invention is preferably parenteral administration, injection administration or oral administration. The injection administration preferably comprising intravenous injection, intramuscular injection, intraperitoneal injection, intradermal injection or subcutaneous injection, etc. The pharmaceutical composition has a variety of conventional dosage forms known in the art, preferably solid, semi-solid or liquid, i.e. aqueous solution, non-aqueous solution or suspension, more preferably tablets, capsules, granules, injection agents or infusion agents. More preferably administered intravascularly, subcutaneously, intraperitoneally or intramuscularly. Preferably, the pharmaceutical composition further can be administered as aerosol or rough spray, i.e. administered nasally; or administered intrathecally, intramedullary or intraventricularly. More preferably, the pharmaceutical composition further can be administered transdermally, percutaneously, topically, enterally, intravaginally, sublingually or rectally.

The dosage of the pharmaceutical composition in the present invention can be adjusted according to the amount of composition that achieves the desired diagnostic or therapeutic effects. Administration plan also can be single injection or multiple injections, or can be adjusted according to specific conditions. The chosen of dosage and regimen can be appropriately adjusted depend on the factors comprising the activity and stability (i.e. half-life) of the pharmaceutical composition, preparation, routes of administration, combination with other drugs or therapies, diseases or conditions to be detected and/or treated, and the health condition and previous medical history of the recipients to be treated.

Effective dose of the pharmaceutical composition of present invention can be preliminarily estimated in cell culture experiments or animal models such as rodents, rabbits, dogs, pigs and/or primates. Animal models can also be used to determine the appropriate concentration and route of administration, and the effective dose and route of administration of human being can be determined subsequently. Generally, the determination and adjustment of an effective amount or dose to be administered, and the evaluation of when and how such adjustment will be made are known to a person skilled in the art.

For combination therapy, the above-mentioned humanized anti-TPBG antibody, immunoconjugate and/or additional therapeutic or diagnostic agents can be used separately as single drugs within any time frame appropriate for performing the anticipated therapy or diagnostics. The therapeutic or diagnostic agent may be another anti-tumor antibody, such as antibody against target in the course of cancer immune cycle, preferably anti-PD-1 antibody. Therefore, these single drugs can be administered simultaneously (i.e. as single preparation within minutes or hours) or sequentially. For instance, these single drugs can be administered within a year, or 10, 8, 6, 4 or 2 months, or within 4, 3, 2, or 1 week (s), or within 5, 4, 3, 2 or 1 day (s).

As for additional guidance on preparation, dosage, administration regimen and measurable therapeutic results, please refer to Berkow et al. (2000) The Merck Manual of Medical Information and Merck&Co.Inc., Whitehouse Station, N.J.; Ebadi (1998) CRC Desk Reference of Clinical Pharmacology and etc.

The present invention provides a use of above-mentioned humanized anti-TPBG antibody in preparing anti-tumor drugs.

The present invention provides a use of above-mentioned immunoconjugate in preparing anti-tumor drugs.

The present invention provides a use of above-mentioned pharmaceutical composition in preparing anti-tumor drugs.

In the above-described applications, the humanized TPBG antibody, the immunoconjugate or the pharmaceutical composition is preferably administered in combination with antibody against targets in the course of cancer immune cycle, preferably anti-PD-1 antibody.

The tumor is a conventional tumor, preferably the tumor overexpressing TPBG protein, more preferably squamous/adenoma lung cancer (non-small cell lung carcinoma), invasive breast cancer, colon cancer, rectal cancer, gastric cancer, squamous cervical cancer, invasive endometrial adenocarcinoma, invasive pancreatic cancer, ovarian cancer, squamous bladder cancer, choriocarcinoma, bronchial carcinoma, breast cancer, cervical cancer, pancreatic cancer or seminal vesicle cancer.

The present invention further provides a method for detecting cells overexpressing TPBG protein, comprising following steps: contacting the humanized anti-TPBG antibody with sample to be tested in vitro, and detecting the combination between above-mentioned humanized anti-TPBG antibody and the samples to be tested.

The meaning of overexpression is a conventional meaning of overexpression known in the art, preferably the mean fluorescence intensity (MFI) of the above-mentioned humanized anti-TPBG antibody is three times or more than the MFI of IgG subtype when subjecting the cells in the sample to be tested to FACS.

The detection method of binding is a conventional detection method known in the art, preferably FACS detection method.

The "TPBG-positive" cells in the present invention are cells that overexpress TPBG protein, e.g. the NCI-H1568 cell strain; otherwise, they are designated as "TPBG-negative" cells, e.g. tumor cell line NCI-H1770.

On the basis of common knowledge in the art, the above preferred conditions can be arbitrarily combined to obtain the preferred embodiments of the present invention.

All the materials and agents are commercially available.

The positive and progressive effect of the present invention is that the TPBG antibody in the present invention is a humanized antibody which has binding affinity with human TPBG antigen of at least about $1\times10^{-7}$ M to about $1\times10^{-12}$ M, and the humanized anti-TPBG antibody and its conjugates show specific binding of targeting TPBG expressing cells in vivo. The humanized anti-TPBG antibody of the invention is capable of binding the extracellular domain of TPBG protein receptor in both protein and cellular levels. A conjugate is formed when humanized TPBG antibody is coupled with a small-molecule compound such as MC-MMAF, and the conjugate performs effective cytotoxic killing on TPBG-positive cells. Besides, humanized TPBG antibody internalizes small-molecule compounds, such as MMAF, into the cell via endocytosis, and degrade and release the small-molecule compounds in cells, thus playing a cytotoxic role. Therefore, the antibody cross-linked drug prepared by the humanized TPBG antibody effectively kills tumor cells and treat tumors; for example, the combination therapy with anti-PD-1 antibody significantly prolongs the survival of mice, and after combination therapy, immunological memory is formed in mice with complete tumor remission. The conjugated antibody also show higher clearance rate, lower elimination half-life and exposure, which significantly inhibits the growth of non-small cell lung carcinoma patient-derived xenograft tumor PDX in mice.

Figure 2:
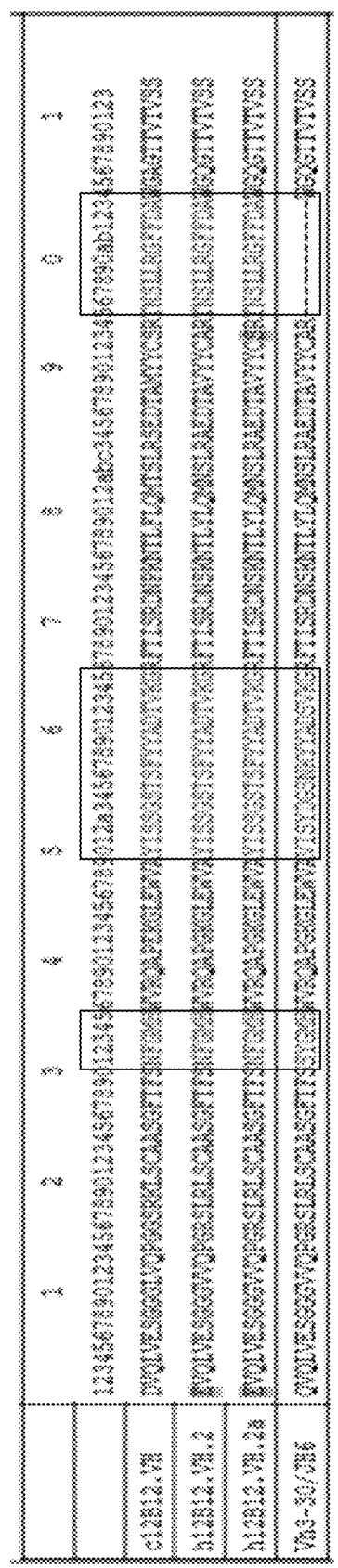

FIG. 2. Sequence comparison of humanized anti-TPBG antibody 12B12 heavy chain variable region h12B12.VH2 and its variants with 12B12 chimeric antibody VH and human germline VH exon hVH3-30/JH-6. CDRs are boxed off.

Figure 3:
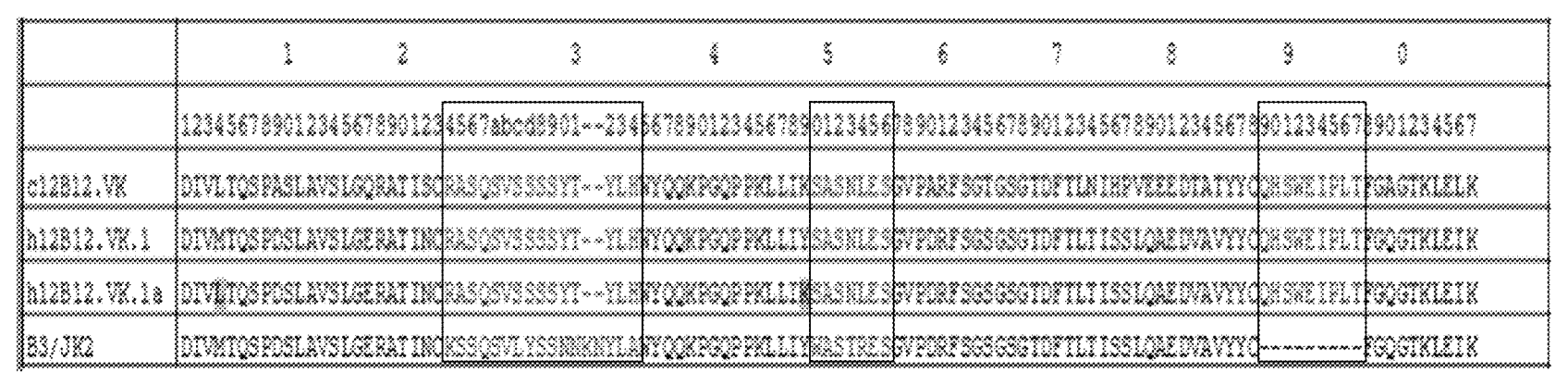

FIG. 3. Sequence comparison of humanized anti-TPBG antibody 12B12 light chain variable region h12B12.Vk1 and its variants with 12B12 chimeric antibody Vk and human germline Vk exon B3/Jk-2. CDRs are boxed off.

FIG. 4. Sequence comparison of humanized anti-TPBG antibody 12B12 light chain variable region h12B12.Vk2 and its variants with 12B12 chimeric antibody Vk and human germline Vk exon A2/Jk-2. CDRs are boxed off.

Figure 5:
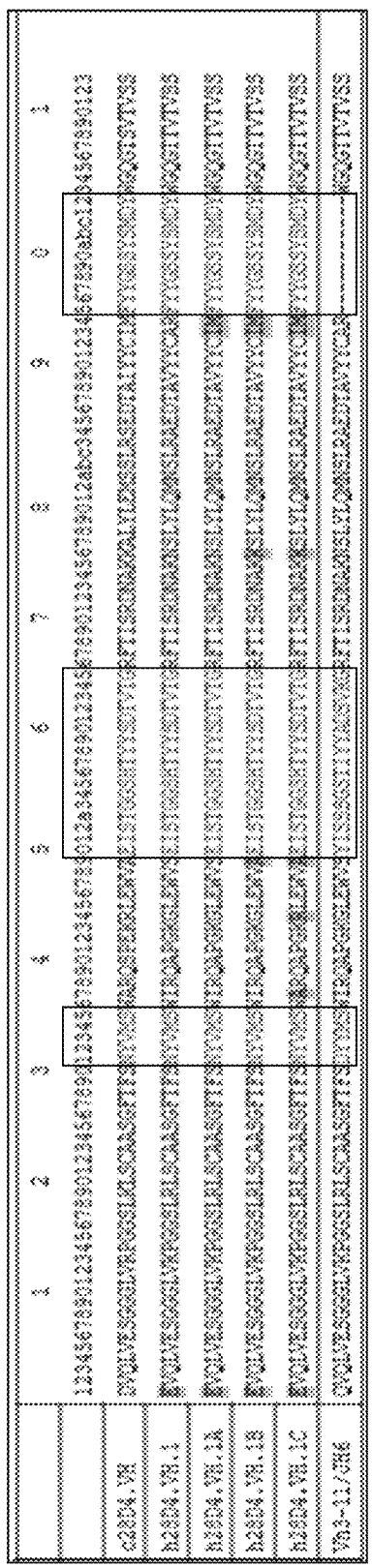

FIG. 5. Sequence comparison of the humanized anti-TPBG antibody 28D4 heavy chain variable region h28D4.VH1 and its variants with the 28D4 chimeric antibody VH and the human germline VH exon hVH3-11/JH-6. CDRs are boxed off.

Figure 6:
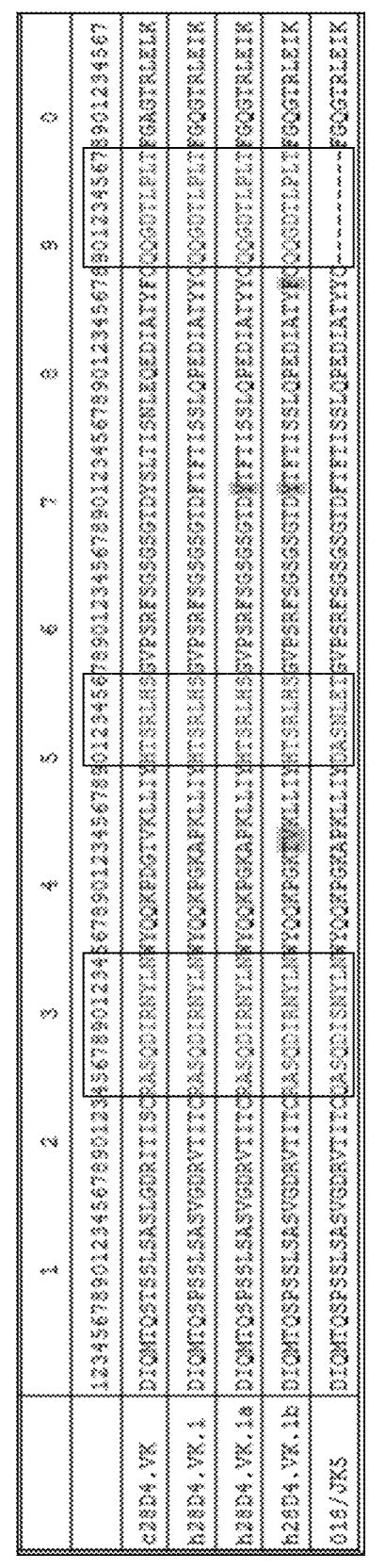

FIG. 6. Sequence comparison of humanized anti-TPBG antibody 28D4 light chain variable region h28D4.Vk1 and its variants with 28D4 chimeric antibody Vk and human germline Vk exon O18/Jk-5. CDRs are boxed off.

Figure 7A:
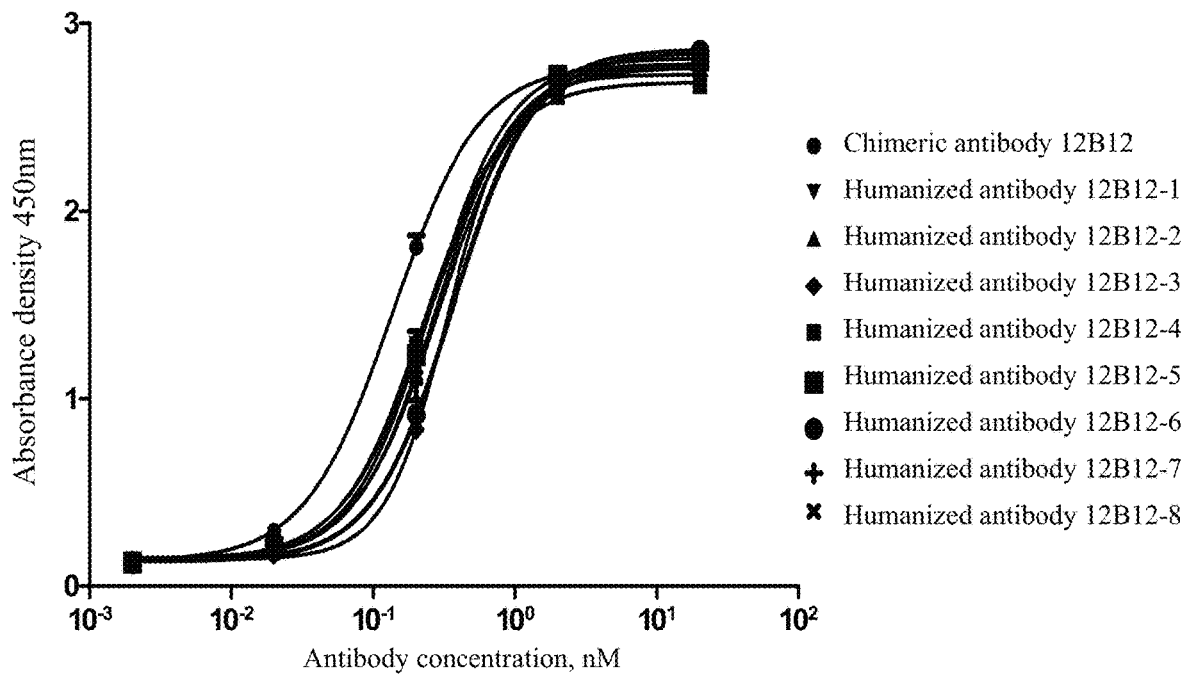
Figure 7B:
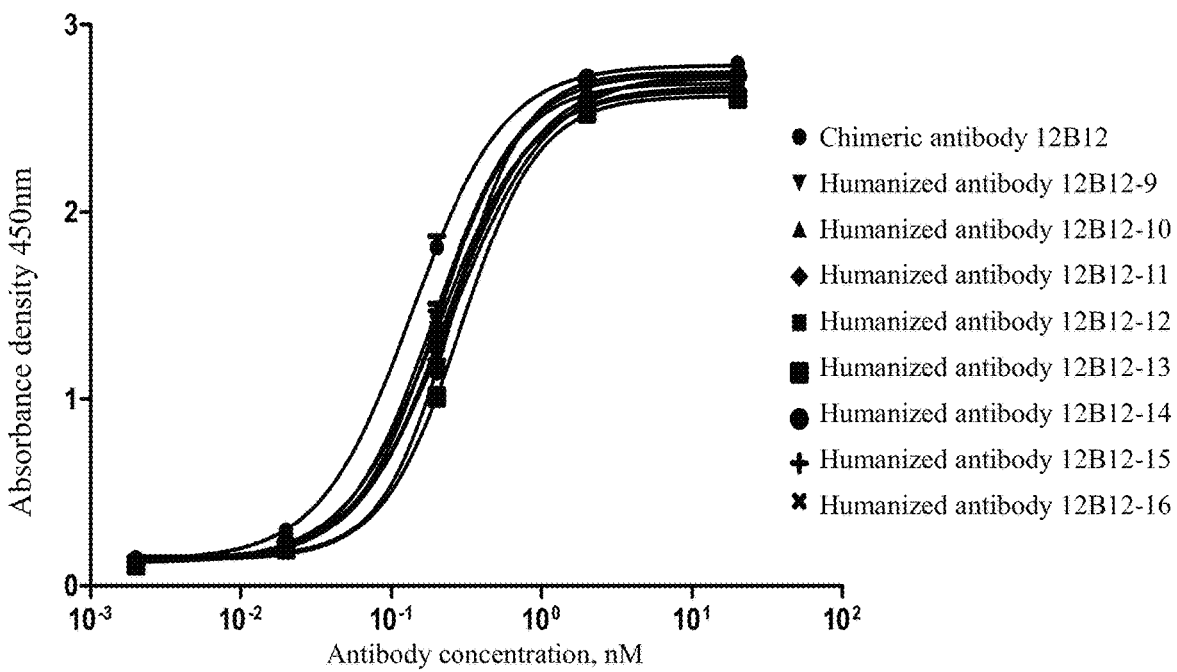

FIGS. 7A and 7B. ELISA detection of the binding of the humanized antibody 12B12 variant to the human TPBG-hFc protein.

Figure 8A:
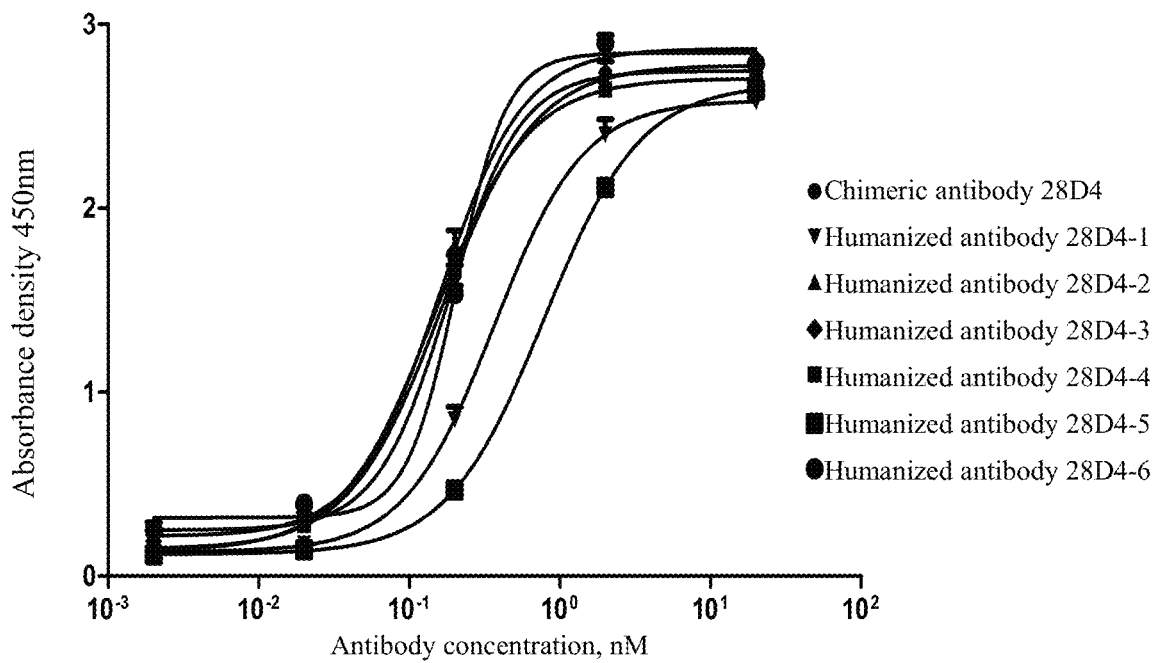
Figure 8B:
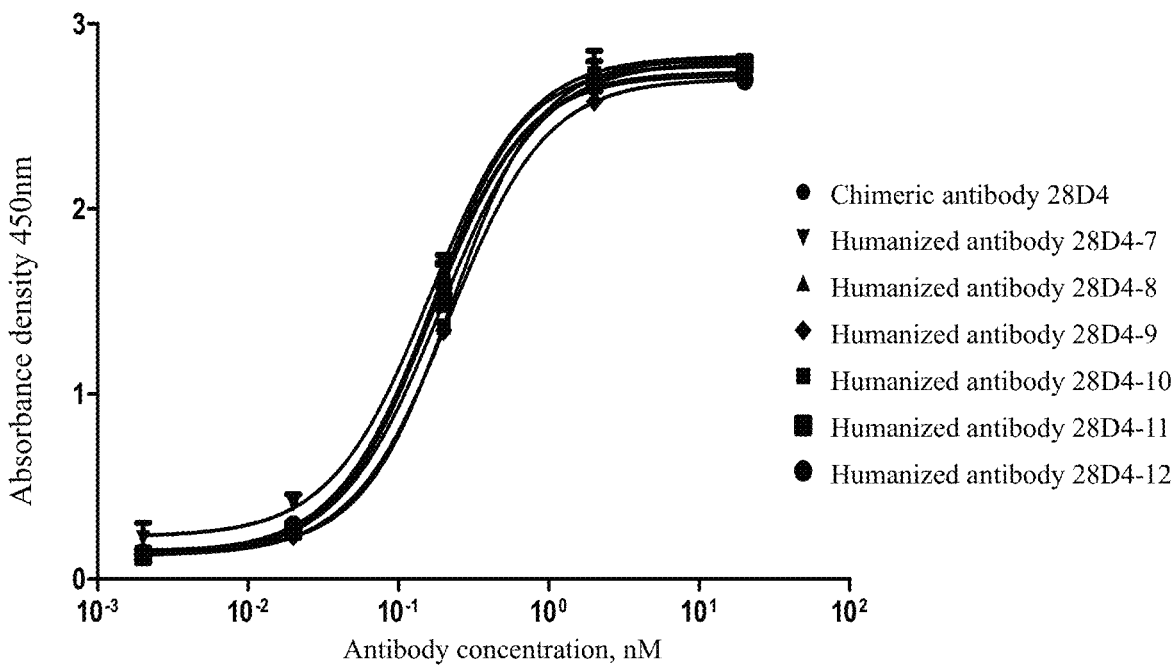

FIGS. 8A and 8B. ELISA detection of the binding of the humanized antibody 28D4 variant to the human TPBG-hFc protein.

Figure 9A:
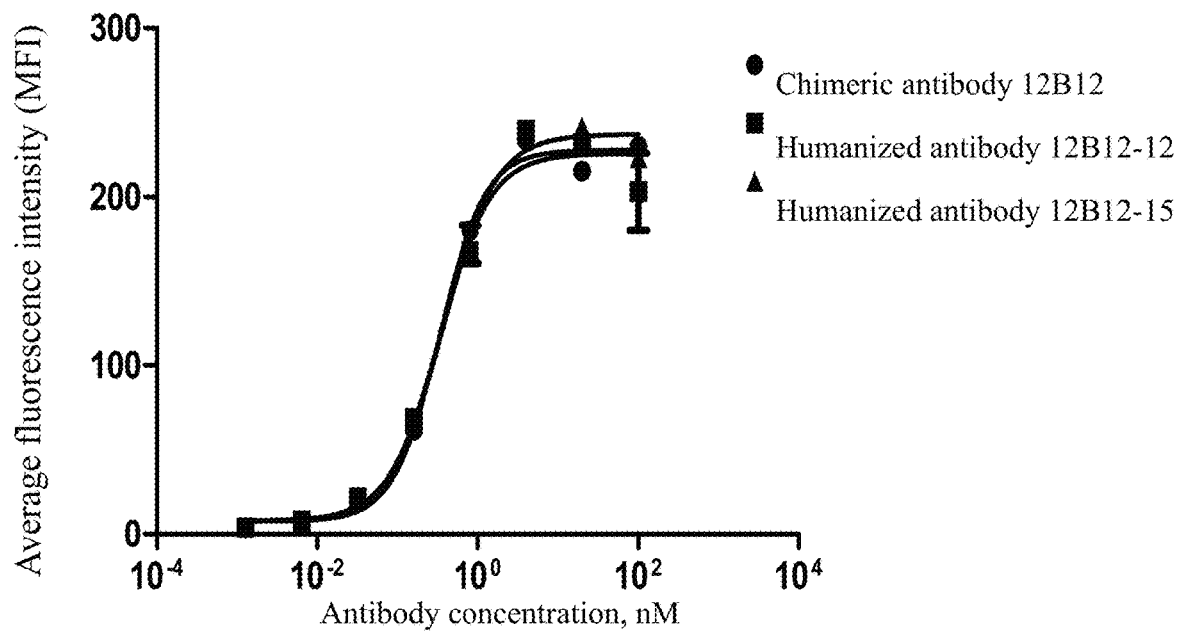

FIG. 9A. FACS detection of the binding of the humanized 12B12 variant to the stable transfected cell line CHOK1-hTPBG with surface expressed human TPBG protein.

Figure 9B:
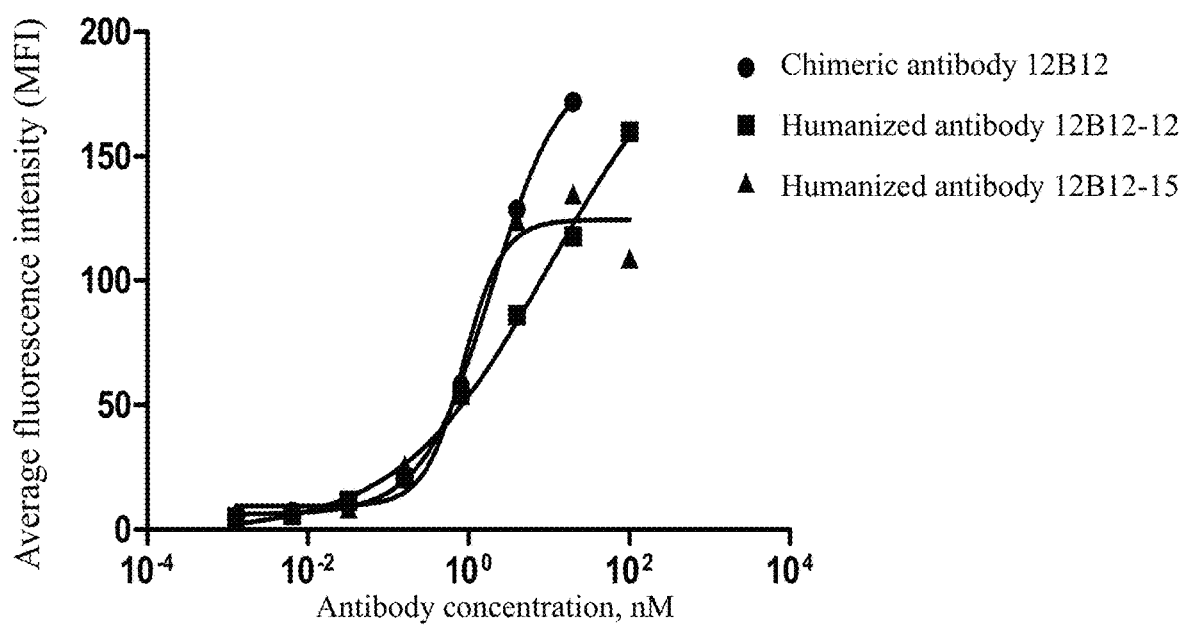

FIG. 9B. FACS detection of the binding of the humanized 12B12 variant to the stable transfected cell line CHOK1-cTPBG with surface-expressed cynomolgus TPBG protein.

Figure 9C:
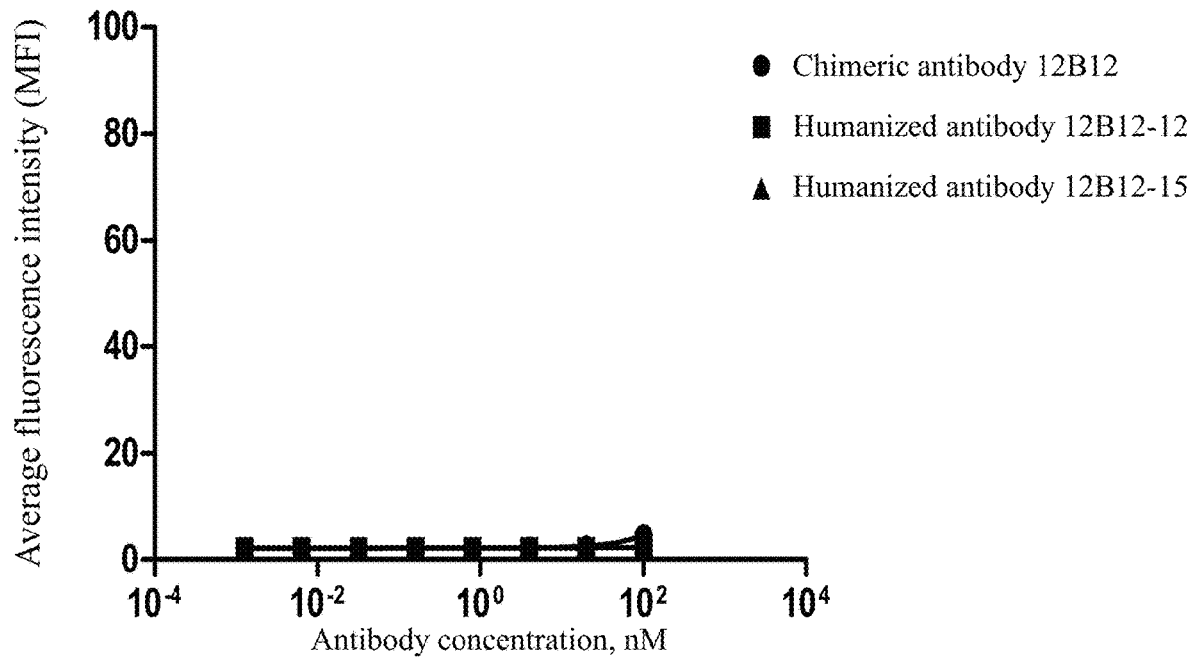

FIG. 9C. FACS detection of the binding of the humanized 12B12 variant to the stable transfected cell line CHOK1-cTPBG with surface-expressed mouse TPBG protein.

Figure 9D:
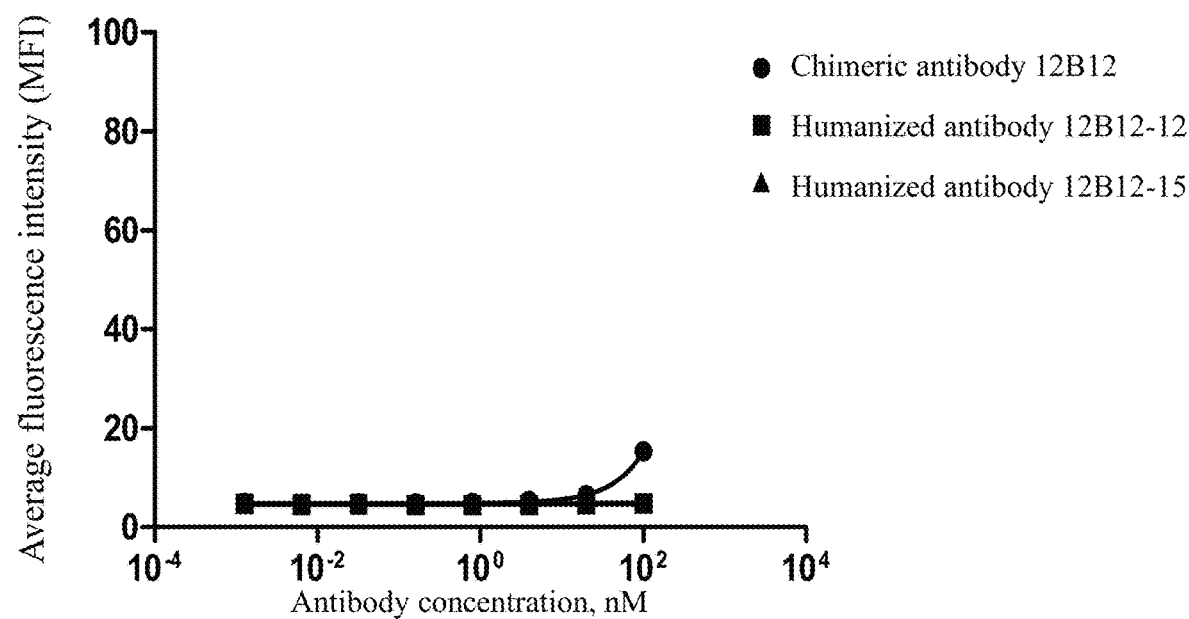

FIG. 9D. FACS detection of the binding of the humanized 12B12 variant to the TPBG negative cell line CHO-k1.

Figure 10A:
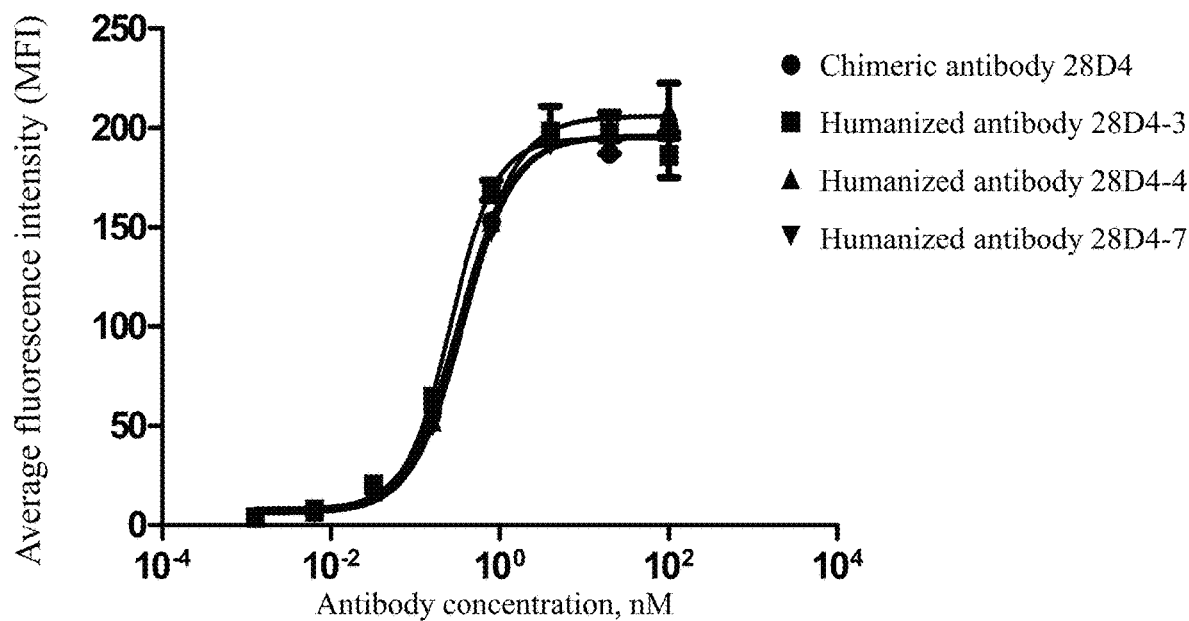

FIG. 10A. FACS detection of the binding of the humanized 28D4 variant to the stable transfected cell line CHOK1-hTPBG with surface-expressed human TPBG protein.

Figure 10B:
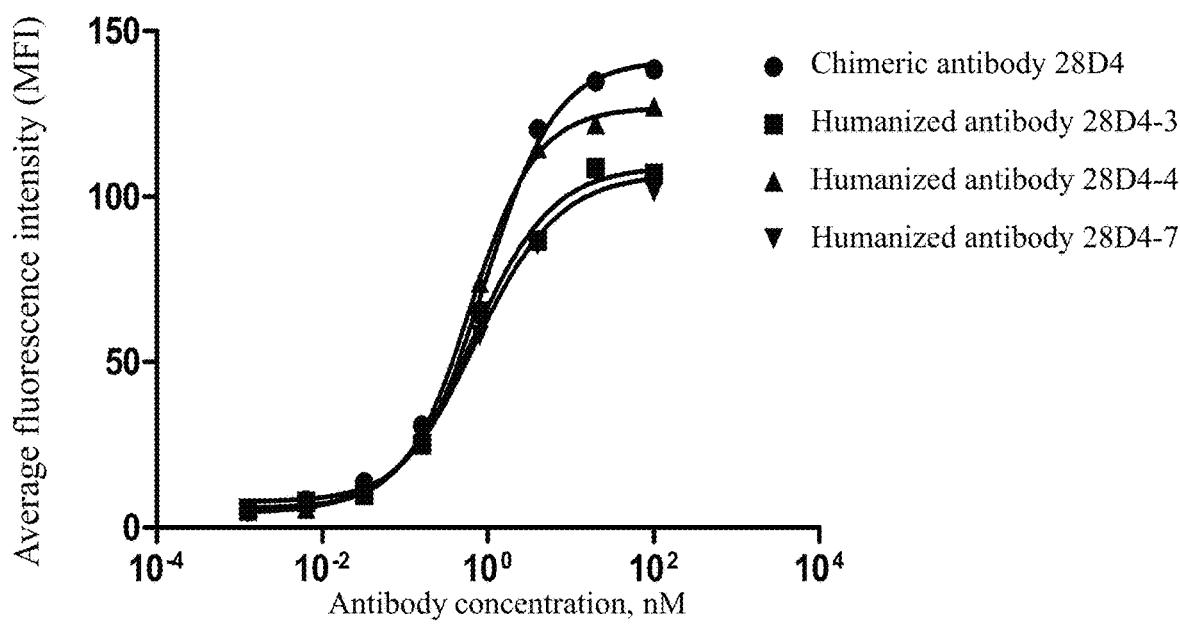

FIG. 10B. FACS detection of the binding of the humanized 28D4 variant to the stable transfected cell line CHOK1-cTPBG with surface-expressed cynomolgus TPBG protein.

Figure 10C:
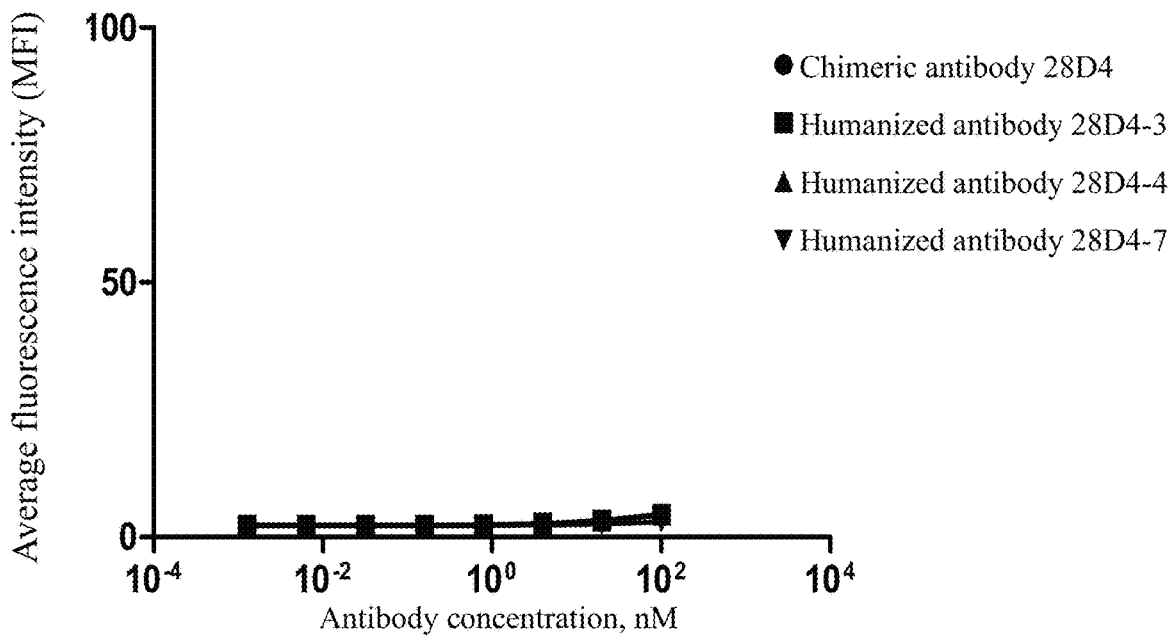

FIG. 10C. FACS detection of the binding of the humanized 28D4 variant to the stable transfected cell line CHOK1-cTPBG with surface-expressed mouse TPBG protein.

Figure 10D:
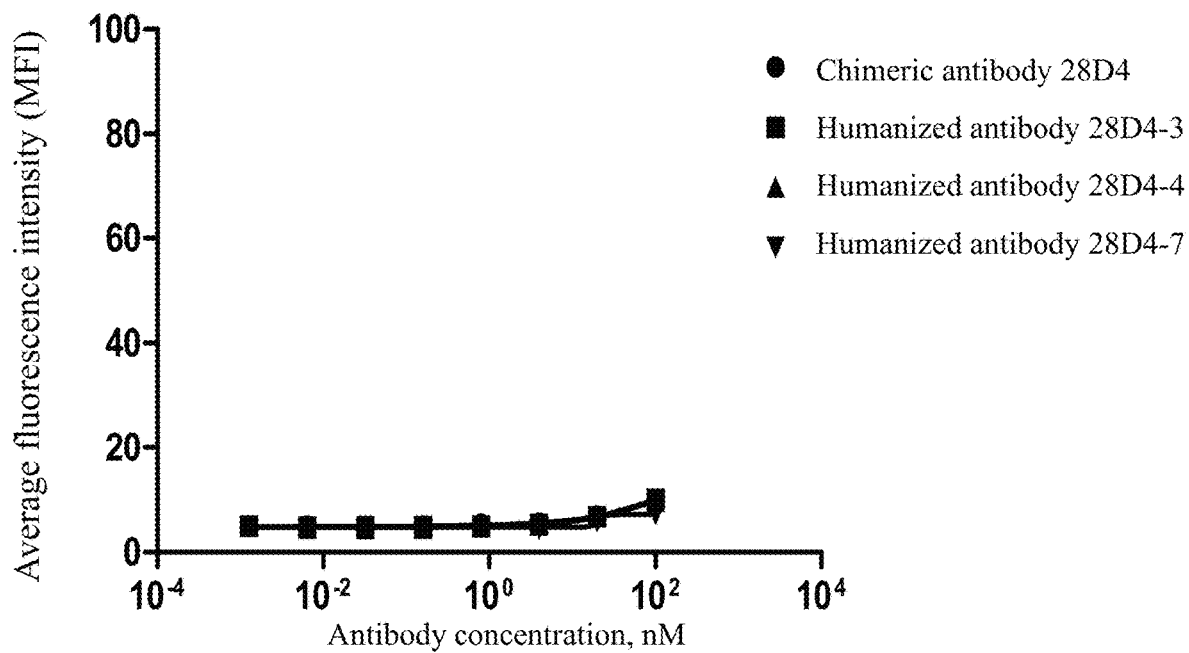

FIG. 10D. FACS detection of the binding of the humanized 28D4 variant to the TPBG negative cell line CHO-k1.

Figure 11A:
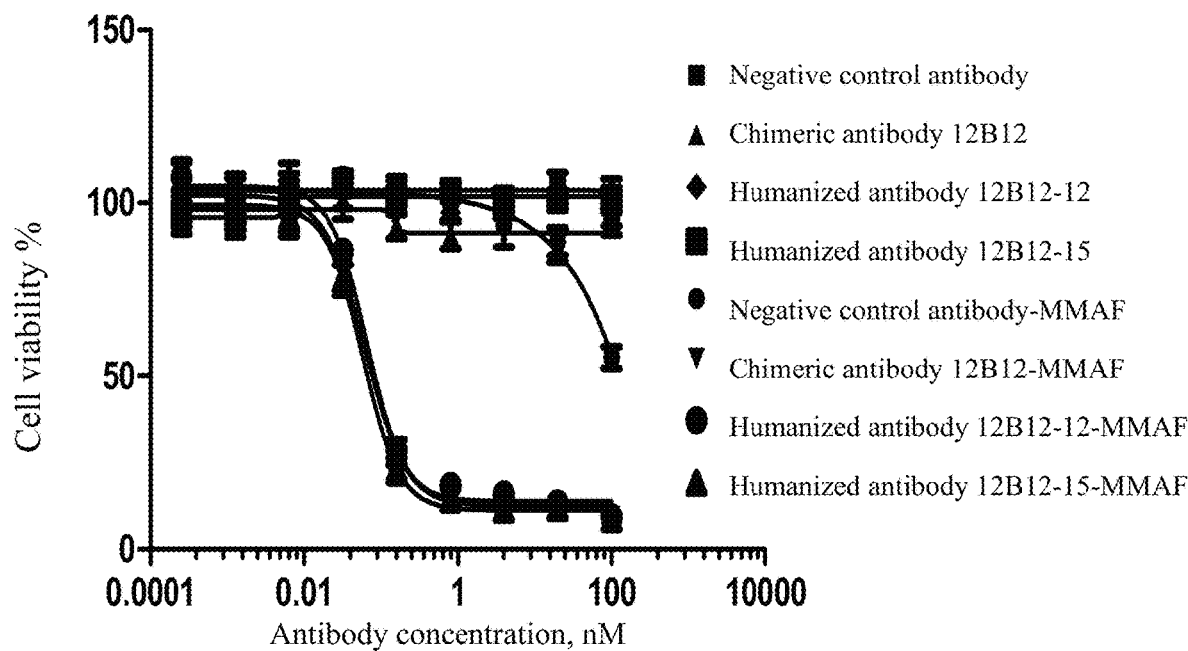

FIG. 11A. Detection of the cytotoxic activity of the humanized antibody 12B12 variant and its antibody-drug conjugate against the TPBG positive tumor cell line NCI-H1568.

Figure 11B:
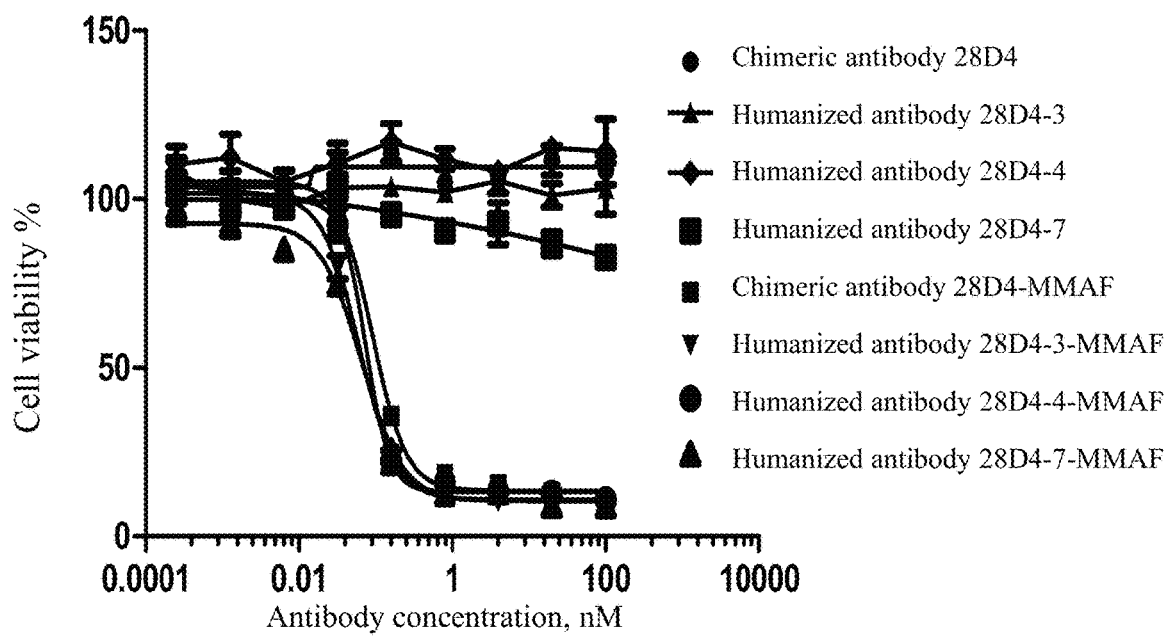

FIG. 11B. Detection of the cytotoxicity of the humanized antibody 28D4 variant and its antibody-drug conjugate against the TPBG positive tumor cell line NCI-H1568.

Figure 12A:
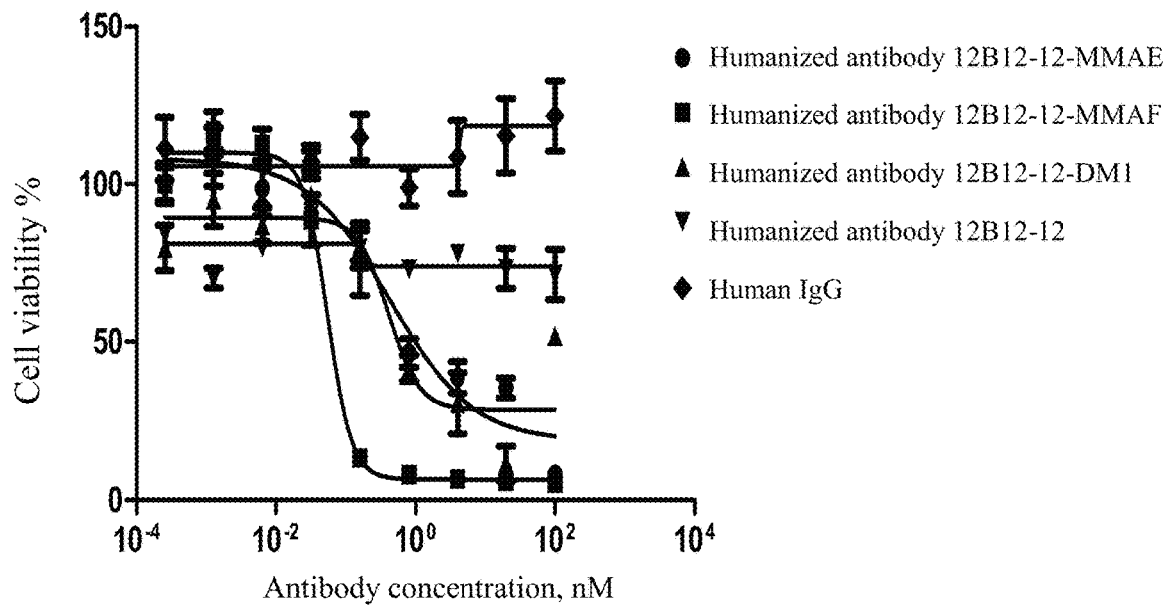

FIG. 12A. Detection of the cytotoxicity of the humanized TPBG antibody-drug conjugate against the TPBG positive tumor cell line NCI-H1568.

Figure 12B:
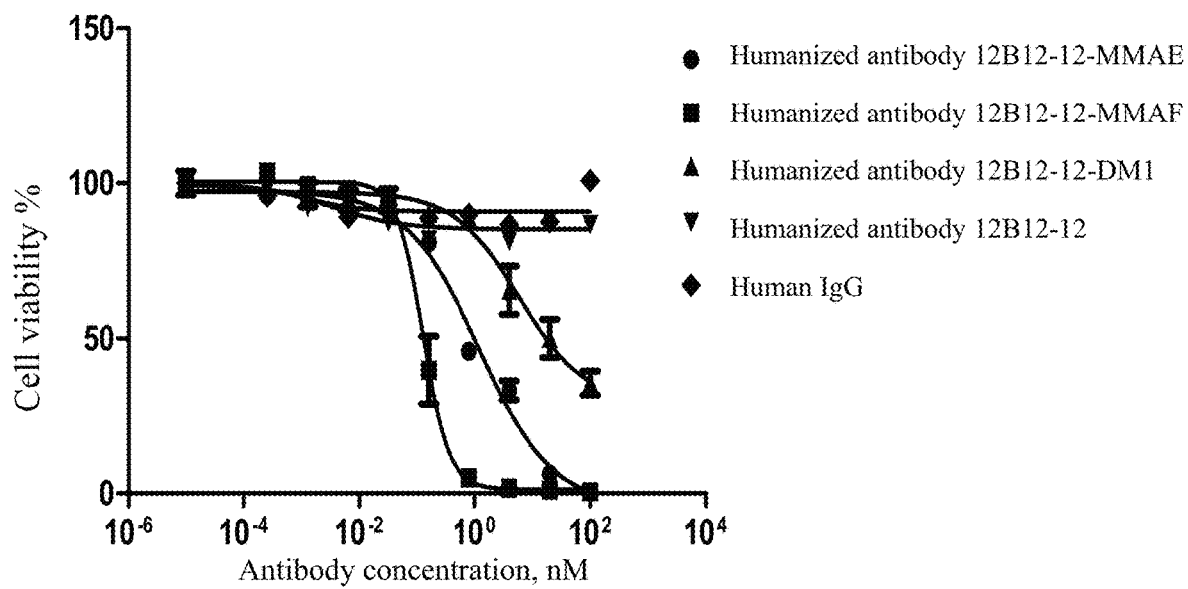

FIG. 12B. Detection of the cytotoxicity of the humanized TPBG antibody-drug conjugate against the TPBG weakly positive tumor cell line NCI-H1975.

Figure 12C:
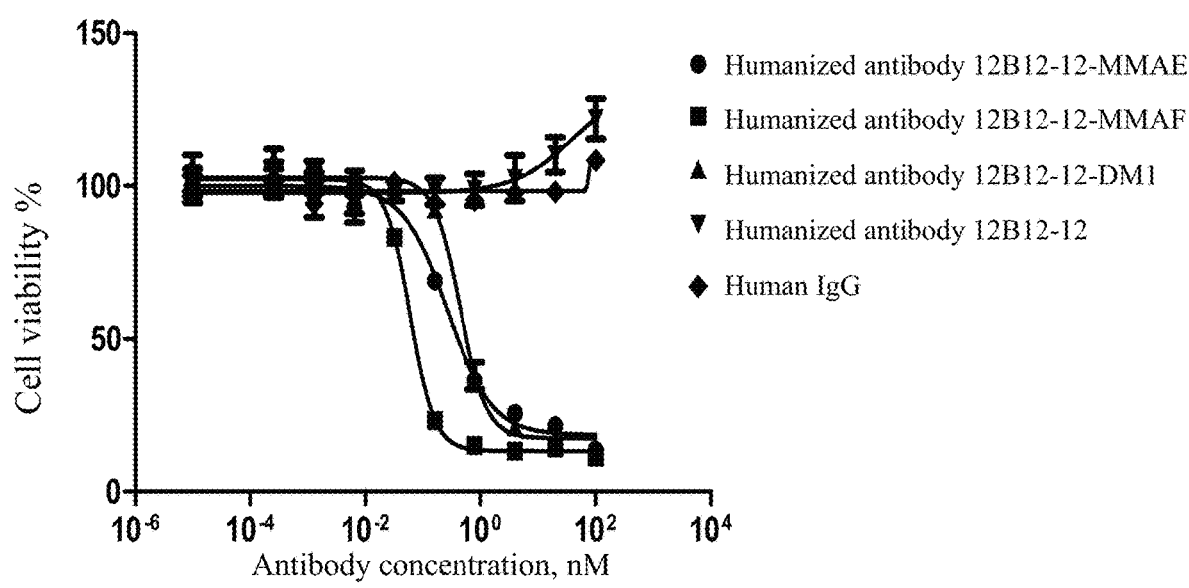

FIG. 12C. Detection of the cytotoxicity of the humanized TPBG antibody-drug conjugate against the TPBG positive tumor cell line MDA-MB-468.

Figure 13A:
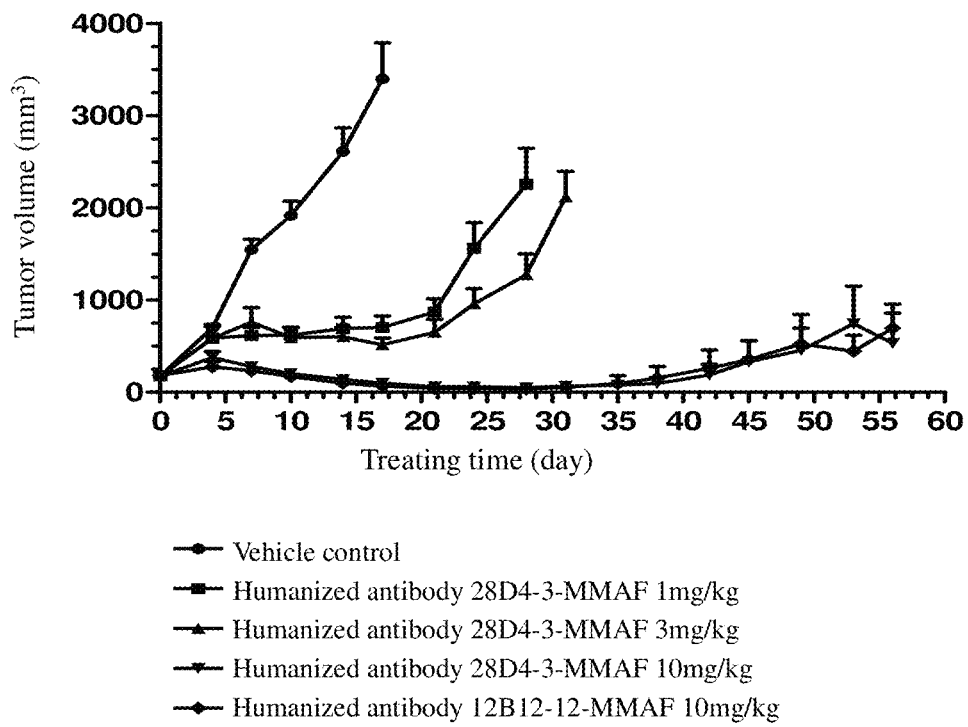

FIG. 13A. Variation of tumor volume under different doses of humanized 28D4-3-MMAF antibody-drug conjugates are shown by in vivo pharmacodynamics experiment of NCI-H1975 mouse xenograft model.

Figure 13B:
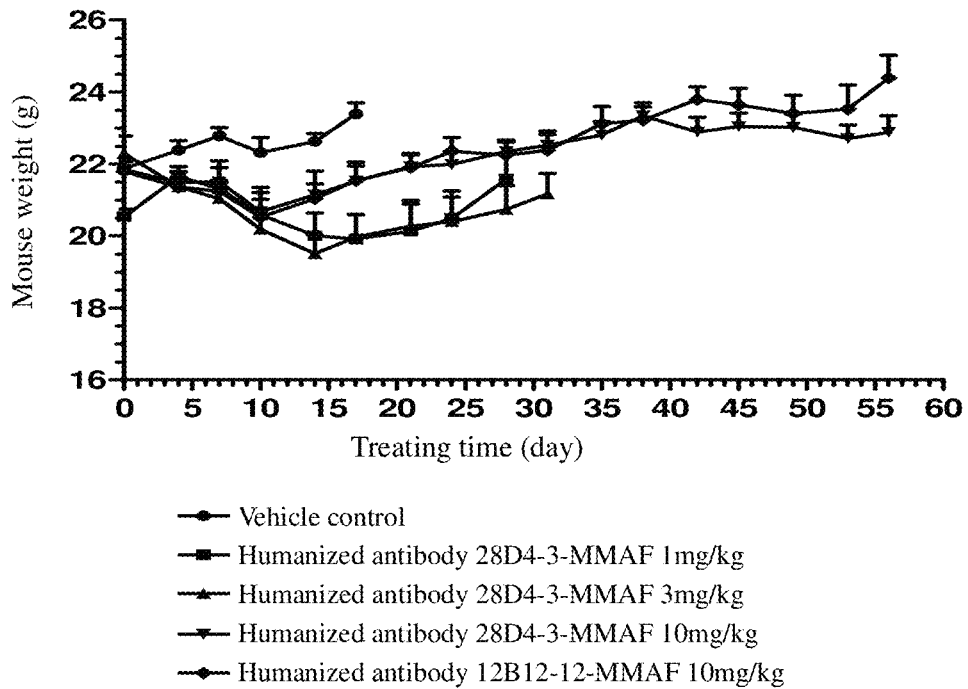

FIG. 13B. Variation of mouse weight under different doses of humanized 28D4-3-MMAF antibody-drug conjugates are shown by in vivo pharmacodynamic experiment of the NCI-H1975 mouse xenograft model.

Figure 14A:
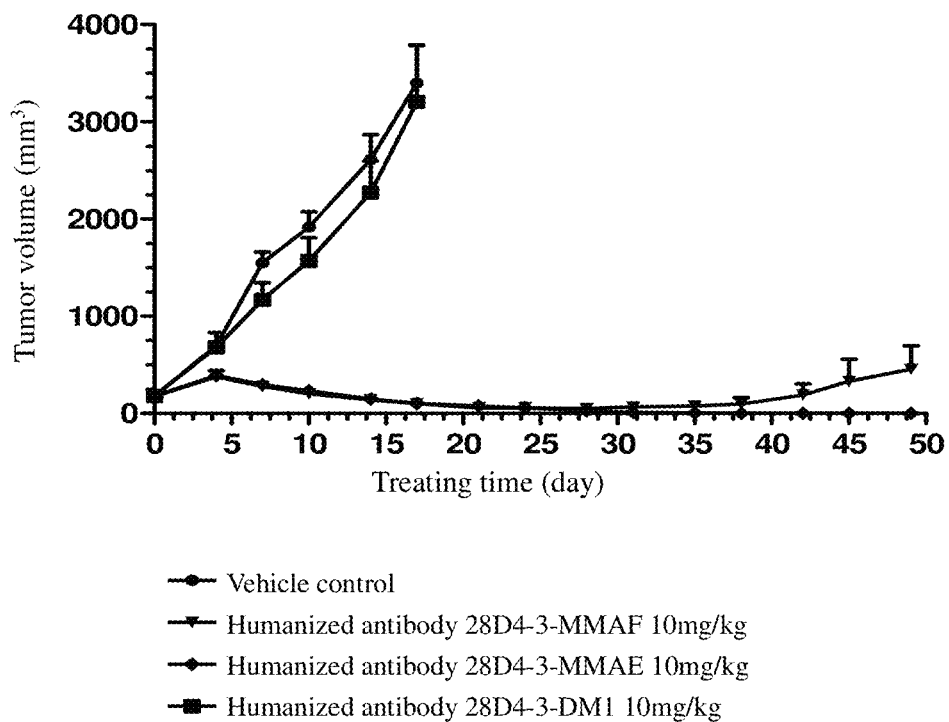

FIG. 14A. Variation of tumor volume under same dose of humanized 28D4-3-MMAF, 28D4-3-MMAE and 28D4-3-DM1 antibody-drug conjugates coupled to different linker-toxins are shown by in vivo pharmacodynamic experiment of NCI-H1975 mouse xenograft model.

Figure 14B:
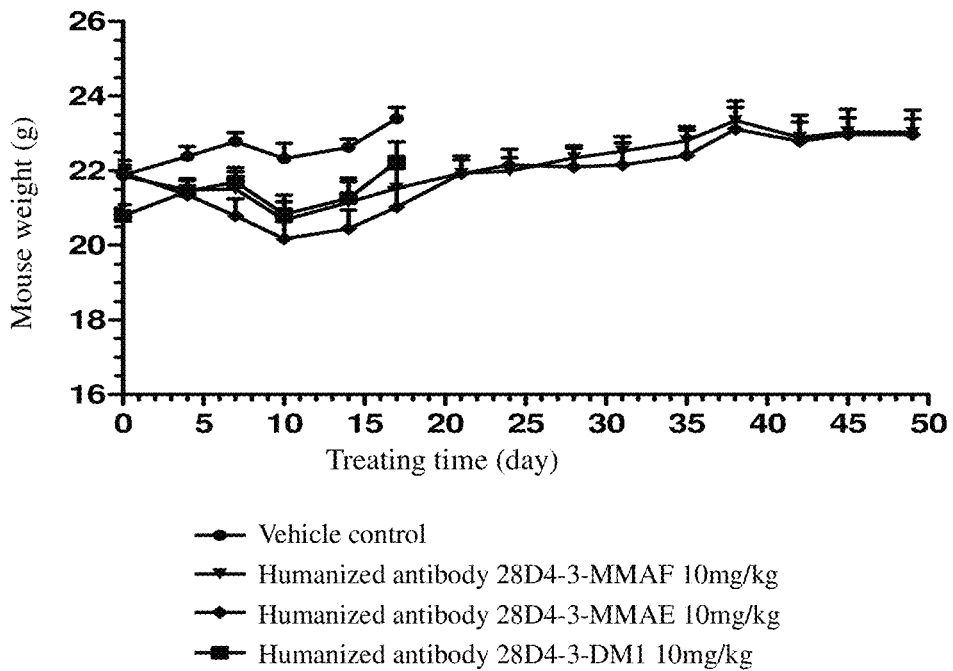

FIG. 14B. Variations of mouse weight under same dose of humanized 28D4-3-MMAF, 28D4-3-MMAE and 28D4-3-DM1 antibody-drug conjugates coupled to different linker-toxins are shown by in vivo pharmacodynamic experiment of NCI-H1975 mouse xenograft model in vivo pharmacodynamic experiment of NCI-H1975 mouse xenograft tumor model.

Figure 15A:
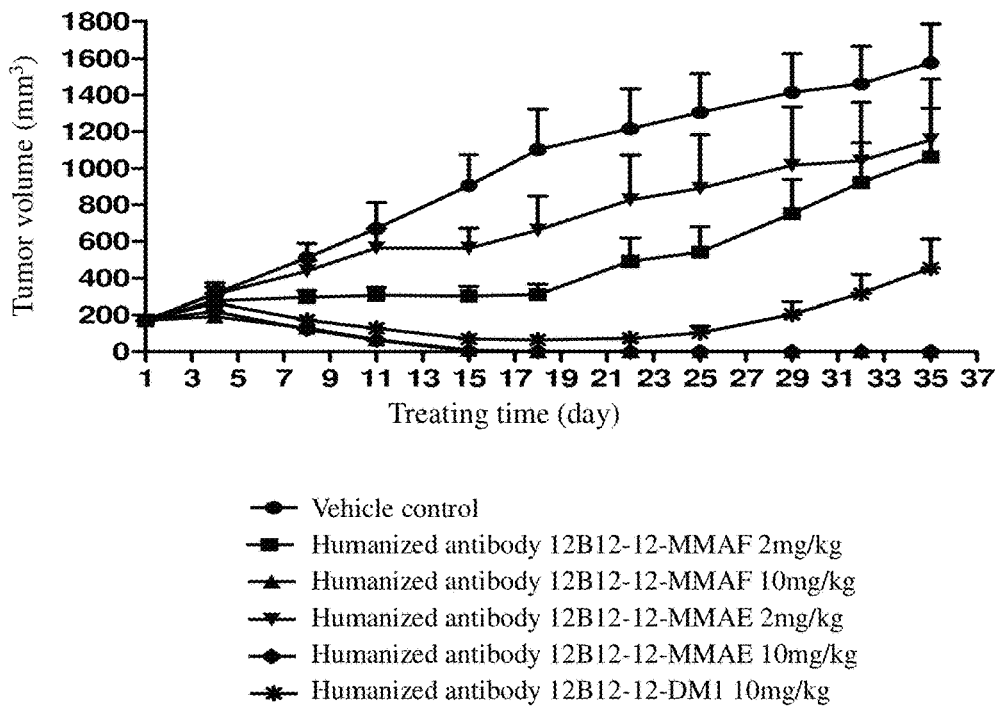

FIG. 15A. Variation of tumor volume under different doses of humanized 12B12-12-MMAF, 12B12-12-MMAE and 12B12-12-DM1 antibody-drug conjugates coupled to different linker-toxins are shown by in vivo pharmacodynamic experiment of NCI-H1568 mouse xenograft tumors model.

Figure 15B:
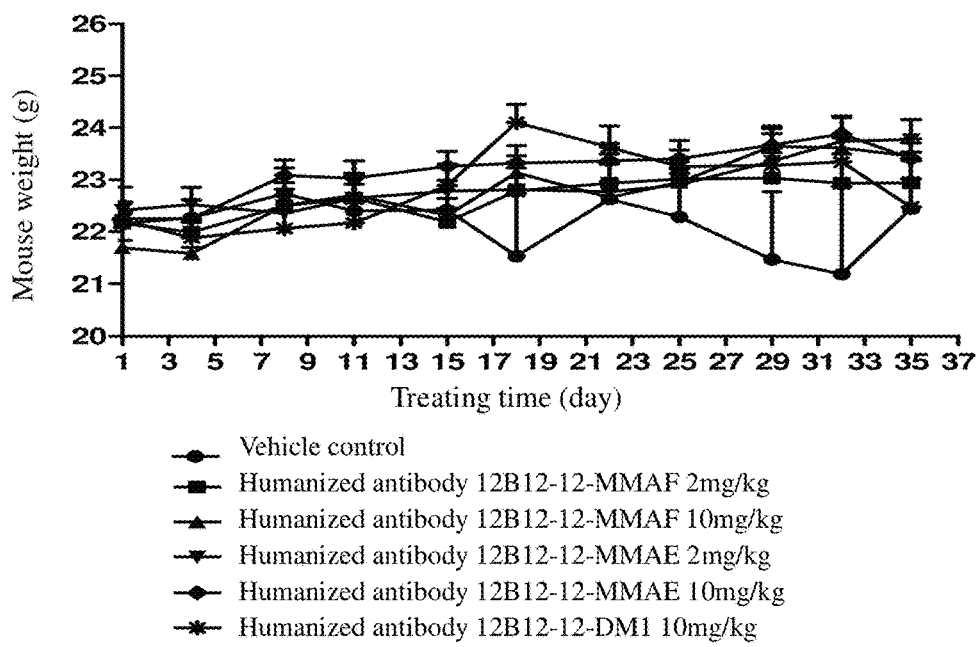

FIG. 15B. Variations of mouse weight under different doses of humanized 12B12-12-MMAF, 12B12-12-MMAE and 12B12-12-DM1 antibody-drug conjugates coupled to different linker-toxins are shown by in vivo pharmacodynamic experiment of NCI-H1568 mouse xenograft tumors model.

Figure 16A:
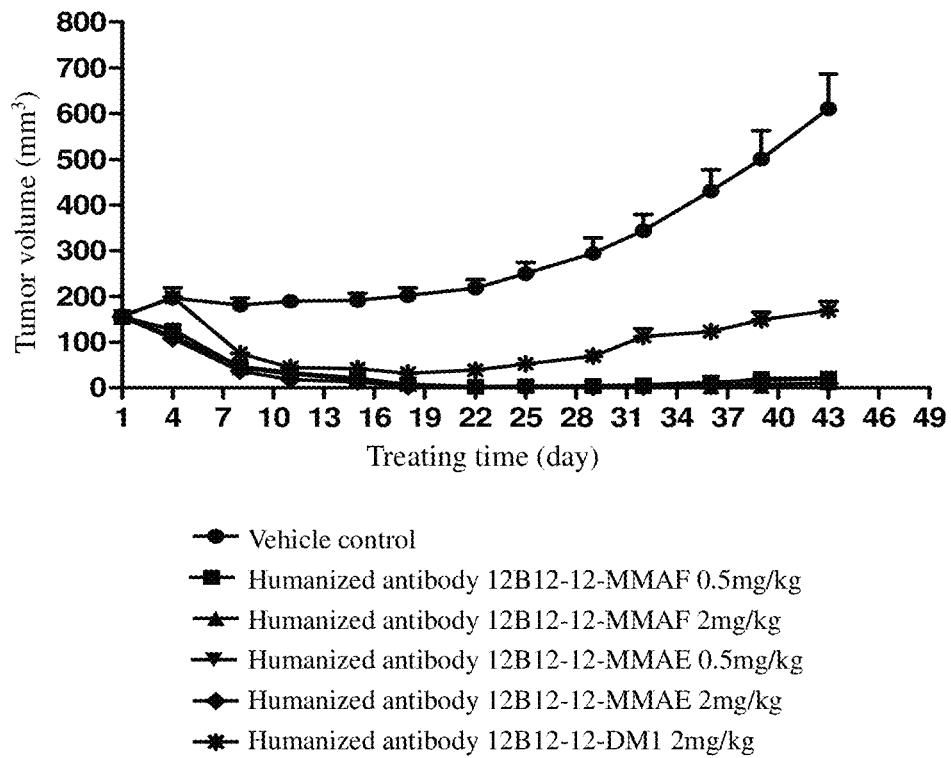

FIG. 16A. Variation of tumor volume under different doses of humanized 12B12-12-MMAF, 12B12-12-MMAE and 12B12-12-DM1 antibody-drug conjugates coupled to different linker-toxins are shown by in vivo pharmacodynamic experiment of MDA-MB-468 mouse xenograft tumor model.

Figure 16B:
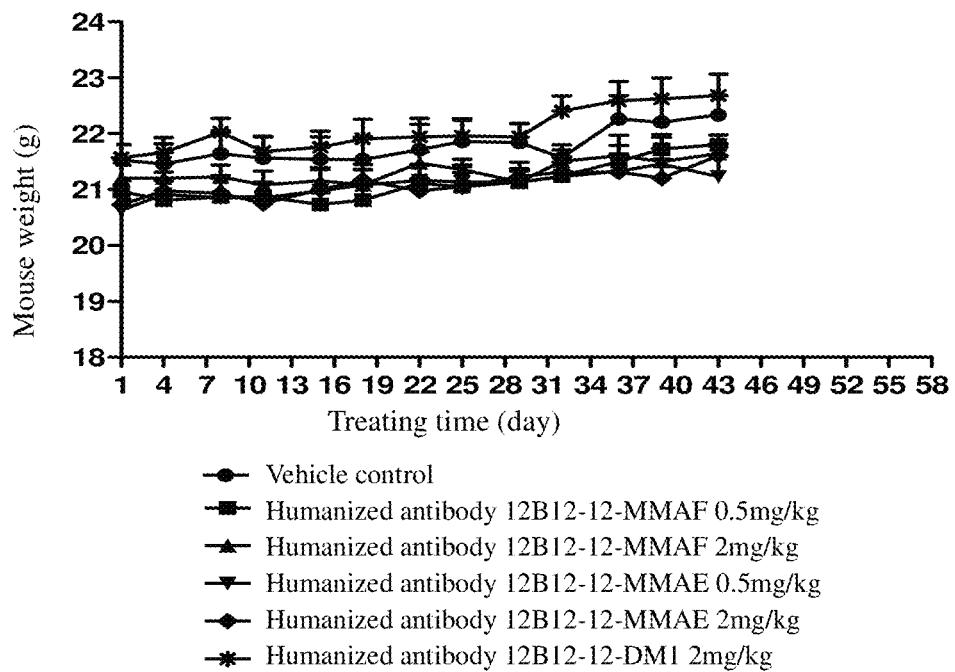

FIG. 16B. Variations of mouse weight under different doses of humanized 12B12-12-MMAF, 12B12-12-MMAE and 12B12-12-DM1 antibody-drug conjugates coupled to different linker-toxins are shown by in vivo pharmacodynamic experiment of MDA-MB-468 mouse xenograft tumor model.

Figure 17:
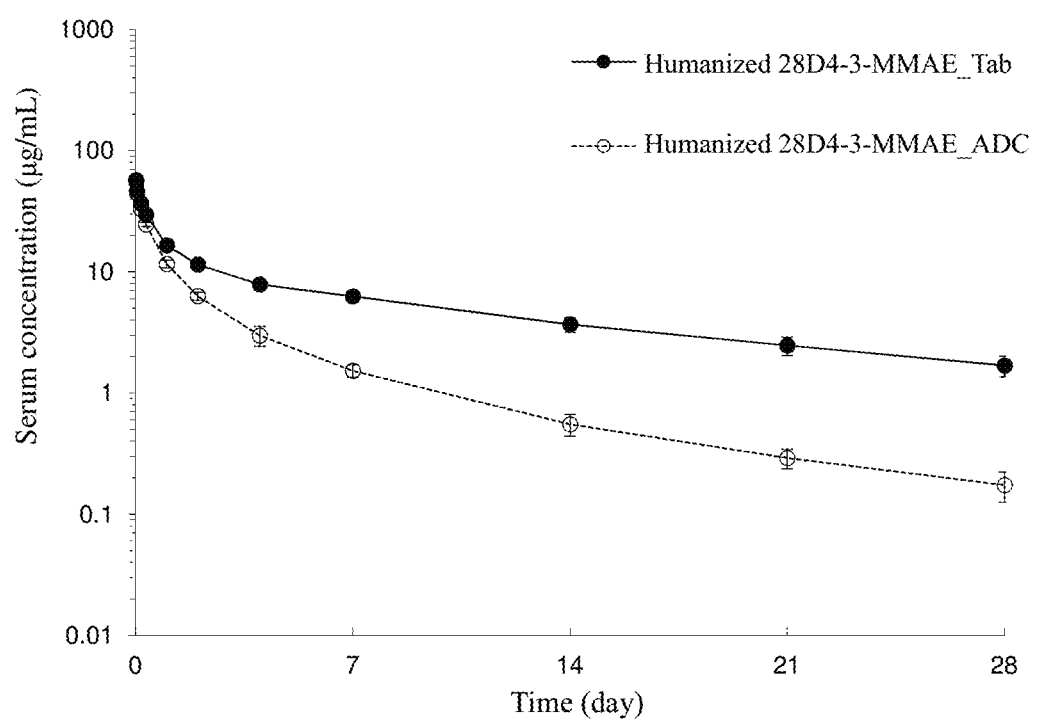

FIG. 17. Pharmacokinetic analysis of humanized 28D4-3-MMAE conjugates in rats.

Figure 18A:
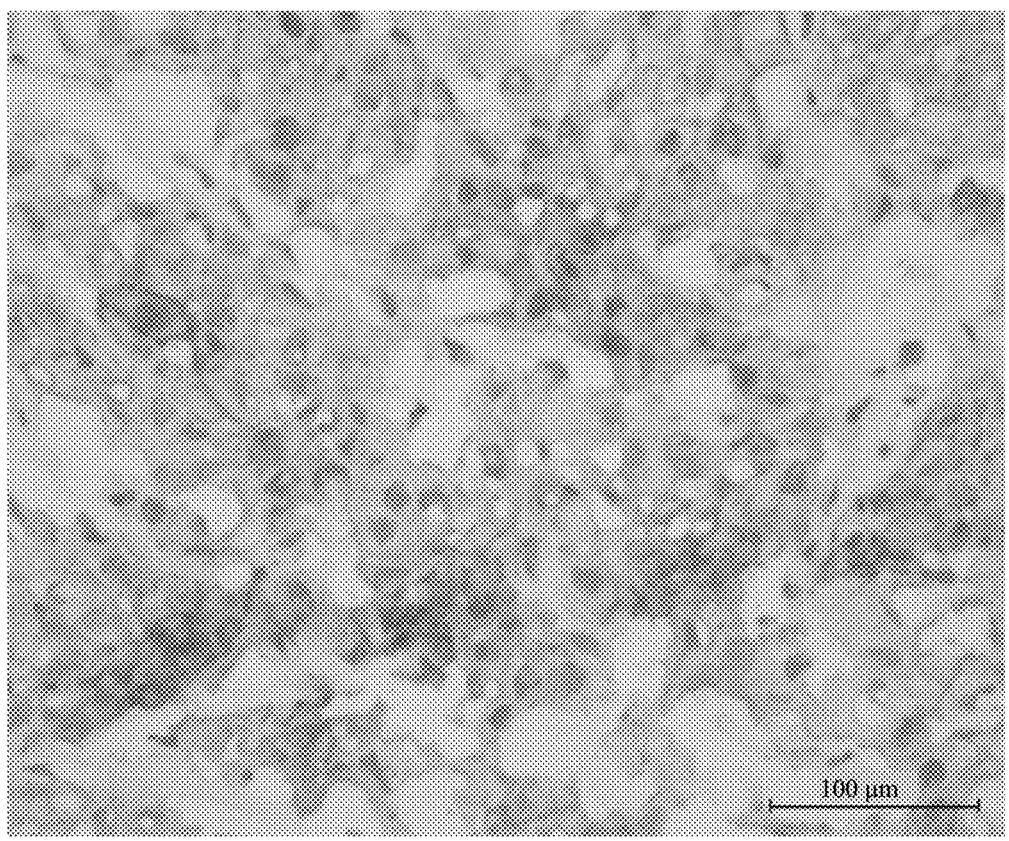

FIG. 18A. Staining of humanized anti-TPBG antibody 12B12-3 on PDX tumor tissue sections.

Figure 18B:
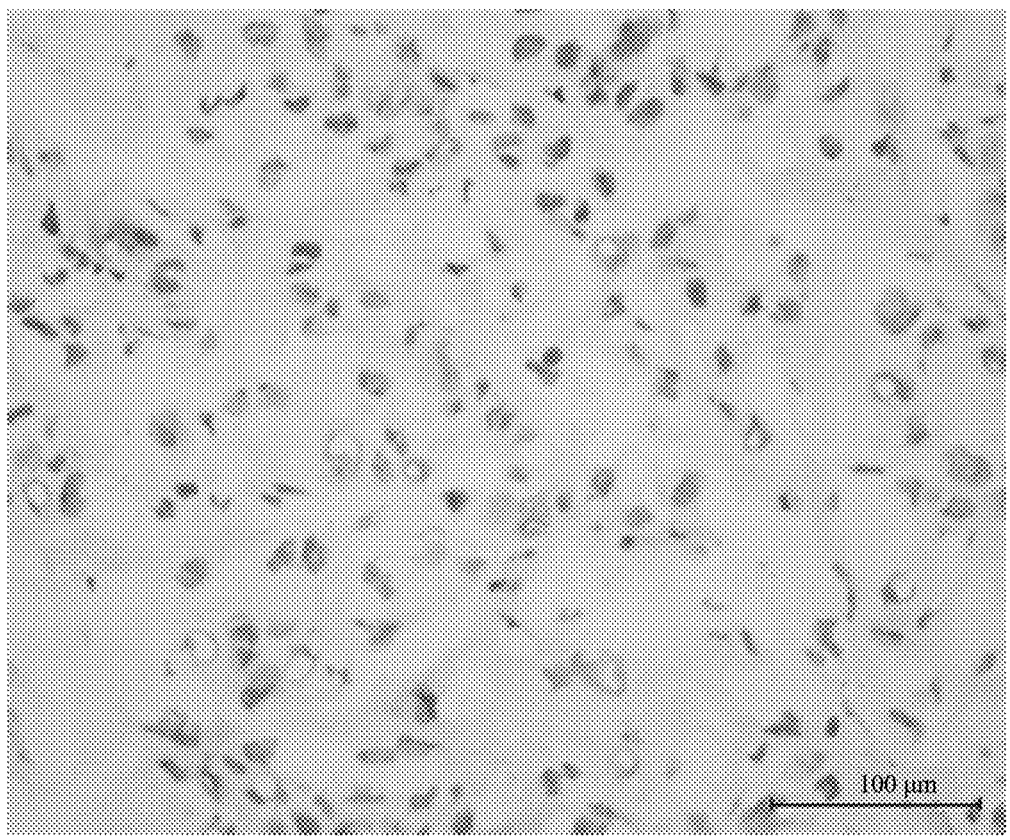

FIG. 18B. Staining of negative control antibody hIgG on PDX tumor tissue sections.

Figure 19A:
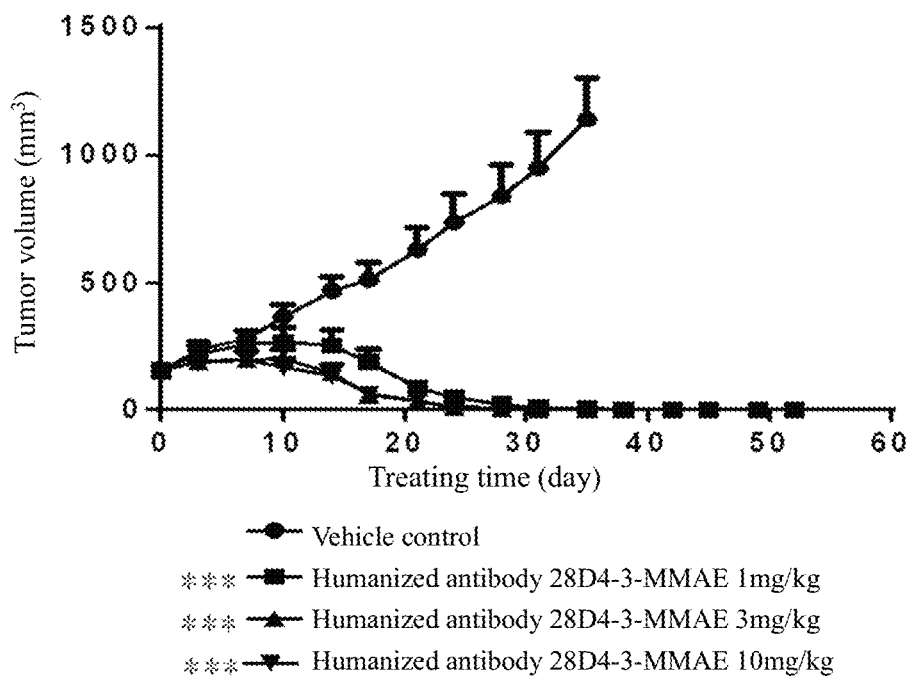

FIG. 19A. Variations of tumor volume under different doses of humanized 28D4-3-MMAE conjugates in non-small cell lung carcinoma patient-derived xenograft model (PDX).

Figure 19B:
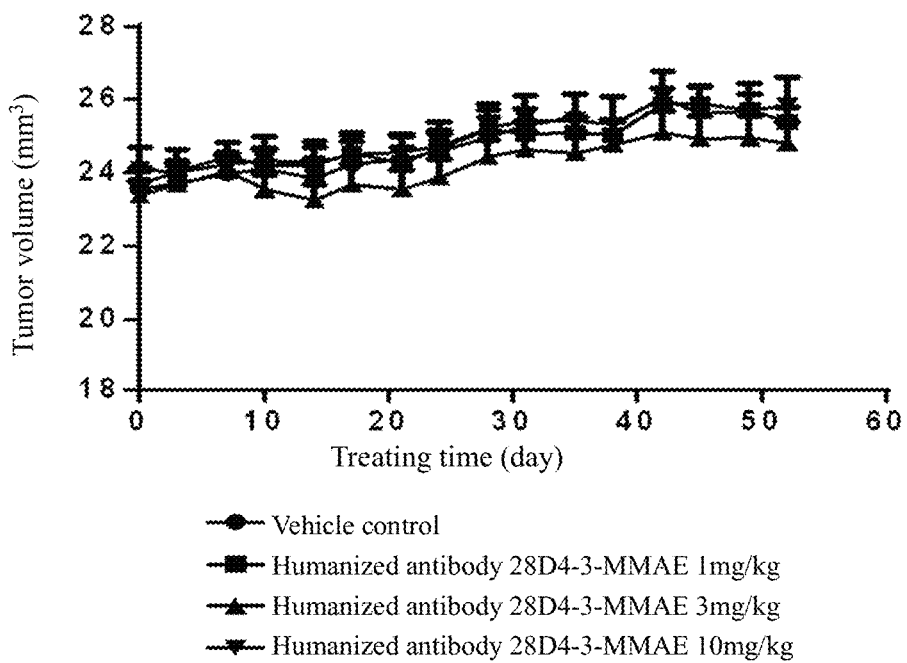

FIG. 19B. Variations of mouse weight under different doses of humanized 28D4-3-MMAE conjugates in non-small cell lung carcinoma patient-derived xenograft model (PDX).

Figure 20A:
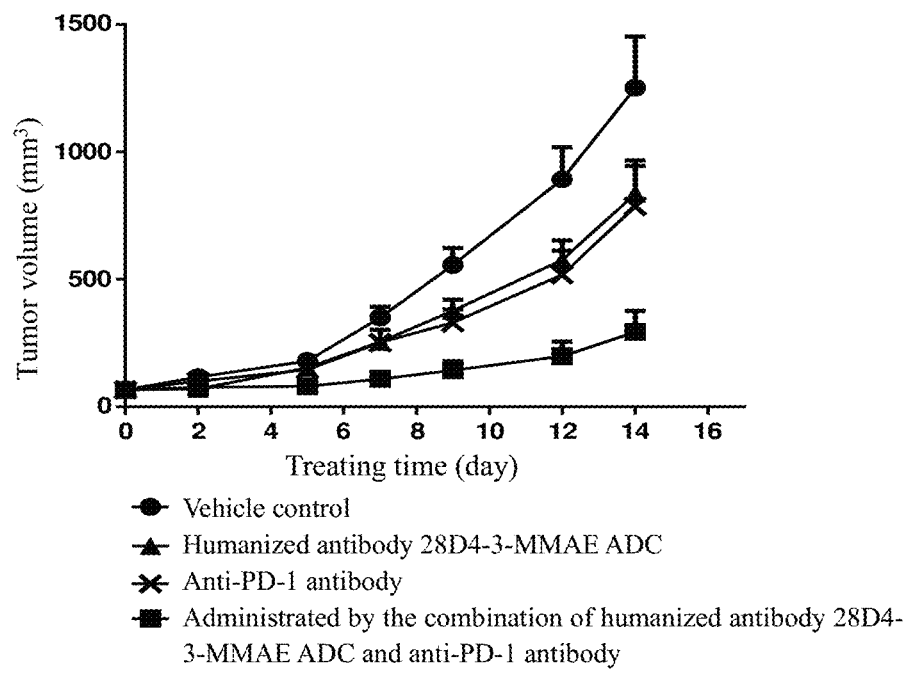

FIG. 20A. Tumor volume variations of mice that administrated by the combination of humanized 28D4-3-MMAE antibody-drug conjugate or/and anti-PD-1.

Figure 20B:
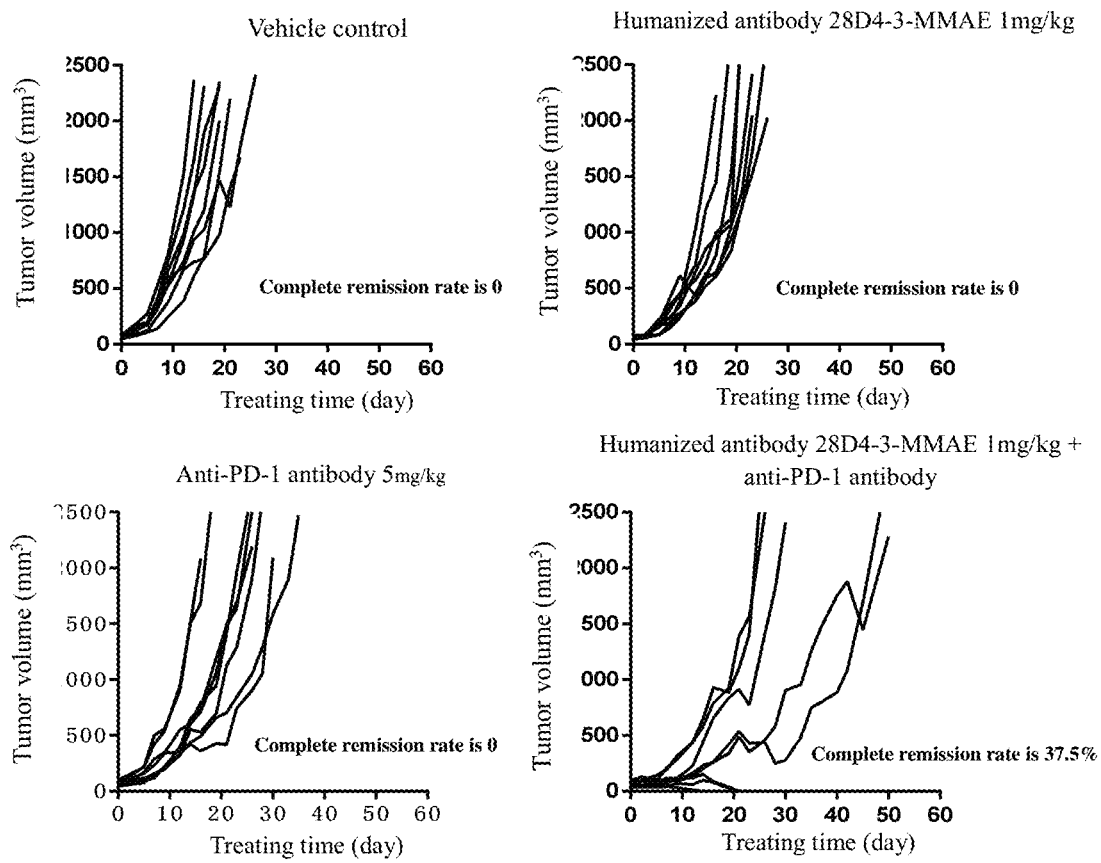

FIG. 20B. Lifetime diagram of mice survival showing the effect of the combination of humanized 28D4-3-MMAE antibody-drug conjugate or/and anti-PD-1.

Figure 20C:
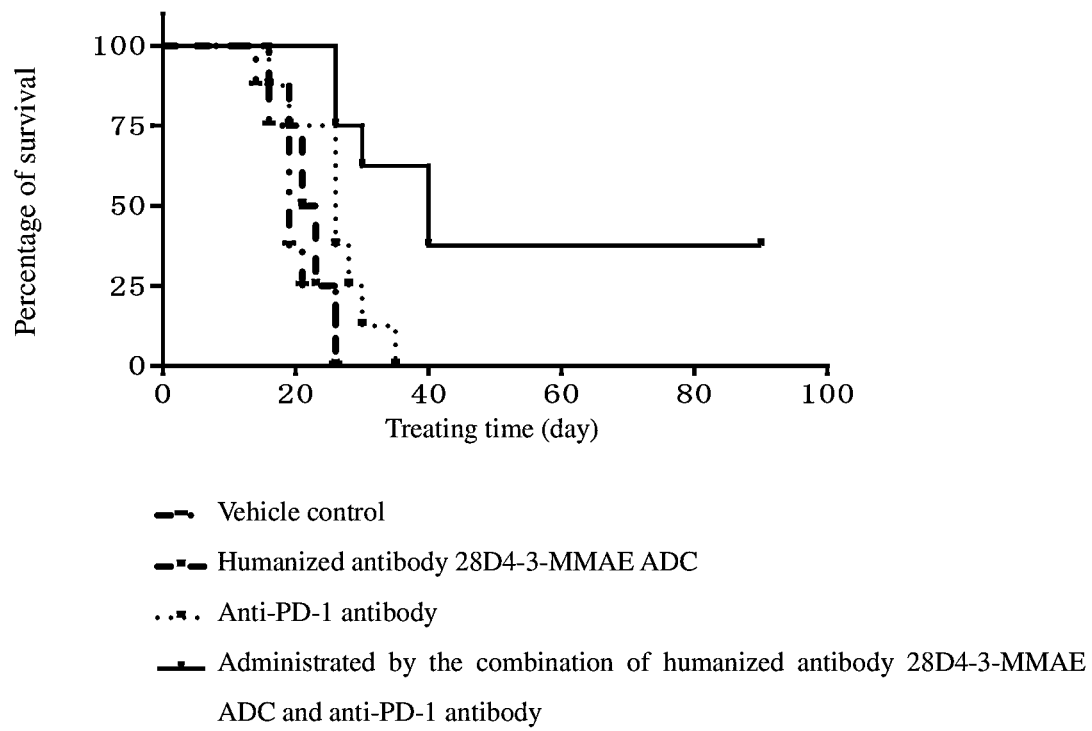

FIG. 20C. Variations of tumor volume of mice that administrated by the combination of humanized 28D4-3-MMAE antibody-drug conjugate or/and anti-PD-1.

Figure 20D:
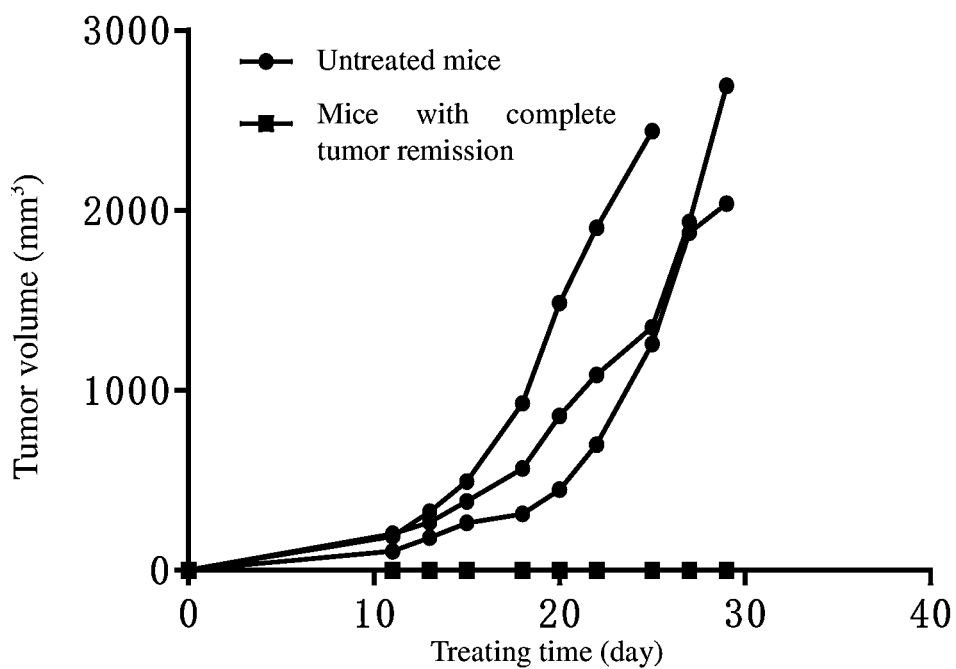

FIG. 20D. Administrated with the combination of humanized 28D4-3-MMAE antibody-drug conjugate or/and anti-PD-1, mice with complete tumor remission were re-inoculated with CT26-TPBG.

DETAILED DESCRIPTION OF THE PREFERRED EMBODIMENT

The present disclosure is not to be limited in scope by the specific embodiments described which are intended as single illustrations of individual aspects of the disclosure. The experimental methods in the following examples which do not specify the specific conditions are selected according to conventional methods and conditions, or according to the product specifications.

The room temperature described in the examples is a conventional room temperature in the art, generally 10 to 30° C.

Unless otherwise specified, the PBS described in the examples is PBS phosphate buffer, pH 7.2.

Embodiment 1 Preparation of Chimeric Antibodies 12B12 and 28D4 and Humanized TPBG Antibodies 1. Preparation of Mouse Antibodies 12B12 and 28D4

(1) Preparation of Immunogen a (Human TPBG-hFc Protein)

A nucleotide sequence containing the nucleic acid encoding amino acid sequence 32-355 (Ser32-Ser355) of the extracellular domain of human TPBG protein (wherein the accession number of the nucleotide sequence encoding human TPBG protein is Genbank ID: AAH37161.1) was cloned into a pCpC vector with human IgG Fc fragment (purchased from Invitrogen, V044-50) and the plasmid was prepared according to established standard molecular biology protocol. For specific methods, please refer to Sambrook, J., Fritsch, E. F., and Maniatis, T. (1989). Molecular Cloning: A Laboratory Manual, Second Edition (Plainview, N.Y.: Cold Spring Harbor Laboratory Press). HEK293 cells (purchased from Invitrogen) were transiently transfected (polyether imide, PEI, purchased from Polysciences) and expanded at 37° C. using FreeStyle™293 (purchased from Invitrogen). After 4 days, cell culture was harvested, cell pellets were removed by centrifugation and culture supernatant containing the extracellular domain of TPBG protein was obtained. The culture supernatant was loaded onto protein A affinity chromatography column (Mabselect Sure, purchased from GE Healthcare), and the change in ultraviolet absorption (A280 nm) was monitored using a UV detector. Once the sample was loaded, the protein A affinity chromatography column was equilibrated with PBS buffer (pH7.2) until the ultraviolet absorption value returned to baseline. Subsequently, elution was performed using 0.1M glycine hydrochloride acid (pH2.5), and hFc tagged TPBG protein (i.e. human TPBG-hFc) eluting from the protein A affinity chromatography column was harvested and dialyzed against PBS (pH 7.2) at 4° C. overnight in refrigerator. The dialyzed protein was aseptically filtered through 0.22 μm and stored at −80° C. in aliquots, and purified human TPBG-hFc protein was then obtained.

Prior to being used, human TPBG-hFc protein was subjected to a series of quality control tests, e.g. protein concentration, purity, molecular weight, biological activity, etc., and it was found that the human TPBG-hFc protein was qualified and can be used as the antigen for the subsequent preparation of TPBG antibodies.

(2) Preparation of Immunogen B

The nucleotide sequence encoding the full-length amino acid sequence of human TPBG (wherein the Genbank accession number of the nucleotide sequence encoding human TPBG protein is Genbank ID: AAH37161.1) was cloned into the pIRES vector (purchased from Clontech) and the plasmid of which was prepared. Recombinant plasmid (PEI, purchased from Polysciences) was transfected to HEK293 cell line (purchased from ATCC), and the transfected cells were selectively cultured in 0.5 g/ml DMEM culture medium containing 10% (w/w) fetal bovine serum for two weeks. Subcloning was performed using limiting dilution assay in 96-wells plate and the plate were cultured at 37° C., 5% (v/v) $CO_2$, and after two weeks a portion of the wells containing monoclones were selected and expanded into 6-wells plate. The expanded clones were screened by FACS analysis using commercially available TPBG antibody (purchased from Sigma, Lot NO: SAB1404485). Robust monoclonal cell lines with high fluorescence intensity were selected and further expanded and cryopreserved in liquid nitrogen, i.e., immunogen B was obtained. The specific selection results were shown in Table 2. The IgG isotype control herein was mouse IgG. Table 2 indicates that a series of TPBG expression-positive HEK 293 cell lines have been prepared. Table 2 demonstrates that 293F-hTPBG 5E5 is a cell strain with high level of TPBG expression, wherein the MFI of the cells labeled with anti-TPBG antibody is 280.5, and the migration rate of the cells is 98.5%.

TABLE 2

Results of FACS screening of HEK293 cells transfected with human TPBG protein

| NO | Clone number of transfected cell | Cellular MFI IgG isotype control | TPBG antibody |
|---|---|---|---|
| 1 | 293F-hTPBG 4E1 | 5.2 | 145.0 |
| 2 | 293F-hTPBG 4A8 | 3.1 | 33.4 |
| 3 | 293F-hTPBG 4A9 | 6.3 | 203.9 |
| 5 | 293F-hTPBG 4B9 | 6.3 | 126.1 |
| 6 | 293F-hTPBG 4C3 | 3.2 | 27.2 |
| 7 | 293F-hTPBG 4C5 | 5.6 | 171.5 |
| 8 | 293F-hTPBG 4E1 | 4.8 | 91.8 |
| 9 | 293F-hTPBG 4F9 | 3.9 | 47.7 |
| 10 | 293F-hTPBG 4G1 | 4.0 | 131.2 |
| 11 | 293F-hTPBG 4G6 | 3.1 | 31.8 |
| 12 | 293F-hTPBG 4H12 | 4.0 | 9.5 |
| 13 | 293F-hTPBG 5E6 | 2.6 | 13.2 |
| 15 | 293F-hTPBG 5A11 | 4.6 | 166.5 |
| 16 | 293F-hTPBG 5A9 | 5.0 | 53.2 |
| 17 | 293F-hTPBG 5C12 | 3.7 | 75.4 |
| 18 | 293F-hTPBG 5D4 | 3.0 | 70.6 |
| 19 | 293F-hTPBG 5E5 | 5.6 | 280.5 |
| 20 | 293F-hTPBG 5G11 | 4.1 | 11.3 |
| 21 | 293F-hTPBG 5G8 | 6.0 | 167.8 |
| 22 | 293F-hTPBG 5H6 | 3.0 | 36.4 |

(3) Preparation of Hybridoma Cells and Screening of Antibody

A. Immunization with Immunogen A

BALB/cAnNCrl mice or SJL/JorllcoCrl mice (both purchased from SLAC Co. Ltd, Shanghai) aged 6-8 weeks were raised in SPF condition. For the primary immunization, 0.25 ml of immunogen A prepared in step 1 being emulsified with Freund's complete adjuvant, i.e. 50 mg of immunogen A per mouse was intraperitoneally injected. For booster immunization, 0.25 ml of immunogen A being emulsified with Freund's incomplete adjuvant, i.e. 50 mg of immunogen A per mouse was intraperitoneally injected. The interval between the primary immunization and first booster is two weeks and the interval between each booster is three weeks. Blood was collected 1 week after each booster, and the antibody titer and specificity of the immunogen in serum were tested by ELISA and FACS. The results were shown in Table 3. Table 3 indicates that the serums of mouse immunized with immunogen A have different degrees of binding to immunogen A and show antigen-antibody reaction, wherein the highest dilution rate is around one million. The blank control is 1% (w/w) BSA, and batch refers to the type of mouse serum at day 7 after the second booster immunization. The data in the table refers to OD450 nm values.

TABLE 4

Detection of antibody titers in the serum of Balb/c mice immunized with TPBG protein using ELISA

| $OD_{450\ nm}$ | Serum Dilution Rate | | | | | | |
|---|---|---|---|---|---|---|---|
| Batch | 1:100 | $1:10^3$ | $1:10^4$ | $1:10^5$ | $1:10^6$ | $1:10^7$ | Blank |
| 731(TB2) | 2.8722 | 2.8084 | 2.8186 | 1.5772 | 0.3892 | 0.1201 | 0.0935 |
| 732(TB2) | 2.8715 | 2.8171 | 2.857 | 1.2767 | 0.2601 | 0.1353 | 0.0985 |
| 733(TB2) | 2.8411 | 2.8841 | 2.9258 | 1.7943 | 0.3336 | 0.1178 | 0.1418 |
| 734(TB2) | 2.8735 | 2.8503 | 2.861 | 1.3150 | 0.3052 | 0.1129 | 0.1365 |
| 735(TB2) | 2.9460 | 2.9859 | 2.9761 | 1.9749 | 0.4203 | 0.1463 | 0.1531 |

B. Immunization with Immunogen B

BALB/cAnNCrl mice or SJL/JorllcoCrl mice (both purchased from SLAC Co. Ltd, Shanghai) at 6-8 weeks of age were used and feed under SPF condition. According above-described step (2), the pIRES plasmid containing the nucleotide sequence encoding full-length human TPBG was transfected into HEK293 cell line and the recombinant HEK293 stable cell line containing human TPBG was obtained (293F-hTPBG 5E5) (transfection was performed using X-treme GENE HP DNA Transfection Reagent, purchased from Roche Co. Ltd, and operated according to the manual). Culture was expanded in T-75 flasks to a confluency of 90%, the culture medium was removed via pipetting, and cells were washed twice with DMEM basic medium (purchased from Invitrogen). Then cells were treated using enzyme-free cell dissociation buffer (purchased from Invitrogen) at 37° C. until the cells can be peeled off from the dish wall, and then harvested. The cells were washed twice with DMEM basic medium and diluted to a concentration of $2 \times 10^7$ cell/mL using phosphate buffer after cell counting. Every time, 0.5 ml of cell suspension was injected intraperitoneally into each mouse, and there was a two-week interval between the primary and booster immunizations. After that booster immunization was performed every three weeks. Blood sample was taken one week after every immunization except for the primary immunization, and the titers and specificity of the antibody in the serum was detected using FACS. After the second booster immunization, the antibody titer in the serum was over 1:1000.

Prior to the completion of steps A and B, each selected mice was injected intraperitoneally with 100 μg of purified immunogen A (for mice immunized with immunogen A) or recombinant HEK293 stable cell line containing human TPBG (for mice immunized with immunogen B) for the last immunization, and sacrificed 5 days later. Their spleen cells were harvested, and $NH_4OH$ was added to a final concentration of 1% (w/w) to lyse the erythrocyte that is mixed with splenocyte, follow by preparing a splenocyte suspension. Cells were washed for three times by centrifugation at 1000 rpm using DMEM basic medium, and the viable cells were mixed with mouse myeloma cell SP2/0 (purchased from ATCC) at a ratio of 5:1. Cell fusion was performed using a highly efficient electrofusion method (please refer to METHODS IN ENZYMOLOGY, VOL. 220). Fused cells were diluted in DMEM medium containing 20% (w/w) FBS and 1×HAT, and then plated onto 96-wells cell culture plates at the density of $1 \times 10^5$ cells/200 μl per well and cultured in 5% (v/v) $CO_2$ incubator at 37° C. After 14 days, the supernatants from the cell fusion plates were screened using ELISA and Acumen (microplate cytometry), and positive clones with an ELISA OD450 nm>1.0 and Acumen MFI value >100 were subjected to expansion culture in 24-wells plate. Positive clones were cultured in DMEM culture medium containing 10% (w/w) HT FBS at 37° C. in 5% (v/v) $CO_2$. The culture medium from the expansion culture in 24-wells plate was centrifuged after 3 days of culturing and the supernatant was collected and subjected to antibody subclass analysis. Its binding activity to TPBG protein and TPBG-positive cells were determined using ELISA and FACS.

Based on the screening results of 24-wells plate, hybridoma cells having ELISA OD450 nm>1.0, FACS MFI>50 and the hybridoma supernatant killing rate on TPBG-positive cells reaching 50% in indirect cytotoxicity assay were selected as eligible positive clones. Selected eligible hybridoma cells were subjected to subcloning by limiting dilution assay in 96-wells plate and cultured in DMEM medium (purchased from Invitrogen) containing 10% (w/w) HT FBS at 37° C. in 5% (v/v) $CO_2$. 10 days after the subcloning, initial screening was performed using ELISA and Acumen, and single positive monoclones were selected and subjected to expansion culture in 24-wells plate. After 3 days, positive antigen binding was confirmed by FACS, while the criteria for the evaluation is that OD450 nm>1.0 for ELISA, and MFI>50 for FACS.

According to the detection results of 24-wells plate, the optimal clone was picked and expanded in DMEM medium (purchased from Invitrogen) containing 10% (w/w) HT FBS at 37° C. in 5% (v/v) $CO_2$. The optimal clone was obtained and stored in liquid nitrogen, and then used for subsequently production and purification of lead antibody.

(4) Production and Purification of Lead Antibody

The antibody concentration generated by hybridoma cells was relatively low, i.e. about only 1-10 mg/mL with a broad-range variation, and the various proteins produced by cell culturing and the contents of FBS contained in the culture medium have interfered many biologic activity assays to different degrees. Therefore, a small-scale (1-5 mg) production and purification of antibody is necessary.

The hybridoma cells obtained by section (3) were seeded into T-75 cell culture flask and passaged for three times.

Until reaching a robust growing state, cells were seeded into the spinner flasks for cell culturing. 200 mL of production culture medium were added to each 2 L spinner flask at a seeding density of $1.0 \times 10^5$/mL. The flask lid was tightened and the spinner flask was placed on the rotary machine in a 37° C. incubator with a 3 rpm of rotation speed. The cell culture was collected after continuous spinning culture for 14 days and cells were removed by filtration through a 0.45 µm filter until the culture supernatant was clear which is ready for immediate purification or stored at −30° C.

The TPBG antibody containing in the obtained culture supernatant (200 mL) was purified using 2 mL of protein A column (purchased from GE Healthcare). The protein G column was first equilibrated with equilibration buffer (PBS buffer, pH7.4), and then loaded by the culture supernatant at a controlled flow rate of 3 mL/min. Four bed volumes of equilibration buffer was used to wash the protein G column once sample loading was complete. The TPBG antibody bound to protein A column was eluted using elution buffer (0.1M sodium citrate buffer, pH3.5), and the elution was monitored by UV detector (A280 nm absorption). The antibody eluate was collected and pH was neutralized by adding with 10% (v/v) of 1.0M Tris-HCl buffer, then the eluate was immediately subjected to dialysis against PBS buffer overnight, and the buffer was changed once the next day and the dialysis was continued for 3 h. The dialyzed TPBG antibody was harvested, and filtered by 0.22 m sterile filter, thereby a purified TPBG antibody was obtained and stored in sterile condition.

The purified TPBG antibody was tested for its protein concentration ($A_{280\ nm}$/1.4), purity, endotoxin (Lonza kit) and the like. Results shown in Table 4 indicates that the concentration of endotoxin in the final antibody product is below 1.0 EU/mg.

TABLE 4

Analysis of purified TPBG antibody

| Clone Number | Antibody Purity | Protein Concentration (mg/mL) | Endotoxin (EU/mg) |
|---|---|---|---|
| 12B12C7C3 (12B12 for short) | >90% | 0.82 | <0.12 |
| 28D4E6A9 (28D4 for shot) | >90% | 1.02 | <0.12 |

(5) Identification of Lead Antibody

A. Detection of TPBG Antibody Binding to TPBG Protein by Enzyme-Linked Immunosorbent Assay (ELISA)

The purified TPBG antibody reacted with human TPBG-hFc.

The purified human TPBG-hFc obtained from step (1) diluting with PBS to a final concentration of 1.0 µg/mL was aliquoted into a 96-well ELISA plate at 100 µL per well, and sealed with a parafilm and incubated at 4° C. overnight. The plate was washed twice with plate washing buffer (PBS containing 0.01% (v/v) Tween 20), and blocked with blocking buffer (PBS containing 0.01% (v/v) Tween 20 and 1% (w/w) BSA) at room temperature for 2 h. The blocking buffer was discarded, and 100 t L per well of the purified antibody TPBG was added. After incubating at 37° C. for 2 h, the plate was washed for three times with plate washing buffer (PBS containing 0.01% (v/v) Tween 20). HRP (horseradish peroxidase)-labeled secondary antibody (purchased from Sigma) was added and incubated at 37° C. for 2 h, and the plate was washed for three times using plate washing buffer (PBS containing 0.01% (v/v) Tween 20). 100 µL of TMB substrate was aliquoted into each well, incubated at room temperature for 30 min, and 100 µL of stop buffer (1.0N HCl) per well was subsequently added. $A_{450\ nm}$ values were read using the ELISA plate reader (SpectraMax 384plus purchased from Molecular Device), and the results were shown in Table 5. Table 5 indicates that purified TPBG antibody can combine with recombinant TPBG protein at the level of ELISA. In Table 5 the IgG control herein is a mice IgG control, the data in the Table are $OD_{450\ nm}$ values, and Blank represents the $OD_{450\ nm}$ value of PBS buffer in the plate.

TABLE 5

ELISA detection of the binding reaction between the TPBG antibody and human TPBG-hFc protein

| $OD_{450\ nm}$ Clone Number | Antibody Concentration(nM) | | | | | | | |
|---|---|---|---|---|---|---|---|---|
| | 200 | 20 | 2 | 0.2 | 0.02 | 0.002 | 0.0002 | Blank |
| 12B12C7C3 | 2.82 | 2.83 | 2.84 | 1.67 | 0.29 | 0.13 | 0.10 | 0.11 |
| 28D4E6A9 | 2.60 | 2.59 | 2.64 | 1.97 | 0.46 | 0.14 | 0.10 | 0.09 |
| IgG control | 0.24 | 0.11 | 0.10 | 0.11 | 0.10 | 0.10 | 0.11 | 0.11 |

B. The Binding of TPBG Antibody to TPBG-Expressing Cells was Detected by Fluorescence Activated Cell Sorting (FACS)

The nucleotide sequence encoding the full-length amino acid sequence of human TPBG (wherein the accession numbers of amino acid sequence and nucleotide sequence encoding human TPBG protein in Genbank are Genbank ID AAH37161.1 and Gene ID: 7162, respectively) was cloned into the pIRES vector (purchased from Clontech) and a plasmid was prepared. pIRES plasmid containing the nucleotide sequence encoding human TPBG full-length amino acid sequence (PEI, purchased from Polysciences) was transfected into CHO-k1 cell line (purchased from ATCC), and a recombinant CHO-k1 cell line containing human TPBG (herein referred to as CHOk1-hTPBG stable cell line) was obtained. Similarly, the nucleotide sequence encoding the full-length amino acid sequence of cynomolgus TPBG (wherein the accession numbers of amino acid sequence and nucleotide sequence encoding cynomolgus TPBG protein in Genbank are Genbank ID BAE00432.1 and Gene ID: 102132149, respectively) was cloned into the pIRES vector (purchased from Clontech) and a plasmid was prepared. pIRES plasmid containing the nucleotide sequence encoding cynomolgus TPBG full-length amino acid sequence (PEI, purchased from Polysciences) was transfected into CHO-k1 cell line (purchased from ATCC), and a recombinant CHO-k1 cell line containing cynomolgus TPBG (herein referred to as CHOk1-cTPBG stable cell line) was obtained. Similarly, the nucleotide sequence encoding the full-length amino acid sequence of mouse TPBG (wherein the accession numbers of amino acid sequence and nucleotide sequence encoding mouse TPBG protein in Genbank are Genbank ID: CAA09931.1 and Gene ID: 21983, respectively) was cloned into the pIRES vector (purchased from Clontech) and a plasmid was prepared. pIRES plasmid containing the nucleotide sequence encoding mouse TPBG full-length amino acid sequence (PEI, purchased from Polysciences) was transfected into CHO-k1 cell line (purchased from ATCC), and a recombinant CHO-k1 cell line containing mouse TPBG (herein referred to as CHOk1-mTPBG stable cell line) was obtained.

The titers and specificity of the TPBG antibody in serum were measured by FACS. For the detection method, please refer to the method for identifying the stable cell line HEK293-hTPBG in the "Preparation of Immunogen B", step (2) as described above. Results were shown in Table 6. Results in Table 6 indicate that human, cynomolgus or mouse TPBG protein are overexpressed on the cell membrane of the stable cell lines CHOk1-hTPBG, CHOk1-cTPBG and CHOk1-mTPBG, respectively, which can be used for the screening of TPBG antibody.

TABLE 6

Results of FACS screening and detection of human/cynomolgus/mouse TPBG-transfected CHOK1 cells

| Transfected Cell | Cellular MFI | |
|---|---|---|
| Clone Number | Control IgG | Anti-TPBG antibody |
| CHOk1-hTPBG 3A2F1 | 3.24 | 798.37 |
| CHOk1-cTPBG 3F13G4 | 2.66 | 198.35 |
| CHOk1-mTPBG 3A3 | 2.38 | 135.25 |

The stable cell lines CHOk1-hTPBG, CHOk1-cTPBG, CHOk1-mTPBG (i.e. the CHOk1-hTPBG 3A2F1, CHOk1-cTPBG 3F13G4 and CHOk1-mTPBG 3A3 shown in Table 6) and CHO-k1 cells were expanded to a 90% of confluency in T-75 cell culture flasks, and the culture medium were removed. Cells were then rinsed twice with HBSS buffer (Hanks Balanced Salt Solution, purchased from Invitrogen) and lysed with enzyme-free cell dissociation buffer (Versene solution was purchased from Life technology) and harvested. Harvested cells were rinsed with HBSS buffer twice and counted before diluting with HBSS buffer to $2\times10^6$ cells/mL, and 10% goat serum blocking buffer was then added, wherein the percentage is the mass percentage. Cells were incubated on ice for 30 min, and then washed twice with HBSS buffer by centrifugation. The harvested cells were resuspended with FACS buffer (HBSS+1% BSA, wherein the percentage is mass percentage) to a concentration of $2\times10^6$ cells/mL. 100 μL per well of the cells was aliquoted to 96-well FACS reaction plates, and 100 μL per well of test sample—the purified TPBG antibody obtaining from step (4) as described above was added before incubating on ice for 2 h. The plate was washed with the FACS buffer twice by centrifugation, and 100 μL per well of fluorescence (Alexa 488) labeled secondary antibody (purchased from Invitrogen) was then added and incubated on ice for 1 h. The plate was washed with the FACS buffer for three times by centrifugation, follow by resuspending in 100 μL of fixation buffer (4% (v/v) paraformaldehyde). Cells were washed with FACS buffer twice after 10 min, follow by resuspending with 100 μL of FACS buffer. The results were measured and analyzed by FACS (FACS Calibur, purchased from BD). The data was analyzed by software (CellQuest) to obtain the mean fluorescence intensity (MFI) of the cells, follow by calculating EC50 value by software (GraphPad Prism) analysis and data fitting. The analysis results were shown in Table 7. Data in Table 7 is the EC50 values converted from the MFI, and Table 7 indicates that TPBG antibody is able to bind cell-surface TPBG proteins.

TABLE 7

FACS Analysis of Binding Activity of TPBG Antibody to Human/Cynomolgus/Mouse TPBG-expressing Cell Lines

| | EC50 (nM) | | | |
|---|---|---|---|---|
| Clone Number | CHOk1-hTPBG | CHOk1-cTPBG | CHOk1-mTPBG | CHO-k1 |
| 12B12C7C3 | 0.65 | 0.59 | Negative | Negative |
| 28D4E6A9 | 0.63 | 0.25 | Negative | Negative |

(6) Analysis of Epitope Distribution of TPBG Antibody and Antibody Via Competitive ELISA Assay The aforementioned TPBG antibodies were grouped by competitive ELISA in order to identify the binding sites of the antibodies to antigens.

The purified antibodies to be tested were diluted to 1 g/mL using PBS, and coated to high-adsorption of 96-wells microplate at 50 μL per well. After overnight coating at 4° C., 250 μL of blocking buffer (PBS containing 0.01% (v/v) Tween20 and 1% (w/w) BSA) was added to block coating at room temperature for 1 h, and 0.05 g/mL of biotinylated recombinant TPBG protein was added to each well. Meanwhile, 5 g/mL final concentration of competitive antibodies, i.e. the purified antibodies with the clone number of 12B12C7C3 and 28D4E6A9 were added and incubated at 25-37° C. for 1-2 h. The plates were washed three times with plate-washing buffer (PBS containing 0.01% (v/v) Tween20) and HRP (horseradish peroxidase)-labeled streptavidin (purchased from Sigma) was added. After incubating at 37° C. for 0.5 h, the plates were washed three times with plate-washing buffer (PBS containing 0.01% (v/v) Tween20), and 100 μL of TMB substrate was added to each well and the plates were further incubated at room temperature for 30 min prior to adding 100 μL of stop buffer (1.0N HCl) to each well. $A_{450\ nm}$ values were read using an ELISA microplate reader (SpectraMax 384plus purchased from Molecular Device). The competition rates between the antibodies were calculated according to the $A_{450\ nm}$ values, and results were shown in Table 8. The higher the values of the competition rate, the closer the antigen surface of the two antibodies are.

TABLE 8

Competition Rates Between antibody 12B12C7C3 and antibody 28D4E6A9

| | A | |
|---|---|---|
| B | 12B12C7C3 | 28D4E6A9 |
| 12B12C7C3 | 97% | 74% |
| 28D4E6A9 | 24% | 96% |

The results indicate that epitopes of 12B12C7C3 and 28D4E6A9 are different.

(7) Determination of Amino Acid Sequences of the Light Chain and Heavy Chain Variable Regions Total RNA Extraction: $5\times10^7$ hybridoma cells prepared in previous step (3) were collected by centrifugation, and 1 mL of Trizol was added, mixed and then the mixture was transferred to a 1.5 mL Eppendorf tube and allowed to stand at room temperature for 5 min. Next, 0.2 mL of chloroform was added, vortexed for 15 s and the tube was allowed to stand for 10 min and then centrifugated at 12,000 g, 4° C. for 5 min. The supernatant was transferred to a new 1.5 mL Eppendorf tube, and 0.5 mL of isopropanol was added, and the contents in the tube were mixed gently and allowed to stand for 10 min at room temperature prior to centrifuging at 12,000 g, 4° C. for 15 min. The supernatant was discarded, 1 mL of 75% (v/v) ethanol was added and pellets were rinsed gently and centrifugated at 12,000 g for 5 min. The supernatant was removed, the pellets were air-dried before dissolving with DEPC-treated water (dissolution was promoted in a water bath at 55° C. for 10 min), and finally the total RNA was extracted.

Reverse transcription and PCR: 1 µg of total RNA was took and the reverse transcriptase was added, a 20 µL system was set up and reacted at 42° C. for 60 minutes prior to terminating reaction at 85° C. for 10 minutes. A 50 µL PCR system was set containing 1 µL of cDNA, 25 pmol of each primer, 250 µmol of dNTPs, 1 µL of DNA polymerase and a compatible buffer system. PCR program consisted of pre-denaturing at 95° C. for 3 minutes, 35 cycles of denaturing at 95° C. for 30 seconds, annealing at 55° C. for 30 seconds and extending at 72° C. for 35 seconds, followed by another extension at 72° C. for 5 minutes and then PCR products were harvested. The kit used for reverse transcription was PrimeScript RT Master Mix purchased from Takara, with Cat. No. RR036; and the kit used for PCR including the Q5 high-fidelity enzyme was purchased from NEB, with Cat. No. M0492.

Cloning and sequencing: 5 µL of PCR products were determined by agarose gel electrophoresis, and positive samples were purified by column recovery kit NucleoSpin® Gel & PCR Clean-up, purchased from MACHEREY-NAGEL with a Cat. No. of 740609. Ligation was carried out at 16° C. for half an hour in 10 µL of final reaction system comprising 50 ng of sample, 50 ng of T vector, 0.5 µL of ligase and 1 µL of buffer and the ligated products were harvested, wherein the ligation kit is T4 DNA ligase purchased from NEB with a Cat. No. of M0402. Later on, 5 µL of the ligation product was pipetted into 100 µL of competent cells (Ecos 101 competent cells, purchased from Yeastern, Cat. No. FYE607) and ice-cooled for 5 minutes. Subsequently the competent cells were heat shocked at 42° C. for 1 minute in water bath and placed on ice for 1 minutes, then 650 µL of antibiotic-free SOC medium was added and the competent cells were recovered at 200 RPM on a shaker at 37° C. for 30 minutes, followed by pipetting and spreading 200 µL of cells suspension on LB solid medium containing antibiotic and culturing overnight in 37° C. incubator. On the next day, colony PCR was performed in a 30 µL PCR system using primers M13F and M13R specifically designed for T vector. Bacterial colonies were picked by a tip and pipetted into the PCR system and mixed, and 0.5 µL of suspension was plated onto another LB solid plate containing 100 µg/mL ampicillin to preserve the bacterial strain. 5 µL of product was subjected to the detection by agarose gel electrophoresis when the PCR reaction is completed, and the positive samples were sequenced and analyzed [see Kabat, "Sequences of Proteins of Immunological Interest," National Institutes of Health, Bethesda, Md. (1991)].

The amino acid sequence of heavy chain variable region is shown in SEQ ID NO: 2, and the light chain variable region sequence is shown in SEQ ID NO: 4 for the antibody 12B12C7C3.

wherein the amino acid sequence of CDR1 in the heavy chain variable region corresponds to positions 31 to 35 of SEQ ID NO: 2, the amino acid sequence of CDR2 in the heavy chain variable region corresponds to positions 50 to 66 of SEQ ID NO: 2, the amino acid sequence of CDR3 in the heavy chain variable region corresponds to positions 99 to 109 of SEQ ID NO: 2;

The amino acid sequence of CDR1 in the light chain variable region of the mouse antibody corresponds to positions 24 to 38 of SEQ ID NO: 4, the amino acid sequence of CDR2 corresponds to positions 54 to 60 of SEQ ID NO: 4, the amino acid sequence of CDR3 corresponds to positions 93 to 101 of SEQ ID NO: 4.

The amino acid sequence of heavy chain variable region of the antibody 28D4E6A9 is shown in SEQ ID NO: 6, the amino acid sequence of the light chain variable region is shown in SEQ ID NO: 8.

wherein the amino acid sequence of CDR1 in the heavy chain variable region corresponds to positions 31 to 35 of SEQ ID NO: 6, the amino acid sequence of CDR2 in the heavy chain variable region corresponds to positions 50 to 66 of SEQ ID NO: 6, the amino acid sequence of CDR3 in the heavy chain variable region corresponds to positions 99 to 109 of SEQ ID NO: 6;

The amino acid sequence of CDR1 in the light chain variable region of the mouse antibody corresponds to positions 24 to 34 of SEQ ID NO: 8, the amino acid sequence of CDR2 corresponds to positions 50 to 56 of SEQ ID NO: 8, the amino acid sequence of CDR3 corresponds to positions 89 to 97 of SEQ ID NO: 8.

Nucleotide sequencing results are as follows:

The nucleotide sequence of the heavy chain variable region is shown in SEQ ID NO: 1, and the nucleotide sequence of the light chain variable region is shown in SEQ ID NO: 3 for antibody 12B12C7C3;

the nucleotide sequence of heavy chain variable region of the is shown in SEQ ID NO: 5, and the nucleotide sequence of the light chain variable region is shown in SEQ ID NO: 7 for antibody 28D4E6A9;

wherein the nucleotide sequence encoding the CDR1 in the heavy chain variable region of 12B12C7C3 corresponds to positions from 91 to 105 of SEQ ID NO: 1;

the nucleotide sequence encoding the CDR2 in the heavy chain variable region of 12B12C7C3 corresponds to positions from 148 to 198 of SEQ ID NO: 1;

the nucleotide sequence encoding the CDR3 in the heavy chain variable region of 12B12C7C3 corresponds to positions from 295 to 327 of SEQ ID NO: 1;

the nucleotide sequence encoding the CDR1 in the light chain variable region of 12B12C7C3 corresponds to positions from 70 to 114 of SEQ ID NO: 3;

the nucleotide sequence encoding the CDR2 in the light chain variable region of 12B12C7C3 corresponds to positions from 160 to 180 of SEQ ID NO: 3;

the nucleotide sequence encoding the CDR3 in the light chain variable region of 12B12C7C3 corresponds to positions from 277 to 303 of SEQ ID NO: 3;

the nucleotide sequence encoding the CDR1 in the heavy chain variable region of 28D4E6A9 corresponds to positions from 91 to 105 of SEQ ID NO: 5;

the nucleotide sequence encoding the CDR2 in the heavy chain variable region of 28D4E6A9 corresponds to positions from 148 to 198 of SEQ ID NO: 5;

the nucleotide sequence encoding the CDR3 in the heavy chain variable region of 28D4E6A9 corresponds to positions from 295 to 327 of SEQ ID NO: 5;

the nucleotide sequence encoding the CDR1 in the light chain variable region of 28D4E6A9 corresponds to positions from 70 to 102 of SEQ ID NO: 7;

the nucleotide sequence encoding the CDR2 in the light chain variable region of 28D4E6A9 corresponds to positions from 148 to 168 of SEQ ID NO: 7;

the nucleotide sequence encoding the CDR3 in the light chain variable region of 28D4E6A9 corresponds to positions from 265 to 291 of SEQ ID NO: 7;

2. Preparation of Mouse-Human Chimeric Antibody 12B12 and 28D4

The amino acid sequences of the heavy chain variable region and the light chain variable region of the anti-TPBG mouse monoclonal antibody 12B12 were exemplified in SEQ ID NO: 2,4, respectively. The amino acid sequences of the heavy chain variable region and the light chain variable region of the anti-TPBG mouse monoclonal antibody 28D4 were exemplified in SEQ ID NO: 6,8, respectively.

(1) Plasmid Construction and Preparation: The sequences of the heavy chain variable regions in the mouse lead antibodies were incorporated into an expression vector containing a signal peptide and a constant region of human heavy chain antibody IgG1 (the expression vector was purchased from Invitrogen, and the recombination process was completed by ChemPartner, Shanghai), and the sequences of the light chain variable regions in the TPBG antibodies were incorporated into an expression plasmid containing a signal peptide and a constant region of human light chain kappa (the expression vector was purchased from Invitrogen, and the recombination process was completed by ChemPartner, Shanghai), and the recombined plasmids were confirmed by sequencing (The experimental principle and steps of the above plasmid recombination can be found in the 'Molecular Cloning: A Laboratory Manual' (Third Edition), (US) J. Sambrook et al). High-purity of recombinant plasmid was extracted by an alkaline lysis kit (purchased from MECHEREY-NAGEL), and more than 500 g of plasmid was harvested and filtered through a 0.2 m membrane filter (purchased from Millipore) for following transfection.

(2) Cell Transfection: 293E cells (purchased from Invitrogen) were cultured in Freestyle 293 expression medium (purchased from Invitrogen). The shaker was set at 37° C., 130 rpm and supplied with 8% $CO_2$ (v/v). During transfection, 10% (v/v) of F68 (purchased from Invitrogen) was added to Freestyle 293 expression medium to a final F68 concentration of 0.1% (v/v), and the Freestyle 293 culture medium containing 0.1% (v/v) F68, i.e. culture medium A was prepared. 5 mL of culture medium A was mixed with 200 μg/mL PEI (purchased from Sigma), thus obtaining culture medium B. 5 mL of culture medium A was mixed with 100 μg/mL of recombinant plasmid (here is a mixed recombinant plasmid in which the above-mentioned heavy chain recombinant plasmid and light chain recombinant plasmid were mixed in a conventional equal ratio) obtained in step (1) to prepare culture medium C. After 5 min, culture medium B and C were pooled and mixed, and allowed to stand for 15 min to prepare mixture D. 10 mL of mixture D was slowly added into 100 mL of Freestyle 293 expression medium containing 293E cells, with simultaneously oscillation to avoid over-aggregation of PEI, until the density of the 293E cells reach $1.5 \times 10^6$/mL and the cells were cultured in the shaker. Peptone was added the next day until its concentration reached 0.5% (w/v). From day5 to day7, the titer of antibodies in the culture were tested. From day6 to day7, the supernatant was collected by centrifugation (3500 rpm, 30 min) and filtered through a 0.22 m of membrane filter to prepare a filtered cell supernatant for further purification.

(3) Antibody Purification: Endotoxin-free chromatography columns and Protein A filler in continuous production state were treated with 0.1M NaOH for 30 min or washed with 5 column bed volumes of 0.5M NaOH. Fillers and chromatography columns without being used for a long time were soaked in 1M NaOH for at least 1 h, follow by neutralizing with endotoxin-free water and rinsing with 10 column bed volumes of 1% Triton X100. The column was equilibrated with 5 column bed volumes of PBS, and the filtered cells supernatant were loaded on the column and the flow-through portion of the sample was collected if necessary. After finishing sample loading, the column was washed by 5 column bed volumes of PBS. Eluent was eluted by 5 column bed volumes of 0.1M pH3.0 Glycine-HCl and collected, and the column was then neutralized with 1/10 volume of 1M Tris-HCl, pH8.5. The antibody was harvested and then dialyzed in 1×PBS overnight to prevent endotoxin contamination. Then, the concentration of the antibody was determined by spectrophotometer or kit, the purity of the antibody was determined by HPLC-SEC, and the content of endotoxin was determined by endotoxin detection kit (purchased from Lonza).

Purified TPBG chimeric antibodies 12B12 and 28D4 were harvested respectively

3. Preparation of Humanized TPBG Antibody

Human germline templates of antibody heavy chain variable region and light chain variable region that match the non-CDR regions of chimeric antibody 12B12 or 28D4 described above optimally were selected in the Germline database. The human 'acceptor' sequence of the humanized TPBG antibody is selected from the human germline exon $V_H$, $J_H$, $V_k$ and $J_k$ sequences. The template for the heavy chain variable region of the 12B12 antibody comprises VH3-48 and VH3-30 of the $V_H$ exon of the human germline antibody heavy chain $V_H$ exon, and JH-6 of the $J_H$ exon, and the template of the light chain variable region comprises B3 and A2 of the human germline antibody light chain $V_K$ exon, and /$J_K$-2 of the $J_K$ exon. The template for the heavy chain variable region of the 28D4 antibody comprises VH3-11 of the human germline antibody heavy chain $V_H$ exon, and $J_H$-6 of the $J_H$ exon, and the template of the light chain variable region comprises O18 and A2 of human germline antibody light chain $V_K$ Exons, and JK exon of $J_K$-5.

The heavy and light chain CDRs of chimeric antibody 12B12 or 28D4, amino acid residues of which determined according to the Kabat definition, were each grafted into a selected human germline template, and the CDR regions of the human germline template were replaced to obtain a humanized antibody. Based on the three-dimensional structure of the mouse antibody, reverse mutation on the embedding residues, residues that directly interact with CDRs region and ones that have an important impact on conformation of VL and VH were conducted, and the humanized antibody was obtained. Briefly, synthetic overlapping oligonucleotides spanning human VH or VL domain were generated and each domain was assembled using PCR overlap extension. The VH domain was directionally cloned into an expression vector containing signal peptide and constant region of humanized antibody heavy chain IgG1, and the $V_L$ domain was directionally cloned into an expression vector containing signal peptide and human antibody light chain kappa using restriction site for incorporation of PCR product. The obtained recombinant plasmids were confirmed by sequencing, and high-purity of recombinant plasmids were extracted by an alkaline lysis kit (purchased from MACHEREY-NAGEL). More than 500 g of plasmid was collected and subjected to a 0.22 μm membrane filter (purchased from Millipore) for following transfection.

Figure 1:
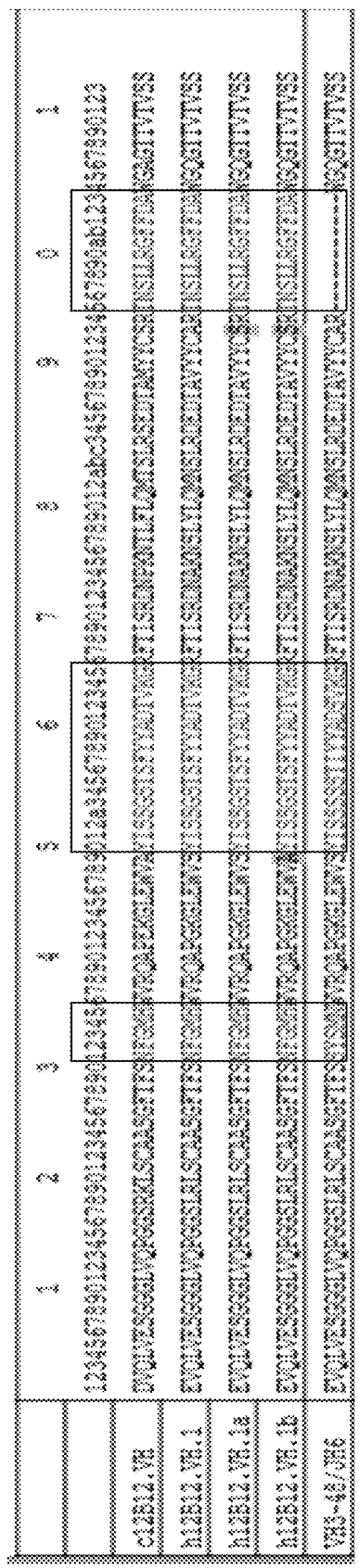
FIG. 1. Sequence comparison of humanized anti-TPBG antibody 12B12 heavy chain variable region h12B12.VH1 and its variants with 12B12 chimeric antibody VH and human germline VH exon hVH3-48/JH-6. CDRs are boxed off.

Sequence alignment of the heavy and light chain variable regions among humanized anti-TPBG antibody variants, the human germline and chimeric antibodies are shown in FIG. 1-6. FIG. 1 shows the sequence comparison of humanized anti-TPBG antibody 12B12 heavy chain variable region h12B12.VH1 and its variants, 12B12 chimeric antibody VH and human germline VH exon hVH3-48/JH-6. FIG. 2 is a sequence comparison of humanized anti-TPBG antibody 12B12 heavy chain variable region h12B12.VH2 and its variants, 12B12 chimeric antibody VH and human germline VH exon hVH3-30/JH-6. FIG. 3 is a sequence comparison of humanized anti-TPBG antibody 12B12 light chain variable region h12B12.Vk1 and its variant, 12B12 chimeric antibody Vk and human germline Vk exon B3/Jk-2. FIG. 4 is a sequence comparison of humanized anti-TPBG antibody 12B12 light chain variable region h12B12.Vk2 and its variants, 12B12 chimeric antibody Vk and human germline Vk exon A2/Jk-2. FIG. 5 is a sequence comparison of humanized anti-TPBG antibody 28D4 heavy chain variable region h28D4 VH1 and its variants, 28D4 chimeric antibody VH and the human germline VH exon hVH3-11/JH-6. FIG. 6 is a sequence comparison of humanized anti-TPBG antibody 28D4 light chain variable region h28D4.Vk1 and its variants, 28D4 chimeric antibody Vk and human germline Vk exon O18/Jk-5.

Human germline heavy chain variable region template VH3-48/JH6 (SEQ ID NO: 9) is as follows

VH3-48:
EVQLVESGGGLVQPGGSLRLSCAASGFTFSSYSMNWVRQAPGKGLEWVSY

ISSSSSTIYYADSVKGRFTISRDNAKNSLYLQMNSLRDEDTAVYYCAR;

JH6:
WGQGTTVTVSS.

Human germline heavy chain variable region template VH3-30/JH6 (SEQ ID NO: 10) is as follows

VH3-30:
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAR;

JH6:
WGQGTTVTVSS.

Human germline light chain variable region template B3/Jk2 (SEQ ID NO: 11) is as follows

B3:
DIVMTQSPDSLAVSLGERATINCKSSQSVLYSSNNKNYLAWYQQKPGQPP

KLLIYWASTRESGVPDRFSGSGSGTDFTLTISSLQAEDVAVYYC;

JK2:
FGQGTKLEIK.

Human germline light chain variable region template A2/Jk2 (SEQ ID NO: 12) is as follows

A2:
DIVMTQTPLSLSVTPGQPASISCKSSQSLLHSDGKTYLYWYLQKPGQPPQ

LLIYEVSNRFSGVPDRFSGSGSGTDFTLKISRVEAEDVGVYYC;

JK2:
FGQGTKLEIK.

Human germline heavy chain variable region template VH3-11/JH6 (SEQ ID NO: 13) is as follows

VH3-11:
QVQLVESGGGLVKPGGSLRLSCAASGFTFSDYYMSWIRQAPGKGLEWVSY

ISSSGSTIYYADSVKGRFTISRDNAKNSLYLQMNSLRAEDTAVYYCAR;

JH6:
WGQGTTVTVSS.

Human germline light chain variable region template O18/Jk5 (SEQ ID NO: 14) is as follows

O18:
DIQMTQSPSSLSASVGDRVTITCQASQDISNYLNWYQQKPGKAPKLLIYD

ASNLETGVPSRFSGSGSGTDFTFTISSLQPEDIATYYC;

JK5:
FGQGTRLEIK.

Several framework positions were selected to reintroduce mouse donor residues. Humanized 12B12 and 28D4 variants can be produced by incorporating different combinations of mouse framework donor residues in VH domain or human CDR residues in VL domain. These variants are summarized in Tables 9 and 10 below. These two tables show the variable regions of these variants, without including the constant regions. In Tables 9 and 10, a c initial means chimeric antibody and a h initial means humanized antibody; wherein, in the columns of donor framework residues and reverse mutation, for example, 'A93S' in each humanized anti-TPBG antibody 12B12 heavy chain variable region h12B12.VH1 and its variants indicates that the 93rd amino acid shown in FIG. 1 is mutated from "A" alanine to "S" serine, and the site of the reverse mutation is located in the framework region. Terms of other mutations are the same as the above examples unless otherwise specified.

TABLE 9

| Antibody | Heavy chain | Heavy chain variable region template VH of the germ line of human antibody | Donor framework residues and reverse mutation | SEQ ID NO: | Light chain | Light chain variable region template Vk of the germ line of human antibody | Donor framework residues and reverse mutation | SEQ ID NO: |
|---|---|---|---|---|---|---|---|---|
| c12B12 | VH | None | CDR | 2 | Vk | None | CDR | 4 |
| h12B12-1 | VH.1a | VH-48/JH6 | CDR-grafted, A93S | 18 | Vk.1 | B3/Jk2 | CDR-grafted | 26 |
| h12B12-2 | VH.1b | VH-48/JH6 | CDR-grafted, S49A, A93S | 20 | Vk.1 | B3/Jk2 | CDR-grafted | 26 |

TABLE 9-continued

| Antibody | Heavy chain | Heavy chain variable region template VH of the germ line of human antibody | Donor framework residues and reverse mutation | SEQ ID NO: | Light chain | Light chain variable region template Vk of the germ line of human antibody | Donor framework residues and reverse mutation | SEQ ID NO: |
|---|---|---|---|---|---|---|---|---|
| h12B12-3 | VH.2a | VH3-30/JH6 | CDR-grafted, Q1E, A93S | 24 | Vk.1 | B3/Jk2 | CDR-grafted | 26 |
| h12B12-4 | VH.1 | VH3-48/JH6 | CDR-grafted | 16 | Vk.1a | B3/Jk2 | CDR-grafted, M4L, Y49K | 28 |
| h12B12-5 | VH.1a | VH3-48/JH6 | CDR-grafted, A93S | 18 | Vk.1a | B3/Jk2 | CDR-grafted, M4L, Y49K | 28 |
| h12B12-6 | VH.1b | VH3-48/JH6 | CDR-grafted, S49A, A93S | 20 | Vk.1a | B3/Jk2 | CDR-grafted, M4L, Y49K | 28 |
| h12B12-7 | VH.2 | VH3-30/JH6 | CDR-grafted, Q1E | 22 | Vk.1a | B3/Jk2 | CDR-grafted, M4L, Y49K | 28 |
| h12B12-8 | VH.2a | VH3-30/JH6 | CDR-grafted, Q1E, A93S | 24 | Vk.1a | B3/Jk2 | CDR-grafted, M4L, Y49K | 28 |
| h12B12-9 | VH.1a | VH3-48/JH6 | CDR-grafted, A93S | 18 | Vk.2 | A2/Jk2 | CDR-grafted | 30 |
| h12B12-10 | VH.1b | VH3-48/JH6 | CDR-grafted, S49A, A93S | 20 | Vk.2 | A2/Jk2 | CDR-grafted | 30 |
| h12B12-11 | VH.2a | VH3-30/JH6 | CDR-grafted, Q1E, A93S | 24 | Vk.2 | A2/Jk2 | CDR-grafted | 30 |
| h12B12-12 | VH.1 | VH3-48/JH6 | CDR-grafted | 16 | Vk.2a | A2/Jk2 | CDR-grafted, M4L, Y49K | 32 |
| h12B12-13 | VH.1a | VH3-48/JH6 | CDR-grafted, A93S | 18 | Vk.2a | A2/Jk2 | CDR-grafted, M4L, Y49K | 32 |
| h12B12-14 | VH.1b | VH3-48/JH6 | CDR-grafted, S49A, A93S | 20 | Vk.2a | A2/Jk2 | CDR-grafted, M4L, Y49K | 32 |
| h12B12-15 | VH.2 | VH3-30/JH6 | CDR-grafted, Q1E | 22 | Vk.2a | A2/Jk2 | CDR-grafted, M4L, Y49K | 32 |
| h12B12-16 | VH.2a | VH3-30/JH6 | CDR-grafted, Q1E, A93S | 24 | Vk.2a | A2/Jk2 | CDR-grafted, M4L, Y49K | 32 |

表10

| Antibody | Heavy chain | Heavy chain variable region template VH of the germ line of human antibody | Donor framework residues and reverse mutation | SEQ ID NO: | Light chain | Light chain variable region template Vk of the germ line of human antibody | Donor framework residues and reverse mutation | SEQ ID NO: |
|---|---|---|---|---|---|---|---|---|
| c28D4 | VH | None | CDR | 6 | Vk | None | CDR | 8 |
| h28D4-1 | VH.1 | VH3-11/JH6 | CDR-grafted | 34 | Vk.1 | O18/Jk5 | CDR-grafted | 42 |
| h28D4-2 | VH.1a | VH3-11/JH6 | CDR-grafted, Q1E, A93I, R94M | 36 | Vk.1 | O18/Jk5 | CDR-grafted | 42 |
| h28D4-3 | VH.1b | VH3-11/JH6 | CDR-grafted, Q1E, A93I, R94M, S49A, N76K | 38 | Vk.1 | O18/Jk5 | CDR-grafted | 42 |
| h28D4-4 | VH.1c | VH3-11/JH6 | CDR-grafted, Q1E, A93I, R94M, S49A, N76K, I37A, G44R | 40 | Vk.1 | O18/Jk5 | CDR-grafted | 42 |
| h28D4-5 | VH.1 | VH3-11/JH6 | CDR-grafted | 34 | Vk.1a | O18/Jk5 | CDR-grafted, F71Y | 44 |
| h28D4-6 | VH.1a | VH3-11/JH6 | CDR-grafted, Q1E, A93I, R94M | 36 | Vk.1a | O18/Jk5 | CDR-grafted, F71Y | 44 |
| h28D4-7 | VH.1b | VH3-11/JH6 | CDR-grafted, Q1E, A93I, R94M, S49A, N76K | 38 | Vk.1a | O18/Jk5 | CDR-grafted, F71Y | 44 |

-continued

表10

| Antibody | Heavy chain | Heavy chain variable region template VH of the germ line of human antibody | Donor framework residues and reverse mutation | SEQ ID NO: | Light chain | Light chain variable region template Vk of the germ line of human antibody | Donor framework residues and reverse mutation | SEQ ID NO: |
|---|---|---|---|---|---|---|---|---|
| h28D4-8 | VH.1c | VH3-11/JH6 | CDR-grafted, Q1E, A93I, R94M, S49A, N76K, I37A, G44R | 40 | Vk.1a | O18/Jk5 | CDR-grafted, F71Y | 44 |
| h28D4-9 | VH.1 | VH3-11/JH6 | CDR-grafted | 34 | Vk.1b | O18/Jk5 | CDR-grafted, F71Y, A43T, P44V, Y87F | 46 |
| h28D4-10 | VH.1a | VH3-11/JH6 | CDR-grafted, Q1E, A93I, R94M | 36 | Vk.1b | O18/Jk5 | CDR-grafted, F71Y, A43T, P44V, Y87F | 46 |
| h28D4-11 | VH.1b | VH3-11/JH6 | CDR-grafted, Q1E, A93I, R94M, S49A, N76K | 38 | Vk.1b | O18/Jk5 | CDR-grafted, F71Y, A43T, P44V, Y87F | 46 |
| h28D4-12 | VH.1c | VH3-11/JH6 | CDR-grafted, Q1E, A93I, R94M, 49A, N76K, I37A, G44R | 40 | Vk.1b | O18/Jk5 | CDR-grafted, F71Y, A43T, P44V, Y87F | 46 |

Note: The "/" in the table means "and" and the contents to the left and right of '/' are in parallel.

cDNAs were synthesized based on the amino acid sequences of the light chain variable region and heavy chain variable region of each humanized antibody (i.e., the sequences shown in SEQ ID NO: 15, 17, 19, 21, 23, 25, 27, 29, 31, 33, 35, 37, 39, 41, 43 and 45 of the sequence listing, respectively). Heavy chain cDNAs were digested by FspAI and AfeI, and light chain cDNAs were treated by FspAI and BsiwI. Those cDNA fragments were inserted into expression vector containing a signal peptide and a constant region of human heavy chain antibody IgG1 and expression plasmid containing a signal peptide and a constant region of human light chain kappa (the expression vector was purchased from Invitrogen, and the recombination process was completed by ChemPartner, Shanghai) by FspAI/AfeI or FspAI/BsiwI restriction sites, respectively. The recombined plasmids were confirmed by sequencing. High-purity of recombinant plasmid was extracted by an alkaline lysis kit (purchased from MECHEREY-NAGEL), and more than 500 g of plasmid was collected and subjected to a 0.22 μm membrane filter (purchased from Millipore) for following transfection.

Before transfection, 293E cells (purchased from Invitrogen) were cultured in Freestyle 293 expression medium (purchased from Invitrogen). During transfection, 10% (v/v) of F68 (purchased from Invitrogen) was added to Freestyle 293 expression medium to a final F68 concentration of 0.1% (v/v), and the Freestyle 293 culture medium containing 0.1% (v/v) F68, i.e. culture medium A was prepared. 5 mL of culture medium A was mixed with 200 g/mL PEI (purchased from Sigma), obtaining culture medium B. 5 mL of culture medium A was mixed with 100 μg of heavy and light chain recombinant plasmids (mass ratio of heavy chain recombinant plasmid to light chain recombinant plasmid is 1:1 to 1:3) to prepare culture medium C. After 5 min, culture medium B and C were pooled and mixed, and allowed to stand for 15 min to prepare mixture D. 10 mL of mixture D was slowly added into 100 mL of Freestyle 293 expression medium containing 293E cells, with simultaneously oscillation to avoid over-aggregation of PEI, until the density of the 293E cells reach $1.5 \times 10^6$/mL. The cells were then cultured in the shaker, and the shaker was set at 37° C., 130 rpm and 8% $CO_2$ (v/v). Peptone was added the next day until its concentration reached 0.5% (w/v). From day5 to day7, the titer of antibodies in the culture were tested. From day6 to day7, the supernatant was collected by centrifugation (3500 rpm, 30 min) and filtered through a 0.22 m of membrane filter to prepare a filtered cell supernatant for purification.

In antibody purification, continuous endotoxin-free chromatography columns and protein A filler (purchased from GE) were washed with 5 column bed volumes of 0.5M NaOH. The column was equilibrated with 5 column bed volumes of PBS (PBS buffer, pH 7.4), and the filtered cells supernatant were loaded on the column and the flow-through portion of the sample was collected if necessary. After finishing sample loading, 5 column bed volumes of PBS was used to wash the column. 5 column bed volumes of 0.1M pH3.0 Glycine-HCl was used to elute, immediately follow by collecting eluate and neutralizing TPBG antibody with 1/10 volume of 1M Tris-HCl, pH8.5. All of the solutions used above need to be freshly prepared. The antibody was harvested and then dialyzed in 1×PBS for 4 hours, meanwhile endotoxin contamination shall be prevented. Then, the concentration was determined by spectrophotometer or kit, the purity of the antibody was determined by HPLC-SEC, and the content of endotoxin was determined by endotoxin detection kit (purchased from Lonza). Obtained TPBG antibody was characterized (the procedure is as described in Embodiment 2, Embodiment 3, and Embodiment 4 below).

Embodiment 2 Detection of Binding of Humanized TPBG Antibody to TPBG Protein by Enzyme-Linked Immunosorbent Assay (ELISA)

The purified humanized TPBG antibody obtained from Embodiment 1 was reacted with human TPBG-hFc, for the method, see (5) Identification of lead antibody in Embodiment 1. The results are shown in FIGS. 7-8 and Tables 11-12. The EC50 in Table 11 and Table 12 are calculated according to the OD450 nm value of the h12B12 variants and the h28D4 variants, respectively. The results indicate that the purified humanized TPBG antibody variant binds well to the TPBG recombinant protein at the ELISA level. FIGS. 7A and 7B are the binding reactions of purified humanized h12B12 variants to human TBPG-hFc protein, and FIGS. 8A and 8B are the binding reactions of the purified humanized h28D4 variants to human TBPG-hFc protein.

TABLE 11

ELISA detection of the binding reaction between humanized h12B12 antibody variants and human TPBG-hFc protein

| Antibody | EC50 (nM) |
| --- | --- |
| Chimeric antibody 12B12 (control) | 0.137 |
| Humanized antibody 12B12-1 | 0.248 |
| Humanized antibody 12B12-2 | 0.274 |
| Humanized antibody 12B12-3 | 0.333 |
| Humanized antibody 12B12-4 | 0.227 |
| Humanized antibody 12B12-5 | 0.253 |
| Humanized antibody 12B12-6 | 0.362 |
| Humanized antibody 12B12-7 | 0.367 |
| Humanized antibody 12B12-8 | 0.287 |
| Humanized antibody 12B12-9 | 0.223 |
| Humanized antibody 12B12-10 | 0.25 |
| Humanized antibody 12B12-11 | 0.239 |
| Humanized antibody 12B12-12 | 0.206 |
| Humanized antibody 12B12-13 | 0.289 |
| Humanized antibody 12B12-14 | 0.257 |
| Humanized antibody 12B12-15 | 0.193 |
| Humanized antibody 12B12-16 | 0.2 |

TABLE 12

ELISA detection of the binding reaction between humanized h28D4 antibody and human TPBG-hFc protein

| Antibody | EC50 (nM) |
| --- | --- |
| Chimeric antibody 28D4 (control) | 0.165 |
| Humanized antibody 28D4-1 | 0.364 |
| Humanized antibody 28D4-2 | 0.181 |
| Humanized antibody 28D4-3 | 0.16 |
| Humanized antibody 28D4-4 | 0.147 |
| Humanized antibody 28D4-5 | 0.782 |
| Humanized antibody 28D4-6 | 0.205 |
| Humanized antibody 28D4-7 | 0.161 |
| Humanized antibody 28D4-8 | 0.162 |
| Humanized antibody 28D4-9 | 0.218 |
| Humanized antibody 28D4-10 | 0.224 |
| Humanized antibody 28D4-11 | 0.191 |
| Humanized antibody 28D4-12 | 0.167 |

Embodiment 3 Characterization and Analysis of Humanized TPBG Antibodies (Biacore)

To assess the binding specificity and affinity of the humanized anti-TPBG antibody, Biacore analysis was performed using human TPBG antigen immobilized on a CM5 chip. Biacore technique utilizes the change in the refractive index of surface layer after antibody binding to the TPBG antigen immobilized on the surface layer. The binding was determined by surface plasmon resonance (SPR) through detecting the laser refracted from the surface. Non-specific and specific interactions were distinguished by analysis of signal kinetics binding rate and dissociation rate. Chimeric antibodies 12B12 and 28D4 were used as controls.

TABLE 13

Results of Biacore Test

| Antibody | ka (1/Ms) | kd (1/s) | KD (M) |
| --- | --- | --- | --- |
| Chimeric Antibody 12B12 | 1.61E+06 | 1.64E−05 | 1.02E−11 |
| Humanized Antibody 12B12-4 | 1.58E+06 | 3.46E−05 | 2.20E−11 |
| Humanized Antibody 12B12-5 | 1.17E+06 | 2.10E−05 | 1.79E−11 |
| Humanized Antibody 12B12-12 | 1.23E+06 | 2.29E−05 | 1.86E−11 |
| Humanized Antibody 12B12-15 | 1.77E+06 | <1e−5 | <5.66E−12 |
| Humanized Antibody 12B12-16 | 1.59E+06 | 3.65E−05 | 2.29E−11 |
| Chimeric Antibody 28D4 | 2.50E+06 | 3.24E−05 | 1.30E−11 |
| Humanized Antibody 28D4-3 | 1.12E+06 | 4.57E−05 | 4.06E−11 |
| Humanized Antibody 28D4-4 | 1.55E+06 | 3.58E−05 | 2.31E−11 |
| Humanized Antibody 28D4-7 | 3.68E+06 | 9.42E−05 | 2.56E−11 |
| Humanized Antibody 28D4-8 | 1.02E+06 | 3.01E−05 | 2.96E−11 |
| Humanized Antibody 28D4-12 | 1.03E+06 | 3.94E−05 | 3.81E−11 |

Biacore results show that KD values of humanized anti-TPBG antibodies 12B12 and 28D4 variants are very similar to that of chimeric antibodies 12B12 and 28D4, demonstrating that humanized anti-TPBG antibodies did not significantly reduce antigen binding activity compared to chimeric antibodies.

Embodiment 4 the Binding of TPBG Antibody to TPBG-Expressing Cells was Detected by Fluorescence Activated Cell Sorting (FACS)

For the preparation method, FACS detection method and interpretation of the results of CHO-k1 stable cell line of human TPBG (CHOk1-hTPBG stable cell line), CHO-k1 stable cell line of cynomolgus TPBG (CHOk1-cTPBG stable cell line), and CHO-k1 stable cell line of mouse TPBG (CHOk1-mTPBG stable cell line), see (5) "Identification of lead antibody" in Embodiment 1.

The analysis results are shown in Tables 14, 15 and FIGS. 9, 10, and the data of FIGS. 9A-D and 10A-D are the mean fluorescence intensity (MFI) of the cells. The data in Tables 14 and 15 are EC50 values converted from MFI. Tables 14 and 15 show that humanized TPBG antibody variants specifically bind to cells expressing human TPBG protein on the surface and cells expressing cynomolgus TPBG protein on the surface, and don't bind to cells expressing mouse TPBG protein and TBPG expression negative CHO-k1.

TABLE 14

FACS analyzing the binding activity of humanized antibody 12B12 variants and TPBG expressing cell line

| Clone Number | EC50 (nM) | | | |
|---|---|---|---|---|
| | CHOK1-hTPBG | CHOK1-cTPBG | CHOK1-mTPBG | CHOK1 |
| Chimeric Antibody 12B12 | 0.33 | 0.67 | Negative | Negative |
| Humanized Antibody 12B12-12 | 0.33 | 10.31 | Negative | Negative |
| Humanized Antibody 12B12-15 | 0.37 | 0.87 | Negative | Negative |

TABLE 15

FACS analyzing the binding activity of humanized antibody 28D4 variants and TPBG expressing cell line

| Clone Number | EC50 (nM) | | | |
|---|---|---|---|---|
| | CHOK1-hTPBG | CHOK1-cTPBG | CHOK1-mTPBG | CHO-k1 |
| Chimeric Antibody 28D4 | 0.33 | 0.94 | Negative | Negative |
| Humanized Antibody 28D4-3 | 0.26 | 0.62 | Negative | Negative |
| Humanized Antibody 28D4-4 | 0.38 | 0.72 | Negative | Negative |
| Humanized Antibody 28D4-7 | 0.37 | 0.27 | Negative | Negative |

Embodiment 5 In Vitro Pharmacodynamic Studies of Humanized TPBG Antibody-Drug Conjugate The purified humanized TPBG antibodies obtained from Embodiment 1 were conjugated with MC-MMAF. After dialysis with sodium borate buffer (pH 6.5-8.5), Tris (2-carboxyethyl) phosphine (TCEP) was added, wherein the molar ratio of TCEP to the purified TPBG antibodies was 3. Reaction solution A was obtained by reductive reaction at room temperature for 1 h. The reaction solution A was desalted on G25 (purchased from GE) to remove excess TCEP and hence reaction buffer B was obtained. MC-MMAF was added to reaction buffer B, wherein the molar ratio of MC-MMAF to the purified humanized TPBG antibody was 10, and the reaction was carried out at room temperature for 4 h. Cysteine was added to neutralize excess MC-MMAF, and excess small molecules were removed by G25 desalting, thereby obtaining purified humanized TPBG antibody-drug conjugate (for the method of conjugation, refers to Doronina, 2006, Bioconjugate Chem. 17, 114-124). Drug-antibody ratio and purity of the drugs were analyzed by HPLC-HIC and HPLC-SEC, and the cytotoxicity was analyzed subsequently. The drug-antibody ratio (DAR) of all humanized TPBG antibody-drug conjugates was 3.0-5.0, wherein DAR (drug-antibody ratio) refers to the average number of small-molecule drugs carried on a single antibody molecule after antibody-drug conjugation.

Humanized TPBG antibody-drug conjugates were serially diluted with complete medium, respectively. 100 μL of cell suspension of TPBG-positive non-small cell lung carcinoma cell line NCI-H1568 (Purchased from ATCC, item #CRL-5876) was added to a 96-well plate at 2000 cells per well. After incubating the cell suspension overnight, 10 μL of purified TPBG chimeric antibody-drug conjugate diluents at different concentrations were added to each well. After 5 days further culturing, the cell viability was measured using the CellTiter-Glo kit (purchased from Promega and used according to instructions).

Results were shown in Tables 16, 17 and FIG. 11, wherein IC50 in Table 16 refers to the concentration of drug that is required for half inhibition of cellular activity, which can reflect the cytotoxicity by measuring cell viability. FIG. 11A shows the cytotoxicity of humanized TPBG antibody 12B12 variants antibody-drug conjugate on the TPBG-positive tumor cell line NCI-H1568, and FIG. 11B shows the cytotoxicity of humanized TPBG antibody 28D4 variants antibody-drug conjugate on the TPBG-positive tumor cell line NCI-H1568. The antibody drug conjugates of the humanized TPBG antibody variants have a killing effect on TPBG positive NCI-H1568 cells, however, the humanized antibody variants without coupling have no killing effect on TPBG-positive NCI-H1568 cells.

TABLE 16

Detection of Cytotoxicity of Humanized 12B12 Variants and its Antibody-drug Conjugates on TPBG-Positive Cells via Cellular Killing Assay

| Clone Number | IC50(nM) |
|---|---|
| Negative antibody control | Negative |
| Chimeric Antibody 12B12 | Negative |
| Humanized Antibody 12B12-12 | Negative |
| Humanized Antibody 12B12-15 | Negative |
| Negative antibody control -MMAF | Negative |
| Chimeric Antibody 12B12-MMAF | 0.063 |
| Humanized Antibody 12B12-12-MMAF | 0.066 |
| Humanized Antibody 12B12-15-MMAF | 0.058 |

TABLE 17

Detection of Cytotoxicity of Humanized 28D4 Variants and its Antibody-drug Conjugates on TPBG-Positive Cells via Cellular Killing Assay

| Clone Number | IC50(nM) |
|---|---|
| Chimeric Antibody 28D4 | Negative |
| Humanized Antibody 28D4-3 | Negative |
| Humanized Antibody 28D4-4 | Negative |
| Humanized Antibody 28D4-7 | Negative |
| Chimeric Antibody 28D4-MMAF | 0.091 |
| Humanized Antibody 28D4-3-MMAF | 0.061 |
| Humanized Antibody 28D4-4-MMAF | 0.074 |
| Humanized Antibody 28D4-7-MMAF | 0.066 |

Embodiment 6 Antibody-Drug Conjugates Coupled with Different Linker-Toxins

Purified humanized antibodies 12B12 and 28D4 obtained from Embodiment 1 were coupled with MC-MMAF and MC-VC-PAB-MMAE, respectively. After dialysis with sodium borate buffer with pH 6.5-8.5, tris(2-carboxyethyl) phosphine (TCEP) was added, wherein the molar ratio of TCEP to the purified TPBG antibodies was 3. Reductive reaction was carried out at room temperature for 1 h, and reaction solution A was obtained. Excess TCEP was removed by desalting reaction solution A with G25 (purchased from GE), and then reaction solution B was obtained. MC-MMAF or MC-VC-PAB-MMAE (purchased from Levena Biomart, Nanjing) was added to reaction solution B, wherein the molar ratio of MC-MMAF or MC-VC-PAB-MMAE to purified humanized TPBG antibody was 10. The reaction was carried out at room temperature for 4 h. Cysteine was further added to neutralize excess MC-MMAF or MC-VC-PAB-MMAE, and excess small molecules were removed by G25 desalting, thereby obtaining purified humanized TPBG antibody-drug conjugate (as for the method of conjugation please refer to Doronina, 2006, Bioconjugate Chem. 17, 114-124). Drug-antibody ratio and the purity of the drugs were analyzed by HPLC-HIC and HPLC-SEC, follow by determining the cytotoxicity of conjugates in vitro and pharmacodynamic studies in vivo. The drug-antibody ratios (DAR) of all humanized antibody-drug conjugates were about 3.0-5.0, wherein DAR (drug antibody ratio) refers to the average number of small-molecule drugs carried by a single antibody molecule after antibody-drug conjugation.

The purified humanized antibodies 12B12-12 and 28D4-3 obtained from Embodiment 1 were coupled with succinimidyl 4-(N-maleimidomethyl) cyclohexane-1-carboxylate (SMCC), respectively. After dialyzing the purified antibodies with phosphate buffer (pH 6.5-7.4), SMCC was added in the presence of 30% (v/v) dimethylacetamide (DMA), wherein the molar ratio of SMCC to the purified TPBG chimeric antibodies was 8. Reaction solution A was obtained after the reaction was carried out at room temperature for 1 h. Excess small molecules were removed by desalting reaction solution A with G25 column (purchased from GE) to obtain reaction solution B. N, N-dimethylacetamide (DMA) was added to reaction solution B until a final volume percent of 10% was reached, and DM1 (N2'-deacetyl-N2'-(3-mercapto-1-oxypropyl)-maytansine) was then added, wherein the molar ratio of DM1 to purified TPBG antibodies was 9. Reaction solution C was obtained once the reaction was carried out at room temperature for 3.5 h. Reaction solution C was subjected to desalting by G25 (purchased from GE) to remove excess small molecules, and the purified humanized TPBG chimeric antibody-drug conjugates (for the coupling method please refer to U.S. Pat. No. 5,208,020) were obtained. After the drug-antibody ratio was determined by LC-MS and the purity of the antibody-drug conjugates was analyzed by SEC, the cytotoxicity of conjugates in vitro and pharmacodynamic studies of conjugates in vivo were determined. The drug-antibody ratios (DAR) of all humanized antibody-drug conjugates were about 3.0-5.0, wherein DAR (drug antibody ratio) refers to the average number of small-molecule drugs carried by a single antibody molecule after antibody-drug conjugation.

Embodiment 7 In Vitro Pharmacodynamic Studies of Humanized TPBG Antibody-Drug Conjugate The purified humanized TPBG antibody-drug conjugates obtained in Embodiment 6 were serially diluted with complete medium, respectively. Each 100 µL of cell suspension of TPBG-positive non-small cell lung carcinoma cell line NCI-H1568 (purchased from ATCC, Catalog NO: #CRL-5876) containing 2000 cells was added to 96-wells cell culture plate and cultured overnight before adding with each 10 µL of purified TPBG antibody-drug conjugate at different concentrations. After further culturing the cells for 5 days, the cell viability was measured using the CellTiter-Glo kit (purchased from Promega and used according to instructions). Meanwhile, the non-small cell lung carcinoma cell line NCI-H1975 (purchased from ATCC, Catalog NO: #CRL-5908) and the breast cancer cell line MDA-MB-468 (purchased from ATCC, Catalog NO: #HTB-132) with weak expression of TPBG were selected to perform cytotoxicity test as described above.

Results were shown in Table 18 and FIG. 18, wherein the IC50 in Table 18 refers to the concentration of drug that is required for half inhibition of cellular activity, which reflects the cytotoxicity effects by measuring the cellular activity. FIG. 12A represents the cytotoxicity of humanized TPBG antibody-drug conjugate on TPBG-positive tumor cell line NCI-H1568. FIG. 12B represents the cytotoxicity of humanized TPBG antibody-drug conjugate on TPBG-weak positive tumor cell line NCI-H1975. FIG. 12C represents the cytotoxicity of humanized TPBG antibody-drug conjugate on TPBG positive tumor cell line MDA-MB-468. Results showed that humanized TPBG antibody-drug conjugates have cytotoxicity effect on TPBG-positive cells. Purified humanized TPBG antibody-drug conjugates coupled with different small molecule toxins have different levels of cytotoxicity effect on TPBG-positive cells, and TPBG chimeric antibody-drug conjugates coupled with MC-MMAF have lower IC50, indicating a cytotoxicity ability.

TABLE 18

Detection of Cytotoxicity of Humanized TPBG Antibody-Drug Conjugates on TPBG-Positive Cells via Cellular Killing Assay

| Sample Name | IC50 (nM) | | |
|---|---|---|---|
| | NCI-1568 | NCI-1975 | MDA-MB-468 |
| Humanized Antibody 12B12-12-MMAE | 0.43 | 1.20 | 0.27 |
| Humanized Antibody 12B12-12-MMAF | 0.05 | 0.13 | 0.06 |
| Humanized Antibody 12B12-12-DM1 | 0.38 | 5.93 | 0.44 |
| Humanized Antibody 12B12-12 | Negative | Negative | Negative |
| Human IgG | Negative | Negative | Negative |

Embodiment 8 Mouse Xenograft Model of Non-Small Cell Lung Carcinoma Cell Line NCI-H1975

200 µL of NCI-H1299 cells (non-small cell lung carcinoma cell line, ATCC, CRL-5908) ($2 \times 10^6$ cells) were inoculated subcutaneously in the right rib of Balb/c nude mice and allowed to grow for 7-10 days until the tumor volumes reach 200 mm³. After excluding the mice with too large or too small body weight and tumor size, the mice were randomly divided into several groups, i.e. 7 mice for each group, according to the tumor size. Grouping was shown in Table 19, therapeutic groupings of humanized 28D4-3-MMAF antibody-drug conjugate prepared in Embodiment 6 were prepared in different doses, as well as the same dose of humanized 12B12-12-MMAF and humanized 28D4-3-MMAF antibody-drugs conjugate treatment groups. Grouping was shown in Table 20, therapeutic grouping of humanized 28D4-3-MMAF, 28D4-3-MMAE and 28D4-3-DM1 antibody-drug conjugates coupled with different linker-toxins were prepared in the same dose. Antibody was injected intravenously to the tail at D0, and the injection was performed once every four days with a total of four injections. Tumor volume and body weight of mice were measured twice every week, and the data were recorded. Formula for calculating tumor volume is: $V = \frac{1}{2} \times a \times b^2$; wherein a and b represent length and width, respectively.

TABLE 19

In Vivo Pharmacodynamic Studies of Different Doses of Humanized TPBG Antibody-drug Conjugates in NCI-H1975 Mouse Xenograft Model

| Group | Number of Animals | Treating Group | Dose (mg/kg) | Injected Amount | Route of Administration | Administration Plan |
|---|---|---|---|---|---|---|
| 1 | 7 | Vehicle control | — | 10 μl/g | Tail intravenous injection i.v. | Administer once every 4 days × 4 times |
| 2 | 7 | Humanized Antibody 28D4-3-MMAF | 1 | 10 μl/g | Tail intravenous injection i.v. | Administer once every 4 days × 4 times |
| 3 | 7 | Humanized Antibody 28D4-3-MMAF | 3 | 10 μl/g | Tail intravenous injection i.v. | Administer once every 4 days × 4 times |
| 4 | 7 | Humanized Antibody 28D4-3-MMAF | 10 | 10 μl/g | Tail intravenous injection i.v. | Administer once every 4 days × 4 times |
| 5 | 7 | Humanized Antibody 12B12-12-MMAF | 10 | 10 μl/g | Tail intravenous injection i.v. | Administer once every 4 days × 4 times |

TABLE 20

In Vivo Pharmacodynamic Studies of humanized TPBG Antibody-drug Conjugates Coupled with Different Linker-Toxins in NCI-H1975 Mouse Xenograft Model

| Group | Number of Animals | Treating Group | Dose (mg/kg) | Injected Amount | Route of Administration | Administration Plan |
|---|---|---|---|---|---|---|
| 1 | 7 | Vehicle control | — | 10 μl/g | Tail intravenous i.v. | Administer once every 4 days × 4 times |
| 2 | 7 | Humanized Antibody 28D4-3-MMAF | 10 | 10 μl/g | Tail intravenous i.v. | Administer once every 4 days × 4 times |
| 3 | 7 | Humanized Antibody 28D4-3-MMAE | 10 | 10 μl/g | Tail intravenous i.v. | Administer once every 4 days × 4 times |
| 4 | 7 | Humanized Antibody 28D4-3-DM1 | 10 | 10 μl/g | Tail intravenous i.v. | Administer once every 4 days × 4 times |

FIG. 13A shows volume change of tumor after treatment with different doses of humanized 28D4-3-MMAF antibody-drug conjugate, and FIG. 13B shows weight change of mice after treatment with different doses of humanized 28D4-3-MMAF antibody-drug conjugate. The results showed that tumor volumes of all treated mice were significantly reduced compared to that of untreated mice, and tumor volumes of which decreased significantly with increasing dose. Moreover, tumor of the 10 mg/kg dose treated group gradually subsided in 35 days after administration, and the tumor began to slowly resume growth in subsequent continuous observation. In addition, MC-MMAF antibody-drug conjugated to humanized antibodies 12B12-12 and 28D4-3 were equally potent in the 10 mg/kg dose treated group.

FIG. 14A shows volume change of tumors after treatment at same dose of humanized 28D4-3-MMAF, 28D4-3-MMAE and 28D4-3-DM1 antibody-drug conjugates coupled with different linker-toxins, and FIG. 14B shows weight change after treatment of humanized 28D4-3-MMAF, 28D4-3-MMAE and 28D4-3-DM1 antibody-drug conjugates coupled with different linker-toxins at the same dose. The results showed that the tumor volumes of humanized 28D4-3 antibody-drug conjugates coupled to MC-MMAF and MC-VC-PAB-MMAE treated group were significantly diminished than that of untreated mice at the same dose. In the 50 days after administration, the tumor of the humanized 28D4-3-MMAF treatment group gradually resumed growth after the regression, and the tumors of the humanized 28D4-3-MMAE treated group were almost subsided. There was no reduction in tumor volume of the humanized 28D4-3 antibody-drug conjugate coupled with SMCC-DM1 treated group compared to that of untreated mice. It was shown that antibody-drug conjugates coupled to different linker-toxins have different inhibitory capacities for NCI-H1975 tumor growth.

Embodiment 9 Mouse Xenograft Model of Non-Small Cell Lung Carcinoma NCI-H1568

200 μL of NCI-H1568 cells (non-small cell lung carcinoma cell line, ATCC, CRL-5876) ($1 \times 10^7$ cells) were inoculated subcutaneously in the right rib of Balb/c nude mice and allowed to grow for 7-10 days until the tumor volumes reach 200 $mm^3$. After excluding the mice with too large or too small body weight and tumor size, the mice were randomly divided into several groups, i.e. 6 mice for each group, according to the tumor size. Grouping was shown in Table 21, therapeutic groupings of humanized 28D4-3-MMAF, 28D4-3-MMAE and 28D4-3-DM1 antibody-drug conjugates coupled with different linker-toxins were prepared in different doses. Antibody was injected intravenously to the tail at DO, and the injection was performed once every four days with a total of four injections. Tumor volume and body weight of mice were measured twice every week, and the data were recorded. Formula for calculating tumor volume is: $V = \frac{1}{2} \times a \times b^2$; wherein a and b represent length and width, respectively.

TABLE 21

In Vivo Pharmacodynamic Studies of Humanized TPBG Antibody-drug Conjugates in NCI-H1568 Mouse Xenograft Model

| Group | Number of Animals | Treating Group | Dose (mg/kg) | Injected Amount | Route of Administration | Administration Plan |
|---|---|---|---|---|---|---|
| 1 | 6 | Vehicle control | — | 10 μl/g | Tail intravenous injection i.v. | Administrate once every 4 days × 4 times |
| 2 | 6 | Humanized Antibody 12B12-12-MMAF | 2 | 10 μl/g | Tail intravenous injection i.v. | Administrate once every 4 days × 4 times |
| 3 | 6 | Humanized Antibody 12B12-12-MMAF | 10 | 10 μl/g | Tail intravenous injection i.v | Administrate once every 4 days × 4 times |
| 4 | 6 | Humanized Antibody 12B12-12-MMAE | 2 | 10 μl/g | Tail intravenous injection i.v. | Administrate once every 4 days × 4 times |
| 5 | 6 | Humanized Antibody 12B12-12-MMAE | 10 | 10 μl/g | Tail intravenous injection i.v | Administrate once every 4 days × 4 times |
| 6 | 6 | Humanized Antibody 12B12-12-DM1 | 10 | 10 μl/g | Tail intravenous injection i.v | Administrate once every 4 days × 4 times |

FIG. 15A shows volume change of tumors after treatment at different doses of humanized 12B12-12-MMAF, 12B12-12-MMAE and 12B12-12-DM1 antibody-drug conjugates coupled with different linker-toxins, and FIG. 15B shows weight change after treatment of humanized 12B12-12-MMAF, 12B12-12-MMAE and 12B12-12-DM1 antibody-drug conjugates coupled with different linker-toxins at different doses. The results showed that the tumor volume of all treated mice was significantly reduced compared to untreated mice. The high-dose 10 mg/kg treated group had a stronger inhibitory effect on NCI-H1568 tumors than the low-dose 2 mg/kg treated group. In addition, in the group after 35 days of administration with 10 mg/kg dose, tumor of humanized 12B12-12 antibody-drug conjugates coupled to MC-MMAF and MC-VC-PAB-MMAE treated groups were almost subsided, but humanized 12B12-12 antibody-drug conjugate coupled to SMCC-DM1 treated group gradually resumed growth after getting smaller. It showed that antibody-drug conjugates coupled to different linker-toxins had different inhibitory capacities for NCI-H1568 tumor growth.

Embodiment 10 Mouse Xenograft Model of Breast Cancer MDA-MB-468

200 μL of MDA-MB-468 cells (purchased from ATCC, HTB-132) ($1 \times 10^7$ cells) which were suspended in L-15 basal medium adding with 50% Matrigel were inoculated subcutaneously in the right rib of CB17 SCID mice and allowed to grow for 7-10 days until the tumor volumes reach 200 $mm^3$. After excluding the mice with too large or too small body weight and tumor size, the mice were randomly divided into several groups, i.e. 6 mice for each group, according to the tumor size. Grouping was shown in Table 22, therapeutic groupings of humanized 12B12-12-MMAF, 12B12-12-MMAE and 12B12-12-DM1 antibody-drug conjugates coupled with different linker-toxins were prepared in different doses. Antibody was injected intravenously to the tail at DO, and the injection was performed once every four days with a total of four injections. Tumor volume and body weight of mice were measured twice a week, and the data were recorded. Formula for calculating tumor volume is: $V = \frac{1}{2} \times a \times b^2$; wherein a and b represent length and width, respectively.

TABLE 22

In Vivo Pharmacodynamic Studies of Humanized TPBG Antibody-drug Conjugates in MDA-MB-468 Mouse Xenograft Model

| Group | Number of Animals | Treating Group | Dose (mg/kg) | Injected Amount | Route of Administration | Administration Plan |
|---|---|---|---|---|---|---|
| 1 | 6 | Vehicle control | — | 10 µl/g | Tail intravenous injection i.v. | Administrate once every 4 days × 4 times |
| 2 | 6 | Humanized Antibody 12B12-12-MMAF | 0.5 | 10 µL/g | Tail intravenous injection i.v. | Administrate once every 4 days × 4 times |
| 3 | 6 | Humanized Antibody 12B12-12-MMAF | 2 | 10 µL/g | Tail intravenous injection i.v. | Administrate once every 4 days × 4 times |
| 4 | 6 | Humanized Antibody 12B12-12-MMAE | 0.5 | 10 µL/g | Tail intravenous injection i.v. | Administrate once every 4 days × 4 times |
| 5 | 6 | Humanized Antibody 12B12-12-MMAE | 2 | 10 µL/g | Tail intravenous injection i.v. | Administrate once every 4 days × 4 times |
| 6 | 6 | Humanized Antibody 12B12-12-DM1 | 2 | 10 µL/g | Tail intravenous injection i.v. | Administrate once every 4 days × 4 times |

FIG. 16A shows volume change of tumors after treatment at different doses of humanized 12B12-12-MMAF, 12B12-12-MMAE and 12B12-12-DM1 antibody-drug conjugates coupled with different linker-toxins, and FIG. 16B shows weight change after treatment of humanized 12B12-12-MMAF, 12B12-12-MMAE and 12B12-12-DM1 antibody-drug conjugates coupled with different linker-toxins at different doses. Results showed that all the tumor volume of human 28D4-3 antibody-drug conjugates coupled to MC-MMAF and MC-VC-PAB-MMAE treated groups were significantly diminished than that of untreated mice. In addition, in the group after 43 days of administration with 2 mg/kg dose, tumor of humanized 12B12-12 antibody-drug conjugates coupled to MC-MMAF and MC-VC-PAB-MMAE treated groups basically subsided, but humanized 12B12-12 antibody-drug conjugate coupled to SMCC-DM1 treated group gradually resumed growth after getting smaller. It showed that antibody-drug conjugates coupled to different linker-toxins had different inhibitory capacities for NCI-H1568 tumor growth.

Embodiment 11 Stability of Humanized Anti-TPBG Antibody-Drug Conjugates in Rat Serum 3 mg/kg of humanized 28D4-MMAE conjugate was injected into Sprague-Dawley rats (purchased from Shanghai Slack Laboratory Animal Co., Ltd.) by a single intravenous injection of tail vein. 200 µl of whole blood was collected respectively before injection, 10 minutes after injection, 1 hour, 4 hours, 8 hours, and 1, 2, 4, 7, 14, 21 and 28 days, and serum was collected after centrifugation at 14,000 rpm for 5 minutes. The concentration of total anti-TPBG antibody (the total anti-TPBG antibody comprises naked antibody and antibody-drug conjugates) and the antibody drug conjugates coupled to at least one cytotoxic drug in serum were determined by ELISA. The concentration of total humanized anti-TPBG antibody in the serum was detected by ELISA, and captured using anti-human Fc antibody and detected using horseradish peroxidase (HRP) conjugated anti-mouse Fc antibody. The concentration of the antibody drug conjugate carrying at least one cytotoxic drug in the serum was detected by ELISA, and captured using an anti-MMAE antibody and detected using a horseradish peroxidase (HRP)-conjugated anti-mouse Fc antibody, wherein, anti-MMAE antibody (trade name anti-MMAF-mIgG1, purchased from Shanghai Ruizhi Chemical Research Co., Ltd.) was prepared by using hybridoma technology. Anti-human Fc antibody and anti-MMAE antibody were separately diluted with PBS to a certain concentration (2-5 µg/ml), coated on a 96-well ELISA plate at 4° C. overnight. The liquid in the well was discarded and spin dried, and the blocking solution (PBS, 1% BSA, 0.05% Tween-20) was added and blocked for 1 hour at room temperature, and then washed 3 times with PBST (PBS, 0.05% Tween-20) for later use. Diluted the standard sample to a certain concentration with PBST, and prepare serum sample as appropriate. Added 200 µl/well of the diluted serum sample or standard sample to the coated 96-well plate and incubated for 1-3 hours at room temperature. The supernatant was discarded and the plate was washed 3 times with PBST; then horseradish peroxidase (HRP)-conjugated anti-mouse Fc antibody was diluted with PBS to an appropriate concentration, and 100 µl of which was added to each well of a 96-well plate and incubated for 30 minutes at 37° C. After the supernatant was discarded, the plate was washed 3 times with PBST; 100 µl of TMB coloring solution was added to each well, and incubated at room temperature for 5-10 minutes. 100 µl of 2N sulfuric acid stop solution was added to each well to terminate the reaction, and the ratio of OD 450 nm/630 nm was measured by a microplate reader. The data of concentration of total antibody and conjugate thereof in serum at different sampling time points from each animal were analyzed using a two compartment model with IV bolus input, first order elimination and macro rate constant (Model 8, WinNonlinear Pro v. 5.0.1, Pharsight Corporation, Mountain View, Calif.) to analyze the in vivo stability of the humanized anti-TPBG antibody drug conjugate.

The results of the 28-day pharmacokinetic analysis performed in rats were shown in FIG. 17 and Table 23. In Table 23, CL represents the total clearance rate, and the higher CL value the faster metabolism or clearance; $V_{SS}$ represents the apparent volume of distribution in steady state, and the higher $V_{SS}$ value the wider tissue distribution; V1 represents the volume of distribution of the central chamber, and the value of V1 should be close to the serum volume per kilogram of the experimental animals; Alpha t1/2 represents the distribution phase half-life, which is related to the distribution rate; Beta t1/2 represents the elimination phase half-life, which is related to the elimination rate; AUC is the area under concentration-time curve at time of administration, which represents the exposure of the test substance in serum. Exposure amount in general time is directly related to the efficacy of drug.

TABLE 23

Drug Metabolism of Anti-TPBG Antibody MMAE conjugate 28D4-3-MMAE in Rats

| | \multicolumn{6}{c}{PK Parameter} | | | | | |
|---|---|---|---|---|---|---|
| | CL | Vss | V1 | Alpha $t_{1/2}$ | Beta $t_{1/2}$ | AUC |
| | \multicolumn{6}{c}{Unit} | | | | | |
| | mL/day/kg | mL/kg | mL/kg | day | day | day * µg/mL |
| Total Antibody | 17.2 ± 1.8 | 225 ± 16.1 | 60.7 ± 0.61 | 0.39 ± 0.016 | 10.4 ± 1.5 | 176 ± 17.8 |
| Conjugated Antibody | 51.3 ± 2.7 | 246 ± 23.4 | 70.8 ± 0.73 | 0.52 ± 0.052 | 6.18 ± 1.0 | 58.5 ± 3.0 |

From the results, conjugated antibody and total antibody had similar pharmacokinetic characteristics, such as long half-life, nonlinear distribution and elimination. The difference is that conjugated antibody shows a higher clearance rate (CL) and a lower elimination half-life (Beta $t_{1/2}$) and exposure (AUC) compared to total antibody, which is consistent with the classical ADC drug metabolism. The reason may be that the ADC drug is a mixture of various molecules with high heterogeneity, and some of the conjugates degrade in the blood circulation or induce immune response, so that the body generates antibodies against the ADC drug, resulting in the clearance of the ADC drug.

Embodiment 12 Pharmacodynamic Experiment of Humanized Anti-TPBG Antibody-Drug Conjugate in Human Tumor Patient-Derived Xenograft Model (PDX)

The PDX model is a non-small cell lung carcinoma (NSCLC) human tumor model (a xenograft model in which a patient's tumor tissue is inoculated into a mouse and grow relying on the environment provided by the mouse; the PDX model of the present invention is purchased from Shanghai Ruizhi Chemical Research Co., Ltd.). The expression of TPBG in the NSCLC PDX model was assessed by immunohistochemistry. Briefly, fresh tumor tissue of PDX model was quick-frozen using liquid nitrogen and stored in −80° C. refrigerator. Fresh tumor tissue of PDX model was sliced with a microtome, fixed with 4% paraformaldehyde for 10 minutes at room temperature; incubated with 3% hydrogen peroxide at room temperature for 5 minutes at room temperature to block endogenous peroxidase; and incubated with 5% fetal bovine serum at room temperature to block non-specific protein binding sites for 15 minutes. Tissue slices were incubated with humanized anti-TPBG antibody 12B12-12 or isotype control antibody hIgG for 1 hour at room temperature; incubated with Goat anti-human IgG (H+L) Secondary Antibody, HRP conjugate (purchased from Thermo) at room temperature for 30 minutes, and DAB chromogenic for 5 minutes. The slice was then placed in a tank containing tap water to terminate the reaction; counterstained with hematoxylin for 10 seconds, and rinsed with tap water for 3 times; followed by differentiating by hydrochloric acid alcohol for 1 second, and rinsing with tap water for 3 minutes; subsequently, the slice was dehydrated with 75% alcohol for 2 minutes, 95% alcohol for 2 minutes, 100% alcohol for 3 times, and xylene for 3 times for 2 minutes each. Then, the slice was sealed with neutral gum, and the staining results were observed under a microscope and photographed. The expression level of TPBG in the PDX model was shown in FIGS. 18A-B, wherein FIG. 18A is the staining of humanized anti-TPBG antibody 12B12-3 on PDX model tumor tissue slices, and FIG. 18B is the stain of negative control antibody hIgG in the PDX model tumor tissue slices. Based on the results shown in FIG. 18, the PDX model can be used for subsequent pharmacodynamic experiment The cryopreserved P1 generation (the first generation of tumor tissue samples of the above-described PDX model) tumor samples (FP1) were taken out from the liquid nitrogen storage tank, and then thawed and subcutaneously inoculated into SCID mice (purchased from Beijing Vital River Laboratory Animal Technology Co., Ltd.), and named FP1+1. The health status of the mice was monitored daily and tumor growth was initially monitored twice a week by visual inspection. Mouse body weight was recorded 2 to 3 times a week. The tumor diameter was measured with vernier caliper 2 to 3 times a week. The tumor volume is calculated as: $V = \frac{1}{2} a \times b^2$, and a and b represent the long and short diameters of the tumor, respectively. When the tumor grows to 1000 mm$^3$, the mice are euthanized, and fresh tumor tissue of mice is taken out, cut into small pieces and subcutaneously inoculated into female nude mice. After being passaged three times or more by this method, such mice were tested for pharmacodynamic studies (named FP1+3).

Female Nu/Nu mice with 6-8 weeks age and 16-19 g weight were purchased (purchased from Beijing Vital River Laboratory Animal Technology Co., Ltd.). Experiment began 7 days after the animals arrived and fed in IVC (Individual Ventilated Cages) in the SPF animal room. Since individual differences in mice may result in difference in the growth rate of tumor tissue, therefore, it is necessary to prepare at least extra 50% of the number of animals to allow the minimum tumor volume variance at randomization.

Female Nu/Nu mice were inoculated via the above-mentioned resuscitation tumor tissue, and the health status of the mice was monitored daily and tumor growth was initially monitored twice a week by visual inspection, followed by recording the body weight of the mice 2 to 3 times per week. When the tumor can be touched, the tumor diameter was measured with vernier caliper 2 to 3 times a week and the tumor volume was calculated. After the tumor volume was as big as 100 mm$^3$, the mice with too large or too small body weight and tumor size were excluded, and remaining mice were randomly grouped according to the tumor volume, with 10 mice in each group (groupings was shown in Table 24). Therapeutic groupings of humanized 12B12-12-MMAF, 12B12-12-MMAE and 12B12-12-DM1 antibody-drug conjugates coupled with different linker-toxins were prepared in different doses. Mice were injected with the antibody into the tail vein on D0, and administrated once every 4 days×4 times. The tumor volume was measured twice a week, the rats were weighed, and the data were recorded. The tumor volume (V) is calculated as: ½a×b$^2$; wherein a and b represent length and width, respectively.

TABLE 24

Pharmacodynamic Studies of Humanized Anti-TPBG Antibody-drug Conjugate in Human Tumor Patient-derived Xenograft Model (PDX)

| Group | Number of Animals | Treating Group | Dose (mg/kg) | Injected Amount | Route of Administration | Administration Plan |
|---|---|---|---|---|---|---|
| 1 | 10 | Vehicle control | — | 10 µl/g | Tail intravenous injection i.v. | Administrate once every 4 days × 4 times |
| 2 | 10 | Humanized Antibody 28D4-3-MMAE | 1 | 10 µL/g | Tail intravenous injection i.v. | Administrate once every 4 days × 4 times |
| 3 | 10 | Humanized Antibody 28D4-3-MMAE | 3 | 10 µL/g | Tail intravenous injection i.v. | Administrate once every 4 days × 4 times |
| 4 | 10 | Humanized Antibody 28D4-3-MMAE | 10 | 10 µL/g | Tail intravenous injection i.v. | Administrate once every 4 days × 4 times |

FIG. 19A shows the volume change of tumors after treatment at different doses of humanized 28D4-MMAE conjugate, and FIG. 19B shows weight change after treatment of humanized 28D4-MMAE conjugate at different doses. Results showed that tumor volume of untreated group continued to grow, and the mouse with tumor volume exceeding 1800 mm$^3$ was euthanized on the 35th day of the experiment. All the tumor volume of treated mice were significantly diminished than that of untreated ones. Tumor growth was inhibited 3 days after administration, and tumor growth was significantly inhibited 10 days after administration. Moreover, tumors were completely regressed in doses of 1, 3, and 10 mg/ml after 28 days of administration, and the tumor regression state was maintained in one month's observation thereafter, indicating that the anti-TPBG antibody-MMAE conjugate significantly inhibited the growth of patient-derived non-small cell lung carcinoma xenograft tumor PDX in vivo in mouse.

Embodiment 13 Inhibition of Tumor Growth and Formation of Immunological Memory in Mice Under Treatment of Humanized Anti-TPBG Antibody-Drug Conjugate Combined with Anti-PD-1 Antibody Preparation method and flow cytometry detection method of CT26 stable cell line expressing human TPBG (CT26-hTPBG stable cell line) (purchased from Shanghai Ruizhi Chemical Research Co., Ltd.), are the same with Embodiment 1 (b) "Preparation of Immunogen B", in which mouse colon cancer cell CT26 was purchased from ATCC.

50 µL of CT26-TPBG cells (1×10$^6$ cells) were inoculated subcutaneously in the right rib of Balb/c nude mice and allowed to grow for 7-10 days. 32 animals with tumor volumes of 50-100 mm$^3$ were selected. Mice were randomly divided into 4 groups according to tumor volume, 8 in each group. Those groups comprise vehicle group, treated group of humanized 28D4-3-MMAE antibody-drug conjugate alone, treated group of anti-PD-1 alone, and combination treated group comprising humanized 28D4-3-MMAE antibody-drug conjugate and anti-PD-1. The grouping was shown in Table 25.

Humanized 28D4-3-MMAE antibody-drug conjugate was administered once i.v. on the day of grouping (defined as D0). Anti-PD-1 antibody was administered i.p. from D0 twice a week for 8 times in total. The body weight of the mice was recorded twice a week, and the length and diameter of the tumor were measured with vernier caliper. The tumor volume V was calculated by the following formula: V=½a×b$^2$; wherein a and b represent the long diameter and short diameter of the tumor, respectively. Animals with a tumor volume of 2000 mm$^3$, which were deemed to have reached the end of the experiment, were euthanized and the survival of the animals were analyzed.

TABLE 25

In vivo Pharmacodynamic Studies of Humanized TPBG Antibody Drug Conjugates or/with Anti-PD-1 Antibodies in Tumor Models

| Group | Number of Animals | Treating Group | Dose (mg/kg) | Injected Amount | Route of Administration | Schedule of Administration |
|---|---|---|---|---|---|---|
| 1 | 8 | Vehicle control | — | 10 μl/g | Tail intravenous i.v. | Administrate twice a week × 4 times |
| 2 | 8 | Humanized 28D4-3-MMAE Antibody-drug Conjugate | 1 | 10 μl/g | Tail intravenous i.v. | Administrate on D0 |
| 3 | 8 | Anti-PD-1 Antibody | 5 | 10 μl/g | Intraperitoneal i.p. | Administrate twice a week × 4 times |
| 4 | 8 | humanized 28D4-3-MMAE Antibody-drug Conjugate + Anti-PD-1 Antibody Conjugates | ADC: 1; Antibody: 5; | 10 μl/g | Tail intravenous i.v. Intraperitoneal i.p. | Administrate on D0; Administer twice a week × 4 times |

Tumor growth curves of each group showed that tumor growth was significantly inhibited in each drug-administered group at D14 days after administration compared with vehicle group, and the tumor suppression effect of the combination treatment group was significantly better than that of the monotherapy group (FIG. 20A, p value <0.001, two-way repeated measures analysis of variance). Survival analysis with tumor volume of 2000 mm³ as the end point of the experiment showed that the monotherapy and combination therapy of humanized 28D4-3-MMAE antibody-drug conjugate and anti-PD-1 significantly prolonged the survival of tumor-bearing mice compared to the vehicle group. And combination therapy was significantly superior to monotherapy (FIG. 20B, p-value <0.05, log-rank test). In addition, the growth of individual tumor in each group was analyzed and results showed that tumor volumes of control group and each monotherapy treatment group reached 2000 mm³ within 60 days. In contrast, the combination treatment group showed complete tumor regression on D12 after administration. On D60, tumors of 3 animals in the combination treatment group were completely eliminated, indicating that the complete remission rate reached 37.5% (FIG. 20C). On D106, the same number of CT26-hTPBG cells were inoculated subcutaneously in the left rib of 3 complete remission mice, and no tumor formation was observed in the mice during the second 30-day $2^{nd}$ inoculation period, suggesting that immunological memory has been formed in these mice. (FIG. 20D).

In conclusion, the humanized 28D4-3-MMAE antibody-drug conjugate significantly enhanced the anti-tumor activity of anti-PD-1 antibody against CT26-hTPBG mouse model. The complete remission rate of combination therapy of the two drugs reached 37.5%. The combination therapy of humanized 28D4-3-MMAE antibody-drug conjugate and anti-PD-1 antibody could significantly prolong the survival of the mice compared to humanized 28D4-3-MMAE antibody-drug conjugate or anti-PD-1 monotherapy, and the mice with complete tumor remission after combination treatment will form immunological memory.

The specific embodiments of the present invention described above are merely illustrative, and it should be understood that after reading the above contents of the present invention, those skilled in the art can make various changes or modifications to the present invention without departing from the principles and spirits of the present invention. Therefore, the scope of protection of the present invention is defined by the appended claims.

The invention claimed is:

1. A humanized anti-TPBG antibody comprising:
   (a) a framework region containing residues of a human antibody framework region; and
   (b) one or more CDRs of the mouse-derived antibody light chain variable region set forth in SEQ ID NO: 4 or 8, or one or more CDRs of the mouse-derived antibody heavy chain variable region set forth in SEQ ID NO: 2 or 6;
   wherein the humanized anti-TPBG antibody comprises at least one heavy chain variable region and one light chain variable region,
   wherein the amino acid sequence of the heavy chain variable region is set forth in SEQ ID NO: 18 and the amino acid sequence of the light chain variable region is set forth in SEQ ID NO: 26
   or, the amino acid sequence of the heavy chain variable region is set forth in SEQ ID NO: 20 and the amino acid sequence of the light chain variable region is set forth in SEQ ID NO: 26;
   or, the amino acid sequence of the heavy chain variable region is set forth in SEQ ID NO: 24 and the amino acid sequence of the light chain variable region is set forth in SEQ ID NO: 26;
   or, the amino acid sequence of the heavy chain variable region is set forth in SEQ ID NO: 16 and the amino acid sequence of the light chain variable region is set forth in SEQ ID NO: 28;
   or, the amino acid sequence of the heavy chain variable region is set forth in SEQ ID NO: 18 and the amino acid sequence of the light chain variable region is set forth in SEQ ID NO: 28;
   or, the amino acid sequence of the heavy chain variable region is set forth in SEQ ID NO: 20 and the amino acid sequence of the light chain variable region is set forth in SEQ ID NO: 28;
   or, the amino acid sequence of the heavy chain variable region is set forth in SEQ ID NO: 22 and the amino acid sequence of the light chain variable region is set forth in SEQ ID NO: 28;
   or, the amino acid sequence of the heavy chain variable region is set forth in SEQ ID NO: 24 and the amino acid sequence of the light chain variable region is set forth in SEQ ID NO: 28;
   or, the amino acid sequence of the heavy chain variable region is set forth in SEQ ID NO: 18 and the amino acid sequence of the light chain variable region is set forth in SEQ ID NO: 30;

or, the amino acid sequence of the heavy chain variable region is set forth in SEQ ID NO: 20 and the amino acid sequence of the light chain variable region is set forth in SEQ ID NO: 30;

or, the amino acid sequence of the heavy chain variable region is set forth in SEQ ID NO: 24 and the amino acid sequence of the light chain variable region is set forth in SEQ ID NO: 30;

or, the amino acid sequence of the heavy chain variable region is set forth in SEQ ID NO: 16 and the amino acid sequence of the light chain variable region is set forth in SEQ ID NO: 32;

or, the amino acid sequence of the heavy chain variable region is set forth in SEQ ID NO: 18 and the amino acid sequence of the light chain variable region is set forth in SEQ ID NO: 32;

or, the amino acid sequence of the heavy chain variable region is set forth in SEQ ID NO: 20 and the amino acid sequence of the light chain variable region is set forth in SEQ ID NO: 32;

or, the amino acid sequence of the heavy chain variable region is set forth in SEQ ID NO: 22 and the amino acid sequence of the light chain variable region is set forth in SEQ ID NO: 32;

or, the amino acid sequence of the heavy chain variable region is set forth in SEQ ID NO: 24 and the amino acid sequence of the light chain variable region is set forth in SEQ ID NO: 32;

or, the amino acid sequence of the heavy chain variable region is set forth in SEQ ID NO: 34 and the amino acid sequence of the light chain variable region is set forth in SEQ ID NO: 42;

or, the amino acid sequence of the heavy chain variable region is set forth in SEQ ID NO: 36 and the amino acid sequence of the light chain variable region is set forth in SEQ ID NO: 42;

or, the amino acid sequence of the heavy chain variable region is set forth in SEQ ID NO: 38 and the amino acid sequence of the light chain variable region is set forth in SEQ ID NO: 42;

or, the amino acid sequence of the heavy chain variable region is set forth in SEQ ID NO: 40 and the amino acid sequence of the light chain variable region is set forth in SEQ ID NO: 42;

or, the amino acid sequence of the heavy chain variable region is set forth in SEQ ID NO: 34 and the amino acid sequence of the light chain variable region is set forth in SEQ ID NO: 44;

or, the amino acid sequence of the heavy chain variable region is set forth in SEQ ID NO: 36 and the amino acid sequence of the light chain variable region is set forth in SEQ ID NO: 44;

or, the amino acid sequence of the heavy chain variable region is set forth in SEQ ID NO: 38 and the amino acid sequence of the light chain variable region is set forth in SEQ ID NO: 44;

or, the amino acid sequence of the heavy chain variable region is set forth in SEQ ID NO: 40 and the amino acid sequence of the light chain variable region is set forth in SEQ ID NO: 44;

or, the amino acid sequence of the heavy chain variable region is set forth in SEQ ID NO: 34 and the amino acid sequence of the light chain variable region is set forth in SEQ ID NO: 46;

or, the amino acid sequence of the heavy chain variable region is set forth in SEQ ID NO: 36 and the amino acid sequence of the light chain variable region is set forth in SEQ ID NO: 46;

or, the amino acid sequence of the heavy chain variable region is set forth in SEQ ID NO: 38 and the amino acid sequence of the light chain variable region is set forth in SEQ ID NO: 46;

or, the amino acid sequence of the heavy chain variable region is set forth in SEQ ID NO: 40 and the amino acid sequence of the light chain variable region is set forth in SEQ ID NO: 46.

2. The humanized anti-TPBG antibody according to claim 1, wherein the humanized anti-TPBG antibody further comprises a heavy chain constant region and a light chain constant region of human antibody.

3. The humanized anti-TPBG antibody according to claim 1, wherein the humanized anti-TPBG antibody is a full-length protein of antibody, a protein fragment of antigen-antibody binding domain, a dual-specificity antibody, a multiple-specificity antibody, a single chain antibody, a single domain antibody or a single-region antibody;
or, the humanized anti-TPBG antibody is a monoclonal antibody or a polyclonal antibody;
or, the humanized anti-TPBG antibody is a super-humanized antibody or a double antibody.

4. A nucleic acid encoding the humanized anti-TPBG antibodies according to claim 1.

5. The nucleic acid according to claim 4, wherein the amino acid sequence encoded by the nucleic acid of the heavy chain variable region is set forth in SEQ ID NO: 18, and the amino acid sequence of the variable region of the light chain is set forth in SEQ ID NO: 26;

or, the amino acid sequence encoded by the nucleic acid of the heavy chain variable region is set forth in SEQ ID NO: 20, and the amino acid sequence of the variable region of the light chain is set forth in SEQ ID NO: 26;

or, the amino acid sequence encoded by the nucleic acid of the heavy chain variable region is set forth in SEQ ID NO: 24, and the amino acid sequence of the variable region of the light chain is set forth in SEQ ID NO: 26;

or, the amino acid sequence encoded by the nucleic acid of the heavy chain variable region is set forth in SEQ ID NO: 16, and the amino acid sequence of the variable region of the light chain is set forth in SEQ ID NO: 28;

or, the amino acid sequence encoded by the nucleic acid of the heavy chain variable region is set forth in SEQ ID NO: 18, and the amino acid sequence of the variable region of the light chain is set forth in SEQ ID NO: 28;

or, the amino acid sequence encoded by the nucleic acid of the heavy chain variable region is set forth in SEQ ID NO: 20, and the amino acid sequence of the variable region of the light chain is set forth in SEQ ID NO: 28;

or, the amino acid sequence encoded by the nucleic acid of the heavy chain variable region is set forth in SEQ ID NO: 22, and the amino acid sequence of the variable region of the light chain is set forth in SEQ ID NO: 28;

or, the amino acid sequence encoded by the nucleic acid of the heavy chain variable region is set forth in SEQ ID NO: 24, and the amino acid sequence of the variable region of the light chain is set forth in SEQ ID NO: 28;

or, the amino acid sequence encoded by the nucleic acid of the heavy chain variable region is set forth in SEQ ID NO: 18, and the amino acid sequence of the variable region of the light chain is set forth in SEQ ID NO: 30;

or, the amino acid sequence encoded by the nucleic acid of the heavy chain variable region is set forth in SEQ ID NO: 20, and the amino acid sequence of the variable region of the light chain is set forth in SEQ ID NO: 30;

or, the amino acid sequence encoded by the nucleic acid of the heavy chain variable region is set forth in SEQ ID NO: 24, and the amino acid sequence of the variable region of the light chain is set forth in SEQ ID NO: 30;

or, the amino acid sequence encoded by the nucleic acid of the heavy chain variable region is set forth in SEQ ID NO: 16, and the amino acid sequence of the variable region of the light chain is set forth in SEQ ID NO: 32;

or, the amino acid sequence encoded by the nucleic acid of the heavy chain variable region is set forth in SEQ ID NO: 18, and the amino acid sequence of the variable region of the light chain is set forth in SEQ ID NO: 32;

or, the amino acid sequence encoded by the nucleic acid of the heavy chain variable region is set forth in SEQ ID NO: 20, and the amino acid sequence of the variable region of the light chain is set forth in SEQ ID NO: 32;

or, the amino acid sequence encoded by the nucleic acid of the heavy chain variable region is set forth in SEQ ID NO: 22, and the amino acid sequence of the variable region of the light chain is set forth in SEQ ID NO: 32;

or, the amino acid sequence encoded by the nucleic acid of the heavy chain variable region is set forth in SEQ ID NO: 24, and the amino acid sequence of the variable region of the light chain is set forth in SEQ ID NO: 32;

or, the amino acid sequence encoded by the nucleic acid of the heavy chain variable region is set forth in SEQ ID NO: 34, and the amino acid sequence of the variable region of the light chain is set forth in SEQ ID NO: 42;

or, the amino acid sequence encoded by the nucleic acid of the heavy chain variable region is set forth in SEQ ID NO: 36, and the amino acid sequence of the variable region of the light chain is set forth in SEQ ID NO: 42;

or, the amino acid sequence encoded by the nucleic acid of the heavy chain variable region is set forth in SEQ ID NO: 38, and the amino acid sequence of the variable region of the light chain is set forth in SEQ ID NO: 42;

or, the amino acid sequence encoded by the nucleic acid of the heavy chain variable region is set forth in SEQ ID NO: 40, and the amino acid sequence of the variable region of the light chain is set forth in SEQ ID NO: 42;

or, the amino acid sequence encoded by the nucleic acid of the heavy chain variable region is set forth in SEQ ID NO: 34, and the amino acid sequence of the variable region of the light chain is set forth in SEQ ID NO: 44;

or, the amino acid sequence encoded by the nucleic acid of the heavy chain variable region is set forth in SEQ ID NO: 36, and the amino acid sequence of the variable region of the light chain is set forth in SEQ ID NO: 44;

or, the amino acid sequence encoded by the nucleic acid of the heavy chain variable region is set forth in SEQ ID NO: 38, and the amino acid sequence of the variable region of the light chain is set forth in SEQ ID NO: 44;

or, the amino acid sequence encoded by the nucleic acid of the heavy chain variable region is set forth in SEQ ID NO: 40, and the amino acid sequence of the variable region of the light chain is set forth in SEQ ID NO: 44;

or, the amino acid sequence encoded by the nucleic acid of the heavy chain variable region is set forth in SEQ ID NO: 34, and the amino acid sequence of the variable region of the light chain is set forth in SEQ ID NO: 46;

or, the amino acid sequence encoded by the nucleic acid of the heavy chain variable region is set forth in SEQ ID NO: 36, and the amino acid sequence of the variable region of the light chain is set forth in SEQ ID NO: 46;

or, the amino acid sequence encoded by the nucleic acid of the heavy chain variable region is set forth in SEQ ID NO: 38, and the amino acid sequence of the variable region of the light chain is set forth in SEQ ID NO: 46;

or, the amino acid sequence encoded by the nucleic acid of the heavy chain variable region is set forth in SEQ ID NO: 40, and the amino acid sequence of the variable region of the light chain is set forth in SEQ ID NO: 46.

6. A recombinant expression vector comprising the nucleic acid according to claim 4.

7. A recombinant expression transformant comprising the recombinant expression vector according to claim 6.

8. A preparation method of humanized anti-TPBG antibody according claim 1, which comprises following steps: culturing the recombinant expression vector according to claim 7, obtaining humanized anti-TPBG antibody from culture.

9. An immunoconjugate comprising the humanized anti-TPBG antibody according to claim 1 which is covalently linked to a cytotoxic agent.

10. The immunoconjugate according to claim 9, wherein the humanized anti-TPBG antibody according to claim 1 is linked to y equivalent of cytotoxic agent through x equivalent of linker, which has the structure shown in formula 1,

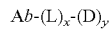  Formula 1 wherein Ab is the humanized anti-TPBG antibody according to claim 1, L is linker; D is cytotoxic agent; x is natural number.

11. The immunoconjugate according to claim 10, wherein the linker L is active esters, carbonates, carbamates, imine phosphate esters, oximes, hydrazones, acetals, orthoesters, aminos, small peptides or nucleotide fragments.

12. The immunoconjugate according to claim 11, wherein the linker L is selected from maleimidocaproyl (MC), maleimidocaproyl-L-valine-L-citrulline p-amino benzyl alcohol (MC-VC-PAB), 4-(N-maleimide methyl) cyclohexane-1-carboxylic succinimide (SMCC); and/or, the D is selected from cytotoxin, chemotherapeutic agent, radioisotope, therapeutic nucleic acid, immunomodulator, anti-angiogenic agents, anti-proliferative and pro-apoptotic agent or cytolytic enzyme.

13. The immunoconjugate according to claim 9, wherein x=y=n in formula 1, and the structure of the immunoconjugate is shown in formula 3, 4 or 5, Formula 3

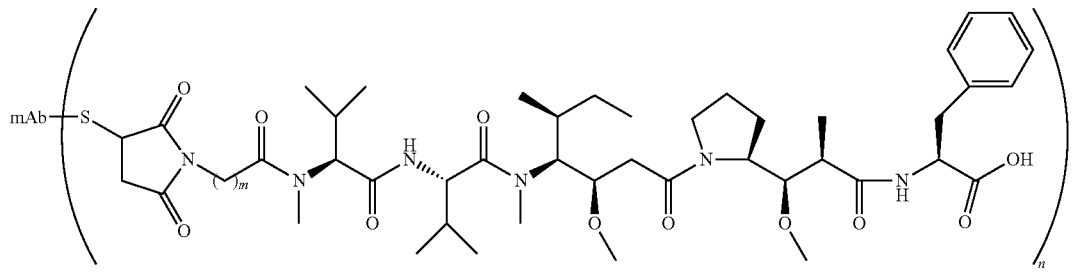

in formula 3, m is 1-10; D is methylauristatin F;

Formula 4

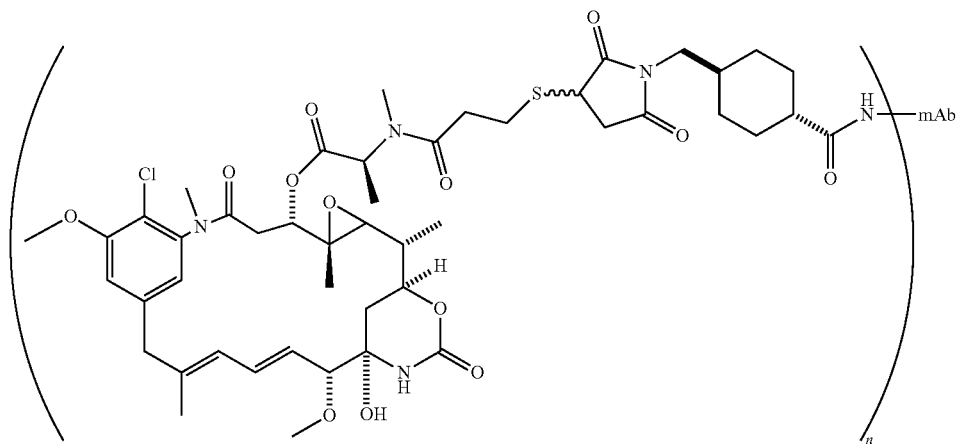

in formula 4, L is 4-(N-maleimide methyl) cyclohexane-1-carboxylic succinimide; D is N2-deacetyl-N2'-(3-mercapto-1-oxypropyl) methesteine (DM1);

Formula 5

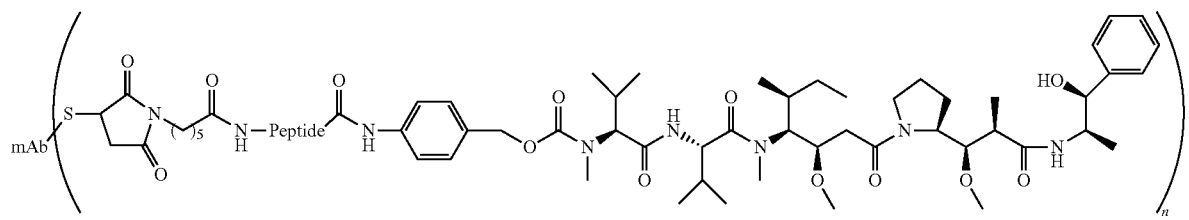

in formula 5, L is maleimidocaproyl-L-valine-L-citrulline p-amino benzyl alcohol, D is methylauristatin E (MMAE);

wherein n is a natural number.

14. A pharmaceutical composition comprising the immunoconjugate according to claim 9 and pharmaceutically acceptable vehicle.

15. A package of medical kits, comprising a component A and a component B, the component A is the humanized anti-TPBG antibody according to claim 1, or the immunoconjugate according to claim 9, or the pharmaceutical composition according to claim 14, wherein the component B is the other anti-tumor antibodies or pharmaceutical composition comprising other anti-tumor antibodies.

16. A method for treating a tumor in a subject in need thereof, comprising: administering a humanized anti-TPBG antibody according to claim 1, or an immunoconjugate according to claim 9, or a pharmaceutical composition according to claim 14, or a package of medical kits to the subject.

17. A method for detecting cells overexpressing TPBG protein, which comprises the following steps: contacting the humanized anti-TPBG antibody according to claim 1 with the sample to be tested in vitro, and detecting the binding of the humanized anti-TPBG antibody according to claim 1 with the sample to be tested.

18. The humanized anti-TPBG antibody according to claim 1, wherein the amino acid sequence of the heavy chain variable region is set forth in SEQ ID NO: 34 and the amino acid sequence of the light chain variable region is set forth in SEQ ID NO: 42;
- or, the amino acid sequence of the heavy chain variable region is set forth in SEQ ID NO: 36 and the amino acid sequence of the light chain variable region is set forth in SEQ ID NO: 42;
- or, the amino acid sequence of the heavy chain variable region is set forth in SEQ ID NO: 38 and the amino acid sequence of the light chain variable region is set forth in SEQ ID NO: 42;
- or, the amino acid sequence of the heavy chain variable region is set forth in SEQ ID NO: 40 and the amino acid sequence of the light chain variable region is set forth in SEQ ID NO: 42;
- or, the amino acid sequence of the heavy chain variable region is set forth in SEQ ID NO: 34 and the amino acid sequence of the light chain variable region is set forth in SEQ ID NO: 44;
- or, the amino acid sequence of the heavy chain variable region is set forth in SEQ ID NO: 36 and the amino acid sequence of the light chain variable region is set forth in SEQ ID NO: 44;
- or, the amino acid sequence of the heavy chain variable region is set forth in SEQ ID NO: 38 and the amino acid sequence of the light chain variable region is set forth in SEQ ID NO: 44;
- or, the amino acid sequence of the heavy chain variable region is set forth in SEQ ID NO: 40 and the amino acid sequence of the light chain variable region is set forth in SEQ ID NO: 44;
- or, the amino acid sequence of the heavy chain variable region is set forth in SEQ ID NO: 34 and the amino acid sequence of the light chain variable region is set forth in SEQ ID NO: 46;
- or, the amino acid sequence of the heavy chain variable region is set forth in SEQ ID NO: 36 and the amino acid sequence of the light chain variable region is set forth in SEQ ID NO: 46;
- or, the amino acid sequence of the heavy chain variable region is set forth in SEQ ID NO: 38 and the amino acid sequence of the light chain variable region is set forth in SEQ ID NO: 46;
- or, the amino acid sequence of the heavy chain variable region is set forth in SEQ ID NO: 40 and the amino acid sequence of the light chain variable region is set forth in SEQ ID NO: 46.

19. The humanized anti-TPBG antibody according to claim 1, wherein the amino acid sequence of the heavy chain variable region is set forth in SEQ ID NO: 38 and the amino acid sequence of the light chain variable region is set forth in SEQ ID NO: 42;
- or, the amino acid sequence of the heavy chain variable region is set forth in SEQ ID NO: 40 and the amino acid sequence of the light chain variable region is set forth in SEQ ID NO: 42;
- or, the amino acid sequence of the heavy chain variable region is set forth in SEQ ID NO: 38 and the amino acid sequence of the light chain variable region is set forth in SEQ ID NO: 44;
- or, the amino acid sequence of the heavy chain variable region is set forth in SEQ ID NO: 40 and the amino acid sequence of the light chain variable region is set forth in SEQ ID NO: 44;
- or, the amino acid sequence of the heavy chain variable region is set forth in SEQ ID NO: 40 and the amino acid sequence of the light chain variable region is set forth in SEQ ID NO: 46.

20. The humanized anti-TPBG antibody according to claim 1, wherein the amino acid sequence of the heavy chain variable region is set forth in SEQ ID NO: 38 and the amino acid sequence of the light chain variable region is set forth in SEQ ID NO: 42.

\* \* \* \* \*